US012790348B2

(12) United States Patent
Hiraoka et al.

(10) Patent No.: US 12,790,348 B2
(45) Date of Patent: Nov. 10, 2026

(54) INTRACELLULAR ATP ENHANCER

(71) Applicants: School Juridical Person Higashi-Nippon-Gakuen, Hokkaido (JP); The University of Tokyo, Tokyo (JP); Nippon Chemiphar Co., Ltd., Tokyo (JP)

(72) Inventors: Miki Hiraoka, Ishikari-gun (JP); Ken Okamoto, Tokyo (JP); Masuharu Hirano, Misato (JP)

(73) Assignees: School Juridical Person Higashi-Nippon-Gakuen, Hokkaido (JP); The University of Tokyo, Tokyo (JP); Nippon Chemiphar Co., Ltd., Tokyo (JP)

( * ) Notice: Subject to any disclaimer, the term of this patent is extended or adjusted under 35 U.S.C. 154(b) by 572 days.

(21) Appl. No.: 18/256,138

(22) PCT Filed: Dec. 8, 2021

(86) PCT No.: PCT/JP2021/045045
§ 371 (c)(1),
(2) Date: Jun. 6, 2023

(87) PCT Pub. No.: WO2022/124325
PCT Pub. Date: Jun. 16, 2022

(65) Prior Publication Data

US 2024/0051971 A1 Feb. 15, 2024

(30) Foreign Application Priority Data

Dec. 8, 2020 (JP) ................................ 2020-203725

(51) Int. Cl.

| | |
|---|---|
| ***C07D 513/04*** | (2006.01) |
| ***A61K 9/48*** | (2006.01) |
| ***A61K 31/519*** | (2006.01) |
| ***A61K 31/5365*** | (2006.01) |
| ***A61K 31/542*** | (2006.01) |
| ***A61K 47/38*** | (2006.01) |
| ***A61P 17/00*** | (2006.01) |
| ***A61P 27/02*** | (2006.01) |
| ***C07D 487/04*** | (2006.01) |
| ***C07D 498/04*** | (2006.01) |

(52) U.S. Cl.
CPC .......... *C07D 513/04* (2013.01); *A61K 9/4866* (2013.01); *A61P 27/02* (2018.01)

(58) Field of Classification Search
CPC .. C07D 513/04; C07D 498/04; C07D 487/04; A61K 31/542; A61K 31/5365; A61K 31/519; A61K 9/4866; A61K 9/141; A61K 9/5047; A61K 47/38; A61P 27/02; A61P 17/00
See application file for complete search history.

(56) References Cited

U.S. PATENT DOCUMENTS

| | | | | |
|---|---|---|---|---|
| 4,871,742 | A | 10/1989 | Bonne et al. | |
| 10,413,546 | B2 * | 9/2019 | Nishino | A61K 31/519 |
| 2016/0038595 | A1 | 2/2016 | Davidoff | |

FOREIGN PATENT DOCUMENTS

| | | | |
|---|---|---|---|
| CN | 101282934 | A | 10/2008 |
| CN | 111405900 | A | 7/2020 |
| JP | 6153281 | B1 | 6/2017 |
| JP | 2018080135 | A | 5/2018 |
| JP | 2018087179 | A | 6/2018 |
| JP | 2018118914 | A | 8/2018 |
| JP | 2018135278 | A | 8/2018 |
| WO | 2007043457 | A1 | 4/2007 |
| WO | 2016136727 | A1 | 9/2016 |
| WO | 2017033963 | A1 | 3/2017 |
| WO | 2018092911 | A1 | 5/2018 |

(Continued)

OTHER PUBLICATIONS

English translation of claims of WO-2019208635-A1, https://translationportal.epo.org/emtp/translate/?ACTION=claims-retrieval&COUNTRY=WO&ENGINE=google&FORMAT=docdb&KIND=A1&LOCALE=en_EP&NUMBER=2019208635&OPS=ops.epo.org/3.2&SRCLANG=ja&TRGLANG=en, Retrieved on Jan. 22, 2026. (Year: 2026).*

(Continued)

*Primary Examiner* — Kamal A Saeed
*Assistant Examiner* — Sagar Patel
(74) *Attorney, Agent, or Firm* — Wood Herron & Evans LLP

(57) ABSTRACT

Provided is a pharmaceutical composition for enhancing intracellular ATP, including a compound represented by General Formula (I)

[Chemical Formula 1]

(I)

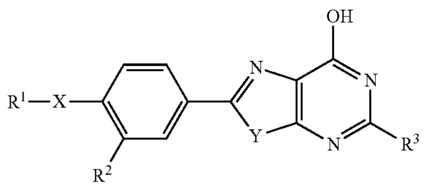

wherein $R^1$ represents an unsubstituted or substituted phenyl group, $R^2$ represents a cyano group or a nitro group, $R^3$ represents a hydrogen atom or a hydroxyl group, X represents an oxygen atom or —$S(O)_n$—, n represents an integer of 0 to 2, and Y represents an oxygen atom or a sulfur atom, or a pharmaceutically acceptable salt thereof.

24 Claims, 13 Drawing Sheets

(56) References Cited

FOREIGN PATENT DOCUMENTS

| | | | | | |
|---|---|---|---|---|---|
| WO | 2019107412 | A1 | | 6/2019 | |
| WO | WO-2019208635 | A1 | * | 10/2019 | .............. A61P 19/06 |
| WO | 2020246528 | A1 | | 12/2020 | |

OTHER PUBLICATIONS

English translation of description of WO-2019208635-A1, https://translationportal.epo.org/emtp/translate/?ACTION=description-retrieval&COUNTRY=WO&ENGINE=google&FORMAT=docdb&KIND=A1&LOCALE=en_EP&NUMBER=2019208635&OPS=ops.epo.org/3.2&SRCLANG=ja&TRGLANG=en, Retrieved on Jan. 22, 2026. (Year: 2026).*

PCT Office, International Search Report issued in PCT/JP2021/045045 dated Feb. 15, 2022.

Todd A. Johnson, et al., "Shortage of Cellular ATP as a Cause of Diseases and Strategies to Enhance ATP", Frontiers in Pharmacology, vol. 10, Article 98, Feb. 19, 2019, pp. 1-19.

Yuki Muraoka, et al., "KUS121, an ATP regulator, mitigates chorioretinal pathologies in animal models of age-related macular degeneration", Heliyon, vol. 4, No. 5, e00624, May 31, 2018, pp. 1-21.

Chinese Patent Office, Office Action issued in CN 202180082096.9 dated Mar. 14, 2025.

European Patent Office, Search Report issued in EP21903424.6 dated Oct. 8, 2024.

* cited by examiner

INTRACELLULAR ATP ENHANCER

TECHNICAL FIELD

The present invention relates to a pharmaceutical composition for enhancing intracellular ATP.

The present application claims priority based on Japanese Patent Application No. 2020-203725 filed in Japan on Dec. 8, 2020, the content of which is incorporated herein.

BACKGROUND ART

ATP (also referred to as adenosine triphosphate) is known to be an important substance involved in storage and supply of energy in a living body, and in a normal individual, the balance between production and consumption is maintained by high homeostasis, and the intracellular concentration is maintained in a certain range.

However, in certain diseases, disorders, or syndromes, it is known that the intracellular ATP concentration is lower than that in a normal state, and it is expected that increasing the intracellular ATP amount is effective for the treatment or prevention of the diseases, disorders, or syndromes.

A metabolic cycle is known in which ATP is converted into ADP (also referred to as adenosine diphosphate), AMP (also referred to as adenosine monophosphate), IMP (inosine monophosphate), inosine, hypoxanthine, xanthine, and uric acid in this order in a living body. It is known that there is a cycle (sometimes referred to as an intracellular purine salvage cycle) in which IMP is produced from hypoxanthine, and AMP, ADP, and ATP are further produced when the amount of hypoxanthine increases in the metabolic cycle.

It is known that a xanthine oxidoreductase (hereinafter, it may be abbreviated as XOR) inhibitory agent effective for treatment of gout inhibits XOR that acts on a conversion reaction from hypoxanthine to xanthine and a conversion reaction from xanthine to uric acid to reduce the production amount of uric acid in the metabolic cycle. Then, it is expected that the XOR inhibitory agent inhibits the conversion reaction from hypoxanthine to xanthine and further to uric acid, thereby accumulating intracellular hypoxanthine, and makes the intracellular purine salvage circuit function, thereby increasing the intracellular ATP amount.

Currently, examples of the XOR inhibitory agent used for the treatment of hyperuricemia include allopurinol and febuxostat. Patent Literatures 1 to 5 describe that XOR inhibitory agents such as allopurinol and febuxostat are effective for, for example, hemolytic anemia, sickle cell disease, pyruvate kinase deficiency, spherocytosis, elliptocytosis, stomatocytosis, thalassemia, ischemic heart disease, heart failure, cardiovascular disorder, hypertension, tachycardia, arrhythmia, chronic progressive external ophthalmoplegia syndrome, ragged-red fiber, myoclonic epilepsy syndrome, mitochondrial encephalomyopathy, lactic acidosis, stroke-like syndrome, Leigh encephalopathy, mitochondrial cardiomyopathy, Leber disease, mitochondrial diabetes, Pearson's disease, amyotrophic lateral sclerosis, Parkinson's disease, multiple sclerosis, adenylosuccinate lyase deficiency, Alzheimer-type dementia, dementia with Lewy body, frontotemporal dementia or the like. However, it is disclosed that the intracellular ATP enhancing action of allopurinol or febuxostat alone is not sufficient, and allopurinol or febuxostat needs to be used in combination with inosine, inosinic acid, hypoxanthine, or a salt thereof.

CITATION LIST

Patent Literature

Patent Literature 1: JP 6153281 B2
Patent Literature 2: JP 2018-80135 A
Patent Literature 3: WO 2018/092911 A
Patent Literature 4: JP 2018-118914 A
Patent Literature 5: JP 2018-135278 A

SUMMARY OF INVENTION

Technical Problem

The present inventors have studied medicines that enhance intracellular ATP, and found that there is still room for improvement in enhancement of intracellular ATP by medicines having an XOR inhibitory activity.

An object of the present invention is to provide a medicine that enhances intracellular ATP more effectively than conventionally known medicines. Another object of the present invention is to provide a medicine that has an XOR inhibitory activity and enhances intracellular ATP without use of inosine, inosinic acid, hypoxanthine, or a salt thereof in combination.

Solution to Problem

As a result of various studies on medicines having an XOR inhibitory activity, the present inventors have found that a pharmaceutical composition including a compound represented by General Formula (I) or a pharmaceutically acceptable salt thereof is effective as a medicine for enhancing intracellular ATP, and have completed the present invention.

That is, the present invention is as follows:

[1] A pharmaceutical composition for enhancing intracellular ATP, including: a compound represented by General Formula (I):

[Chemical Formula 1]

(I)

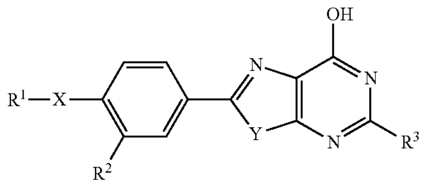

wherein $R^1$ represents an unsubstituted phenyl group or a phenyl group substituted with a substituent, the substituent represents at least one group selected from the group consisting of an alkyl group having 1 to 8 carbon atoms, an alkyl group having 1 to 8 carbon atoms substituted with a halogen atom, an alkoxy group having 1 to 8 carbon atoms, an alkoxycarbonyl group having 2 to 8 carbon atoms, a formyl group, a carboxyl group, a halogen atom, a phenyl group, and a phenoxy group, $R^2$ represents a cyano group or a nitro group, $R^3$ represents a hydrogen atom or a hydroxyl group, X represents an oxygen atom or $-S(O)_n-$, n represents an integer of 0 to 2, and Y represents an oxygen atom or a sulfur atom, or a pharmaceutically acceptable salt thereof.

[2] The pharmaceutical composition according to [1], wherein the intracellular ATP enhancing action is effected by an intracellular purine salvage cycle.

[3] The pharmaceutical composition according to claim 1 or 2, wherein the intracellular ATP enhancing action is sustained even in presence of an uncoupler.

[4] The pharmaceutical composition according to any one of [1] to [3], wherein the intracellular ATP enhancing action improves a state in which balance between production and consumption of ATP is tilted to a consumption side.

[5] The pharmaceutical composition according to any one of [1] to [4], wherein the intracellular ATP enhancing action is effected in hypoxic condition.

[6] The pharmaceutical composition according to any one of [1] to [5], wherein the intracellular ATP enhancing action is effected in absolute or relative deficiency of ATP.

[7] The pharmaceutical composition according to [6], wherein the absolute or relative deficiency of ATP is circulatory failure, abnormal protein accumulation, or a tissue disorder.

[8] The pharmaceutical composition according to any one of [1] to [7], which is for treatment or prevention of an ATP-related eye disease.

[9] The pharmaceutical composition according to [8], wherein the ATP-related eye disease is a disease that causes a retinal or optic nerve disorder;

[10] The pharmaceutical composition according to any one of [1] to [7], wherein the ATP-related eye disease is retinitis pigmentosa, cone-rod dystrophy, Oguchi disease, fundus albipunctatus, pigmented paravenous retinochoroidal atrophy, Leber congenital amaurosis, cone dystrophy, Stargardt disease, Best disease, familial exudative vitreoretinopathy, Wagner syndrome, Stickler syndrome, central areolar choroidal dystrophy, choroideremia, gyrus-like choroidal dystrophy, retinal degeneration secondary to uveitis, a retinal degenerative disease including a drug-induced (including chloroquine) retinal disorder, retinal vein occlusion, retinal artery occlusion, hypertensive retinopathy, diabetic retinopathy, renal retinopathy, age-related macular degeneration, central serous chorioretinopathy, retinal white spot syndrome, angioid streaks of the retina, rhegmatogenous retinal detachment involving the macula, macular hole, retinoschisis, exudative retinal detachment, proliferative vitreoretinopathy, retinal detachment associated with high myopia, Usher syndrome, Bardet-Biedl syndrome, Kearns-Sayre syndrome, Refsum syndrome, glaucoma, optic neuritis, ischemic optic neuropathy, compressive optic neuropathy, rhinogenous optic neuropathy, demyelinating optic neuropathy disease (including multiple sclerosis), or toxic optic neuropathy (including ethambutol, methanol, and thinner).

[11] The pharmaceutical composition according to any one of [1] to [10], which is used so that the compound represented by General Formula (I) or a pharmaceutically acceptable salt thereof is orally administered to a patient in need of enhancement of intracellular ATP at 10 to 320 mg per day, and if desired, the oral administration is continued for at least 7 days.

[12] The pharmaceutical composition according to any one of [1] to [11], in which R1 is an unsubstituted phenyl group or a phenyl group substituted with a halogen atom.

[13] The pharmaceutical composition according to any one of [1] to [12], in which X is an oxygen atom.

[14] The pharmaceutical composition according to any one of [1] to [13], in which X is a sulfur atom.

[15] The pharmaceutical composition according to any one of [1] to [14], in which the compound according to any one of [1] to [14] or a pharmaceutically acceptable salt thereof includes an amorphous substance thereof, and a content of the amorphous substance is 80 weight % or more with respect to the total weight of the compound according to any one of [1] to [14] or a pharmaceutically acceptable salt thereof.

[16] The pharmaceutical composition according to any one of [1] to [15], which is an enteric-coated preparation.

[17] The pharmaceutical composition according to [16], in which the enteric-coated preparation is a hard capsule.

[18] The pharmaceutical composition according to any one of [1] to [17], further including a solid dispersion containing a hypromellose derivative.

[19] The pharmaceutical composition according to [18], in which a weight ratio between the compound represented by General Formula (I) or a pharmaceutically acceptable salt thereof and the hypromellose derivative is 1:0.1 to 1:25.

[20] The pharmaceutical composition according to [18] or [19], in which the hypromellose derivative is hypromellose acetate succinate or hypromellose phthalate.

[21] The pharmaceutical composition according to any one of [1] to [20], which is a solid preparation.

[22] The pharmaceutical composition according to any one of [1] to [21], in which a content of the compound represented by General Formula (I) or a pharmaceutically acceptable salt thereof is 10 mg to 320 mg.

[23] The pharmaceutical composition according to any one of [1] to [22], in which a content of the compound represented by General Formula (I) or a pharmaceutically acceptable salt thereof per dosage unit is 10 mg to 320 mg.

[24] The pharmaceutical composition according to any one of [1] to [23], in which the content of the compound represented by General Formula (I) or a pharmaceutically acceptable salt thereof per dosage unit is 10 mg to 160 mg.

[25] The pharmaceutical composition according to any one of [1] to [24], in which the content of the compound represented by General Formula (I) or a pharmaceutically acceptable salt thereof per dosage unit is 10 mg to 80 mg.

[26] The pharmaceutical composition according to any one of [1] to [25], in which the content of the compound represented by General Formula (I) or a pharmaceutically acceptable salt thereof per dosage unit is 20 mg to 80 mg.

[27] The pharmaceutical composition according to any one of [1] to [26], in which a blood uric acid concentration is lowered by 0.5 to 2.0 mg/dL (for example, 0.5 to 1.5 mg/dL) 12 hours after administration on the first day of the administration as compared with a blood uric acid concentration before the administration.

[28] The pharmaceutical composition according to any one of [1] to [27], in which, by continuous administration once/day for 7 days, a blood uric acid concentration is lowered by 1.5 to 3.0 mg/dL (for example, 1.5 to 2.5 mg/dL) 12 hours after administration on the seventh day of the administration as compared with the blood uric acid concentration before the administration.

[29] The pharmaceutical composition according to any one of [1] to [28], in which a daily dose of the compound represented by General Formula (I) or a pharmaceutically acceptable salt thereof is not increased within 3 weeks of the administration after the start of the administration.

[30] The pharmaceutical composition according to any one of [1] to [29], in which the daily dose of the compound represented by General Formula (I) or a pharmaceutically acceptable salt thereof is not increased or is increased once within 7 weeks of the administration after the start of the administration.

[31] The pharmaceutical composition according to any one of [1] to [30], in which a maximum rate of decrease in a blood uric acid level on the first day of the administration ([(pre-administration uric acid level−minimum post-administration uric acid level on first day of administration)/pre-administration uric acid level]×100) is 10 to 25%.

[32] The pharmaceutical composition according to any one of [1] to [31], in which a maximum rate of decrease in a blood uric acid level on the seventh day of the administration ([(pre-administration uric acid level−minimum post-administration uric acid level on seventh day of administration)/pre-administration uric acid level]×100) is 20 to 45%.

[33] The pharmaceutical composition according to any one of [1] to [32], in which the compound represented by General Formula (I) or a pharmaceutically acceptable salt thereof is 2-(3-cyano-4-phenoxyphenyl)-7-hydroxythiazolo[5,4-d]pyrimidine or a pharmaceutically acceptable salt thereof.

[34] A package including the pharmaceutical composition according to any one of [1] to [33], in which the number of dosage units of the pharmaceutical composition in the package is the number required for continuous administration for 5 to 15 days.

[35] An enhancer of ATP, ADP, GTP, or GDP in a tissue, an organ, an internal organ, or a cell in which expression of a target enzyme XOR is substantially not observed or is small in a cell, including: an XOR inhibitor as an active ingredient.

[36] The enhancer according to [35], wherein the XOR inhibitor is a compound represented by the first term General Formula (I) or a pharmaceutically acceptable salt thereof, allopurinol, topiroxostat, or febuxostat.

[37] The enhancer according to [35] or [36], wherein the organ in which expression of a target enzyme XOR is substantially not observed or is small is an eyeball.

[38] The enhancer according to any one of [35] to [37], wherein the tissue in which expression of a target enzyme XOR is substantially not observed or is small is a retina.

[39] The enhancer according to any one of [35] to [37], wherein the tissue in which expression of a target enzyme XOR is substantially not observed or is small is an optic nerve.

[40] The enhancer according to any one of [35] to [39], further including an ATP precursor.

[41] The enhancer according to [40], wherein the ATP precursor is inosine and/or hypoxanthine.

[42] A therapeutic and/or preventive agent for an ATP-related disease in a tissue, an organ, an internal organ, or a cell in which expression of a target enzyme XOR is substantially not observed or is small in a cell, including: an XOR inhibitor as an active ingredient.

[43] The therapeutic and/or preventive agent according to [42], wherein the XOR inhibitor is a compound represented by the first term General Formula (I) or a pharmaceutically acceptable salt thereof, allopurinol, topiroxostat, or febuxostat.

[44] The therapeutic and/or preventive agent according to [42] or [43], wherein the organ in which expression of a target enzyme XOR is substantially not observed or is small is an eyeball.

[45] The therapeutic and/or preventive agent according to any one of [42] to [44], wherein the tissue in which expression of a target enzyme XOR is substantially not observed or is small is a retina.

[46] The therapeutic and/or preventive agent according to any one of [42] to [44], wherein the tissue in which expression of a target enzyme XOR is substantially not observed or is small is an optic nerve.

[47] The therapeutic and/or preventive agent according to any one of [42] to [46], wherein the ATP-related disease is an ATP-related eye disease.

[48] The therapeutic and/or preventive agent according to [47], wherein the ATP-related eye disease is retinitis pigmentosa, cone-rod dystrophy, Oguchi disease, fundus albipunctatus, pigmented paravenous retinochoroidal atrophy, Leber congenital amaurosis, cone dystrophy, Stargardt disease, Best disease, familial exudative vitreoretinopathy, Wagner syndrome, Stickler syndrome, central areolar choroidal dystrophy, choroideremia, gyrus-like choroidal dystrophy, retinal degeneration secondary to uveitis, a retinal degenerative disease including a drug-induced (including chloroquine) retinal disorder, retinal vein occlusion, retinal artery occlusion, hypertensive retinopathy, diabetic retinopathy, renal retinopathy, age-related macular degeneration, central serous chorioretinopathy, retinal white spot syndrome, angioid streaks of the retina, rhegmatogenous retinal detachment involving the macula, macular hole, retinoschisis, exudative retinal detachment, proliferative vitreoretinopathy, retinal detachment associated with high myopia, Usher syndrome, Bardet-Biedl syndrome, Kearns-Sayre syndrome, Refsum syndrome, glaucoma, optic neuritis, ischemic optic neuropathy, compressive optic neuropathy, rhinogenous optic neuropathy, demyelinating optic neuropathy disease (including multiple sclerosis), or toxic optic neuropathy (including ethambutol, methanol, and thinner).

[49] A pharmaceutical composition for treating and/or preventing an ATP-related disease in a tissue, an organ, an internal organ, or a cell in which expression of a target enzyme XOR is substantially not observed or is small in a cell, including: an XOR inhibitor as an active ingredient.

[50] The pharmaceutical composition according to [49], further including an ATP precursor.

[51] The pharmaceutical composition according to [50], wherein the ATP precursor is inosine and/or hypoxanthine.

[52] A pharmaceutical composition for treating and/or preventing an ATP-related disease, including an XOR inhibitor as an active ingredient.

[53] The pharmaceutical composition according to [52], wherein the XOR inhibitor is a compound represented by the first term General Formula (I) or a pharmaceutically acceptable salt thereof, allopurinol, topiroxostat, or febuxostat.

[54] The pharmaceutical composition according to [52] or [53], wherein the ATP-related disease is an ATP-related eye disease.

[55] The pharmaceutical composition according to [54], wherein the ATP-related eye disease is retinitis pigmentosa, cone-rod dystrophy, Oguchi disease, fundus albipunctatus, pigmented paravenous retinochoroidal atrophy, Leber congenital amaurosis, cone dystrophy, Stargardt disease, Best disease, familial exudative vitreoretinopathy, Wagner syndrome, Stickler syndrome, central areolar choroidal dystrophy, choroideremia, gyrus-like choroidal dystrophy, retinal degeneration secondary to uveitis, a retinal degenerative disease including a drug-induced (including chloroquine) retinal disorder, retinal vein occlusion, retinal artery occlusion, hypertensive retinopathy, diabetic retinopathy, renal retinopathy, age-related macular degeneration, central serous chorioretinopathy, retinal white spot syndrome, angioid streaks of the retina, rhegmatogenous retinal detachment involving the macula, macular hole, retinoschisis, exudative retinal detachment, proliferative vitreoretinopathy, retinal detachment associated with high myopia, Usher syndrome, Bardet-Biedl syndrome, Kearns-Sayre syndrome, Refsum syndrome, glaucoma, optic neuritis, ischemic optic neuropathy, compressive optic neuropathy, rhinogenous optic neuropathy, demyelinating optic neuropathy disease (including multiple sclerosis), or toxic optic neuropathy (including ethambutol, methanol, and thinner).

Advantageous Effects of Invention

The pharmaceutical composition provided by the present invention is useful as a pharmaceutical composition for enhancing intracellular ATP. In particular, the pharmaceutical composition provided by the present invention is useful as a pharmaceutical composition for enhancing intracellular ATP without use of inosine, inosinic acid, hypoxanthine, or a salt thereof in combination even when the pharmaceutical composition is a pharmaceutical composition including only a compound represented by General Formula (I) or a pharmaceutically acceptable salt thereof as an active ingredient. The pharmaceutical composition including an XOR inhibitor as an active ingredient provided by the present invention exhibits an ATP enhancing action even on a tissue, an organ, an internal organ, or a cell in which expression of a target enzyme XOR is substantially not observed or is small in a cell, and is also effective, for example, for ATP-related eye diseases.

DESCRIPTION OF EMBODIMENTS

<Pharmaceutical Composition>

Figure 1:
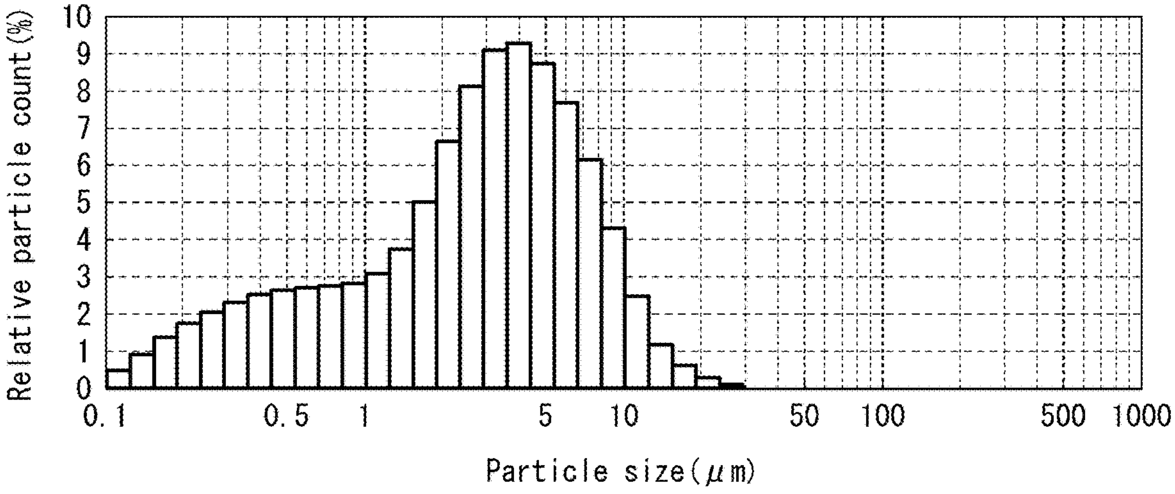
FIG. 1 is a diagram showing a particle size distribution of amorphous Compound 14 measured by a wet laser diffraction method.

The present invention will be described below in further detail. A pharmaceutical composition of the present invention for intracellular ATP enhancement includes a compound represented by General Formula (I) or a pharmaceutically acceptable salt thereof as an active ingredient.

In a compound represented by General Formula (I), R1 is an unsubstituted phenyl group or a phenyl group substituted with a substituent.

Examples of an "alkyl group having 1 to 8 carbon atoms" as a substituent in the phenyl group represented by R1 include a methyl group, an ethyl group, a propyl group, an isopropyl group, a butyl group, an isobutyl group, a tert-butyl group, a pentyl group, and a hexyl group, and a methyl group or an ethyl group is preferable.

Examples of an "alkyl group having 1 to 8 carbon atoms substituted with a halogen atom" as a substituent in the phenyl group represented by R1 include a fluoromethyl group, a trifluoromethyl group, a 1,1-difluoroethyl group, and a pentafluoroethyl group, and a fluoromethyl group or a trifluoromethyl group is preferable.

Examples of an "alkoxy group having 1 to 8 carbon atoms" as a substituent in the phenyl group represented by R1 include a methoxy group, an ethoxy group, a propoxy group, an isopropoxy group, a butoxy group, an isobutoxy group, and a tert-butoxy group, and a methoxy group is preferable.

Examples of an "alkoxycarbonyl group having 2 to 8 carbon atoms" as a substituent in the phenyl group represented by R1 include a methoxycarbonyl group, an ethoxycarbonyl group, a propoxycarbonyl group, a butoxycarbonyl group, and a tert-butoxycarbonyl group, and a methoxycarbonyl group or an ethoxycarbonyl group is preferable.

Examples of a "halogen atom" as a substituent in the phenyl group represented by R1 include a fluorine atom, a chlorine atom, a bromine atom, and an iodine atom, and a fluorine atom or a chlorine atom is preferable.

Regarding R1, an unsubstituted phenyl group is preferable.

In the compound represented by General Formula (I), R2 is a cyano group or a nitro group, and a cyano group is preferable.

In the compound represented by General Formula (I), R3 represents a hydrogen atom or a hydroxy group, and a hydrogen atom is preferable.

In the compound represented by General Formula (I), X is an oxygen atom or —S(O)n-, and an oxygen atom is preferable.

In the compound represented by General Formula (I), Y is an oxygen atom or a sulfur atom, and a sulfur atom is preferable.

Examples of the pharmaceutically acceptable salt of the compound represented by General Formula (I) include an alkali metal salt such as a sodium salt, a potassium salt, and a lithium salt, and a potassium salt is preferable.

The compound of General Formula (I) contained in the pharmaceutical composition for enhancing intracellular ATP according to one embodiment of the present invention can be obtained, for example, by the synthetic method described in WO 2005/121153 or WO 2019/208635.

Regarding the compound of General Formula (I) contained in the pharmaceutical composition for enhancing intracellular ATP of the present invention, examples of preferable compounds include the compounds in Table 1. In the Table, Me represents a methyl group.

TABLE 1

| | Structural formula | Compound name |
|---|---|---|
| Compound 1 | 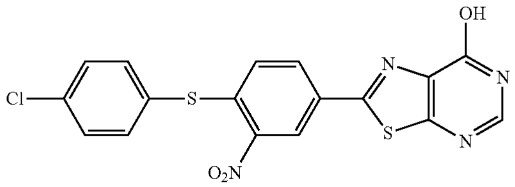 | 2-[4-(4-Chlorophenylthio)-3-nitrophenyl]-7-hydroxythiazolo[5,4-d]pyrimidine |
| Compound 2 | 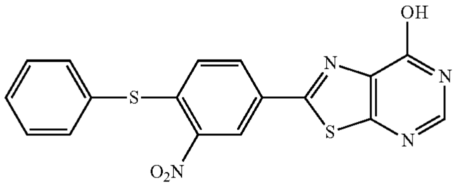 [SMILES: O=[N+]([O-])c1cc(-c2nc3c(O)ncnc3s2)ccc1Sc1ccccc1] | 7-Hydroxy-2-(3-nitro-4-phenylthiophenyl)thiazolo[5,4-d]pyrimidine |
| Compound 3 | 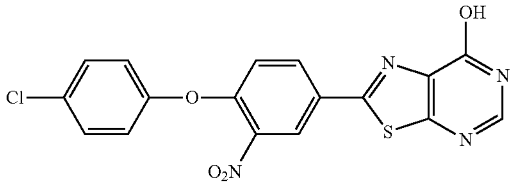 [SMILES: O=[N+]([O-])c1cc(-c2nc3c(O)ncnc3s2)ccc1Oc1ccc(Cl)cc1] | 2-[4-(4-Chlorophenoxy)-3-nitrophenyl]-7-hydroxythiazolo[5,4-d]pyrimidine |
| Compound 4 | 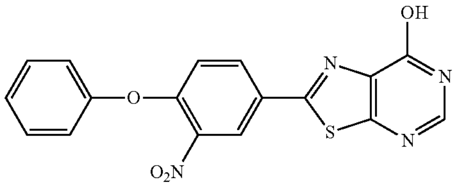 [SMILES: O=[N+]([O-])c1cc(-c2nc3c(O)ncnc3s2)ccc1Oc1ccccc1] | 7-Hydroxy-2-(3-nitro-4-phenoxyphenyl)thiazolo[5,4-d]pyrimidine |
| Compound 5 | 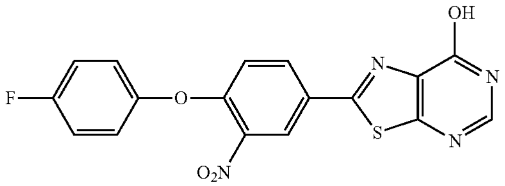 [SMILES: O=[N+]([O-])c1cc(-c2nc3c(O)ncnc3s2)ccc1Oc1ccc(F)cc1] | 2-[4-(4-Fluorophenoxy)-3-nitrophenyl]-7-hydroxythiazolo[5,4-d]pyrimidine |
| Compound 6 | 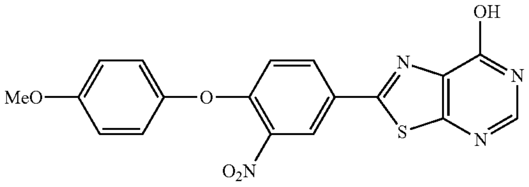 [SMILES: COc1ccc(Oc2ccc(-c3nc4c(O)ncnc4s3)cc2[N+](=O)[O-])cc1] | 2-[4-(4-Methoxyphenoxy)-3-nitrophenyl]-7-hydroxythiazolo[5,4-d]pyrimidine |

TABLE 1-continued

| | Structural formula | Compound name |
|---|---|---|
| Compound 7 | 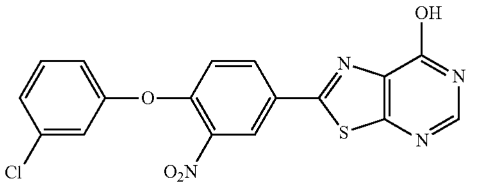 [SMILES: O=[N+]([O-])c1cc(-c2nc3c(O)ncnc3s2)ccc1Oc1cccc(Cl)c1] | 2-[4-(3-Chlorophenoxy)-3-nitrophenyl]-7-hydroxythiazolo[5,4-d]pyrimidine |
| Compound 8 | 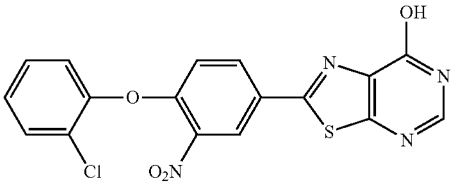 | 2-[4-(2-Chlorophenoxy)-3-nitrophenyl]-7-hydroxythiazolo[5,4-d]pyrimidine |
| Compound 9 | 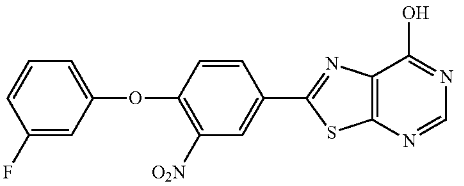 [SMILES: O=[N+]([O-])c1cc(-c2nc3c(O)ncnc3s2)ccc1Oc1cccc(F)c1] | 2-[4-(3-Fluorophenoxy)-3-nitrophenyl]-7-hydroxythiazolo[5,4-d]pyrimidine |
| Compound 10 | 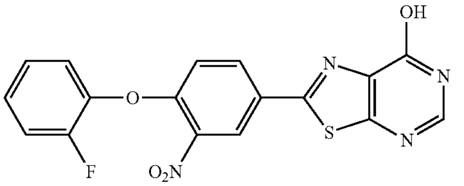 | 2-[4-(2-Fluorophenoxy)-3-nitrophenyl]-7-hydroxythiazolo[5,4-d]pyrimidine |
| Compound 11 | 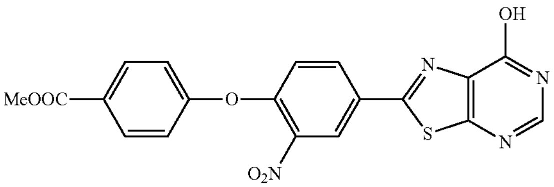 [SMILES: COC(=O)c1ccc(Oc2ccc(-c3nc4c(O)ncnc4s3)cc2[N+](=O)[O-])cc1] | 7-Hydroxy-2-[4-(4-methoxycarbonylphenoxy)-3-nitrophenyl]thiazolo[5,4-d]pyrimidine |
| Compound 12 | 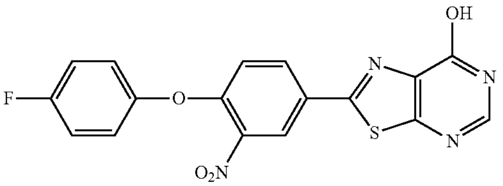 [SMILES: O=[N+]([O-])c1cc(-c2nc3c(O)ncnc3s2)ccc1Oc1ccc(F)cc1] | 2-[4-(4-Fluorophenoxy)-3-nitrophenyl]-7-hydroxyoxazolo[5,4-d]pyrimidine |
| Compound 13 | 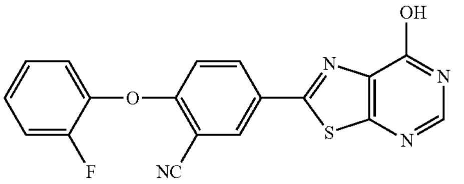 [SMILES: N#Cc1cc(-c2nc3c(O)ncnc3s2)ccc1Oc1ccccc1F] | 2-[3-Cyano-4-(2-fluorophenoxy)phenyl]-7-hydroxythiazolo[5,4-d]pyrimidine |
| Compound 14 | 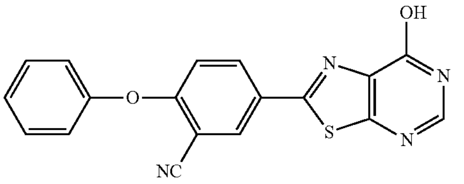 [SMILES: N#Cc1cc(-c2nc3c(O)ncnc3s2)ccc1Oc1ccccc1] | 2-(3-Cyano-4-phenoxyphenyl)-7-hydroxythiazolo[5,4-d]pyrimidine |

TABLE 1-continued

| | Structural formula | Compound name |
|---|---|---|
| Compound 15 | 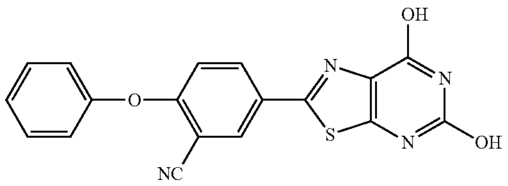 [SMILES: N#Cc1cc(-c2nc3c(O)nc(O)nc3s2)ccc1Oc1ccccc1] | 5-(5,7-Dihydroxythiazolo[5,4-d]pyrimidin-2-yl)-2-phenoxybenzonitrile |

Pharmaceutically acceptable salts may be formed from Compounds 1 to 15, and among these, Compounds 3 to 5, Compounds 8 to 10, Compound 13, Compound 14, or a pharmaceutically acceptable salt of these compounds is preferable.

It is preferable that the compound represented by General Formula (I) or a pharmaceutically acceptable salt thereof is partially or entirely amorphous in the pharmaceutical composition of the present invention for intracellular ATP enhancement. Here, the term "amorphous" means that a substance has a form having a short-distance order between atoms or molecules of the compound represented by General Formula (I) or a pharmaceutically acceptable salt thereof and having no long-distance order such as in crystals.

In the present invention, an amorphous state can be identified according to a halo peak shown in X-ray diffraction.

In the present invention, with respect to the total weight of the compound represented by General Formula (I) or a pharmaceutically acceptable salt thereof, an amorphous content is preferably 50 weight % or more, more preferably 80 weight % or more, still more preferably 90 weight % or more, and yet more preferably 95 weight % or more, and an amorphous content may be 100 weight %. Furthermore, the pharmaceutically acceptable salt of the compound represented by General Formula (I) may be crystalline, and in this case, with respect to the total weight, less than 50 weight % may be amorphous, 40 weight % or less may be amorphous, 30 weight % or less may be amorphous, 20 weight % or less may be amorphous, or 10 weight % may be amorphous, or the pharmaceutically acceptable salt of the compound represented by General Formula (I) may not be amorphous at all. The amorphous content can be obtained by an X-ray diffraction method. Regarding the amorphous content, the remainder is crystalline. That is, in the description of each content, the total of the amorphous content and the crystalline content is 100 weight %.

A method for producing the amorphous compound represented by General Formula (I) or a pharmaceutically acceptable salt thereof can be, for example, subjecting the compound represented by General Formula (I) or a pharmaceutically acceptable salt thereof to a spray-drying method. More specifically, the compound represented by General Formula (I) or a pharmaceutically acceptable salt thereof and optionally a pharmaceutically acceptable additive are added to a solvent described below to prepare a solution or a suspension, the solution or suspension is finely atomized by centrifugal spraying with a rotating disk or pressure spraying with a pressure nozzle, and the atomized solution or suspension is sprayed into a drying medium (for example, heated air or nitrogen gas), thereby obtaining a powdered amorphous dried component. In the spray-drying method, the temperature of the drying medium is, for example, 50 to 120° C., and preferably 50 to 90° C. The drying medium may be caused to flow in a certain direction, and can be caused to flow as an air flow, for example, at 0.1 to 0.6 $m^3$/min.

Examples of the solvent used in the spray-drying method include alcohols including alcohols having 1 to 6 carbon atoms such as methanol, ethanol, 1-propanol, 2-propanol, and tert-butyl alcohol, ethers such as tetrahydrofuran (THF), acetonitrile, and water, and these solvents can be used alone or as a mixed solvent of two or more kinds. Among these, ethanol, tetrahydrofuran, or a mixed solvent of these solvents and water is preferable.

Another method for producing the amorphous compound represented by General Formula (I) or a pharmaceutically acceptable salt thereof is a freeze-drying method. More specifically, the amorphous compound represented by General Formula (I) or a pharmaceutically acceptable salt thereof can also be produced by dissolving the compound represented by General Formula (I) or a pharmaceutically acceptable salt thereof in a solvent and then freeze-drying the solution.

Examples of the solvent used in the freeze-drying method include alcohols including alcohols having 1 to 6 carbon atoms such as methanol, ethanol, 1-propanol, 2-propanol, and tert-butyl alcohol; ethers such as tetrahydrofuran; nitriles such as acetonitrile; and water, and these solvents can be used alone or as a mixed solvent of two or more kinds.

A particle size of the amorphous compound represented by General Formula (I) or a pharmaceutically acceptable salt thereof is not particularly limited. From the viewpoints of the effect of the invention and formulation, the particle size may be, for example, 20 μm or less, and is preferably 1 to 15 μm, more preferably 1 to 10 μm, still more preferably 1.5 to 5 μm, and most preferably 2 to 5 μm, as the volume average particle size (D50).

The volume average particle size (D50) can generally be measured by dispersing a measurement sample in a solvent such as water and ethanol and measuring the particle size distribution by a laser diffraction method. The measurement sample may be dispersed in the solvent by irradiation with ultrasonic waves or the like. The particle size distribution can be measured by a particle size distribution measuring apparatus (for example, Shimadzu laser diffraction type particle size distribution measuring apparatus SALD-2200 or the like). The volume average particle size (D50) can be obtained from the obtained particle size distribution result. In addition, commercially available software (for example, Shimadzu WingSALD-2200 version 1.02 or the like) can be used for data collection and analysis.

A pharmaceutically acceptable additive can be added to the pharmaceutical composition of the present invention as necessary. For example, a required amount of a binding agent, a disintegrating agent, a diluting agent, a lubricant, or the like can be appropriately combined and added to the composition to produce the pharmaceutical composition of the present invention.

Examples of the binding agent include methyl cellulose, hydroxyethyl cellulose, hydroxypropyl cellulose, hypromellose, polyvinylpyrrolidone, gelatin, agar, alginic acid, sodium alginate, partially saponified polyvinyl alcohol, pullulan, partly pregelatinized starch, dextrin, xanthan gum, and gum arabic powder. These may be used alone or two or more types thereof may be used in combination. Among these, hydroxypropyl cellulose, hypromellose, and polyvinylpyrrolidone are preferable.

Examples of the disintegrating agent include crystalline cellulose, carboxymethyl cellulose (also referred to as carmellose), croscarmellose sodium, carboxymethyl cellulose calcium, low-substituted hydroxypropyl cellulose, crospovidone, hydroxypropyl starch, starch, partly pregelatinized starch, and sodium starch glycolate. These may be used alone or two or more types thereof may be used in combination. Among them, croscarmellose sodium, sodium starch glycolate, and crospovidone are preferable, and crospovidone is more preferable. The amount of the disintegrating agent added is, for example, preferably 5 to 30 weight % and more preferably 5 to 15 weight % with respect to the total weight of particles containing the active ingredient. Furthermore, in a case of being added in a tablet, the amount of the disintegrating agent added is preferably 1 to 10 weight % and more preferably 2 to 6 weight % with respect to the total weight of granules for tableting containing the active ingredient.

The diluting agent can be added in any of a kneading step, a granulation step, and a post-granulation end step for a pharmaceutical preparation. Examples of the diluting agent include celluloses such as crystalline cellulose, ethyl cellulose, hydroxypropyl cellulose, low-substituted hydroxypropyl cellulose, and hydroxypropyl methylcellulose (also referred to as hypromellose), starches such as corn starch, potato starch, wheat starch, rice starch, partly pregelatinized starch, and hydroxypropyl starch, sugars such as glucose, lactose, white sugar, refined white sugar, powdered sugar, trehalose, dextran, and dextrin, sugar alcohols such as D-mannitol, xylitol, sorbitol, and erythritol, glycerin fatty acid esters, and inorganic salts such as magnesium aluminometasilicate, synthetic hydrotalcite, anhydrous calcium phosphate, precipitated calcium carbonate, calcium silicate, dibasic calcium phosphate hydrate, and sodium hydrogen carbonate, and crystalline cellulose is preferable.

Examples of the lubricant include stearic acid, sodium stearyl fumarate, magnesium stearate, calcium stearate, sucrose fatty acid ester, polyethylene glycol, light anhydrous silicic acid, hardened oils, glycerin fatty acid esters, and a talc. These may be used alone or two or more types thereof may be used in combination. Among these, sodium stearyl fumarate, magnesium stearate, calcium stearate, and sucrose fatty acid esters are preferable.

Furthermore, recrystallization of the compound represented by General Formula (I) or a pharmaceutically acceptable salt thereof from a supersaturated solution can be suppressed by mixing the compound represented by General Formula (I) or a pharmaceutically acceptable salt thereof with an enteric polymer to be used in the pharmaceutical composition. It is preferable that the compound represented by General Formula (I) or a pharmaceutically acceptable salt thereof and the enteric polymer are uniformly mixed when subjected to mixing. Examples of a weight ratio between the compound represented by General Formula (I) or a pharmaceutically acceptable salt thereof and the enteric polymer can include 1:0.5 to 1:10, and the weight ratio is preferably 1:1 to 1:5, more preferably 1:2 to 1:5, and still more preferably 1:1 to 1:4.

Examples of the enteric polymer include the enteric polymer for coating, and a cellulose-based polymer is preferable, and hydroxypropyl methylcellulose, hydroxypropyl methylcellulose phthalate, and hydroxypropyl methylcellulose acetate succinate are more preferable.

Note that, when the compound represented by the general formula (I) or a pharmaceutically acceptable salt thereof is mixed with the enteric polymer, the pharmaceutically acceptable additive can be appropriately added.

<Enteric-Coated Preparation>

The pharmaceutical composition according to the present invention is preferably an enteric-coated preparation.

The "enteric-coated preparation" according to the present invention is a preparation designed to prevent degradation of the active ingredient in the stomach or to release the active ingredient mainly in the small intestine, not it in the stomach. The enteric-coated preparation itself is described in the Japanese Pharmacopoeia. As the enteric-coated preparation, dosage forms such as a tablet, a granular agent, fine granules, and a capsule are known. Examples of a production method for these dosage forms include (i) a method of producing enteric-coated granules by coating the active ingredient or the active ingredient and a pharmaceutically acceptable additive with the enteric polymer and obtaining a tablet, a granular agent, fine granules, or a capsule containing the enteric-coated granules, (ii) a method of producing a tablet, a granular agent, fine granules, or a capsule containing the active ingredient and a pharmaceutically acceptable additive and coating the preparation with the enteric polymer, and (iii) a method of encapsulating the active ingredient or the active ingredient and a pharmaceutically acceptable additive in a hard capsule formed of an enteric base.

That is, examples of the enteric-coated preparation according to the present invention include (i) a tablet, a granular agent, fine granules, or a capsule containing enteric-coated granules obtained by coating the active ingredient or the active ingredient and a pharmaceutically acceptable additive with the enteric polymer, (ii) a tablet, a granular agent, fine granules, or a capsule containing the active ingredient and a pharmaceutically acceptable additive and coated with the enteric polymer, and (iii) a hard capsule obtained by encapsulating the active ingredient or the active ingredient and a pharmaceutically acceptable additive in a hard capsule formed of an enteric base.

The enteric base refers to a base composed of an enteric polymer known per se, and examples of the enteric polymer include those presented below as enteric polymers for coating.

Examples of the enteric polymer for coating used in the present invention include an enteric methacrylic acid copolymer such as a methacrylic acid copolymer L and a methacrylic acid copolymer S (for example, Eudragit (registered trademark) L100 and Eudragit (registered trademark) S100, manufactured by Evonik Industries AG), a methacrylic acid copolymer LD (for example, Eudragit (registered trademark) L100-55 and Eudragit (registered trademark) L30D-55, manufactured by Evonik Industries AG), and a methyl acrylate/methyl methacrylate/methacrylic acid copolymer (for example, Eudragit (registered trademark) FS30D, manufactured by Evonik Industries AG), an enteric cellulose-based polymer such as hypromellose (also referred to as hydroxypropyl methylcellulose), hypromellose acetate succinate (manufactured by Shin-Etsu Chemical Co., Ltd., may be abbreviated as HPMCAS), hypromellose phthalate (manufactured by Shin-Etsu Chemical Co., Ltd., may be abbreviated as HPMCP), carboxymethyl ethylcellulose (manufactured by Freund Corporation, may be abbreviated as CMEC), and cellacefate (also referred to as cellulose acetate phthalate), and an enteric vinyl alcohol-based polymer such as polyvinyl alcohol acetate phthalate (manufactured by Colorcon, Inc.), and the enteric cellulose-based polymer is preferable. Among these, hydroxypropyl methylcellulose, hydroxypropyl methylcellulose phthalate, and hydroxypropyl methylcellulose acetate succinate are preferable.

The enteric-coated granules can be produced according to a known method. For example, the enteric-coated granules can be produced by producing granules by a fluidized granulation method such as rolling fluidized bed granulation and fluidized granulation, a rolling granulation method such as a centrifugal rolling granulation method, or a stirring granulation method, and then coating the granules with an enteric coating liquid and drying the granules.

The enteric coating liquid can be prepared by a method of adding the enteric polymer to a solvent and concentrating the solvent as necessary. Examples of the solvent used for preparing the enteric coating liquid include water, an alcohol-based solvent such as methanol and ethanol, and a mixed liquid thereof. A pharmaceutically acceptable additive such as a binding agent, a plasticizer, a coating base, a surfactant, and a diluting agent can be appropriately added as necessary. The amount of the solvent is not particularly limited, and the solvent can be used in an amount which is 3 to 10 times the total weight of the dissolved matter (that is, the total weight of the enteric polymer and the pharmaceutically acceptable additive).

The tablet, the granular agent, the fine granules, or the capsule containing the active ingredient and a pharmaceutically acceptable additive and coated with the enteric polymer can be produced by producing a tablet, a granular agent, fine granules, or a capsule containing the active ingredient and the pharmaceutically acceptable additive according to a known method, coating the obtained preparation with the enteric coating liquid, and drying the preparation.

As the hard capsule formed of the enteric base, a commercially available hard capsule can be used. For example, a hard capsule formed of an enteric base containing hydroxypropyl methylcellulose or hydroxypropyl methylcellulose acetate succinate can be used, and more specifically, Vcaps (registered trademark) Enteric (manufactured by Capsugel Belgium NV) or the like can be used.

A pharmaceutically acceptable additive can be added to the enteric-coated preparation according to the present invention as necessary. For example, a required amount of a binding agent, a disintegrating agent, a diluting agent, a lubricant, or the like can be appropriately combined and added to the enteric-coated preparation to produce the pharmaceutical composition of the present invention. Examples of the “pharmaceutically acceptable additive” can include those presented above as the pharmaceutically acceptable additives for the pharmaceutical composition.

The enteric-coated preparation provided by the present invention can exhibit high in vivo absorbability.

<Solid Dispersion>

The pharmaceutical composition of the present invention may be a pharmaceutical composition further including a solid dispersion containing a hypromellose derivative.

“A hypromellose derivative” according to the present invention represents hypromellose itself (may be abbreviated as HPMC), and an organic acid ester of hypromellose. Hypromellose is called hydroxypropyl methylcellulose, and is a mixed methyl group and hydroxypropyl group ether of cellulose. Examples of an organic acid forming an ester with hypromellose include acetic acid, succinic acid, and phthalic acid. Hypromellose according to the present invention may form an ester with one, two or more organic acids selected from among these organic acids.

Examples of the hypromellose derivative used in the present invention include hypromellose, hypromellose acetate succinate (may be abbreviated as HPMCAS), and hypromellose phthalate (may be abbreviated as HPMCP), and hypromellose acetate succinate or a hypromellose phthalate is preferable.

Examples of the hypromellose according to the present invention include hypromellose in which a substitution proportion per monomer unit is 28 to 30% for a methoxy group and 7 to 12% for a hydroxypropoxy group.

Examples of the hypromellose acetate succinate according to the present invention include hypromellose acetate succinates in which a substitution proportion per monomer unit is 20 to 26% and preferably 21 to 25% for a methoxy group, is 5 to 10% and preferably 5 to 9% for a hydroxypropoxyl group, is 5 to 14% and preferably 7 to 11% for an acetyl group, and is 4 to 18% and preferably 10 to 14% for a succinoyl group. Examples of the hypromellose phthalate according to the present invention include hypromellose phthalate in which a substitution proportion per monomer unit is 18 to 24% for a methoxy group, 5 to 10% for a hydroxypropoxy group, and 21 to 35% for a carboxybenzoyl group.

A content of a methoxy group, a hydroxypropoxy group, an acetyl group, a succinoyl group, a carboxybenzoyl group, or the like in the hypromellose derivative can be measured by a method according to a method of measuring a degree of substitution of hypromellose, hypromellose acetate succinate and hypromellose phthalate defined in the 17th revised Japanese Pharmacopoeia.

A viscosity of the hypromellose derivative according to the present invention is not particularly limited as long as the effect of the present invention is obtained, for example, 2.4 to 204 mPa·s, and preferably 2.4 to 3.6 mPa·s can be mentioned.

A viscosity of the hypromellose derivative according to the present invention can be measured by a method according to a method of measuring a viscosity of hypromellose, hypromellose acetate succinate, and hypromellose phthalate defined in the 17th revised Japanese Pharmacopoeia.

A weight ratio between the compound represented by General Formula (I) or a pharmaceutically acceptable salt thereof and the hypromellose derivative can be appropriately adjusted in a range of 1:0.1 to 1:25. The weight ratio between the compound represented by General Formula (I) or a pharmaceutically acceptable salt thereof and the hypromellose derivative is 1:0.1 to 1:10 in one example, 1:0.1 to 1:4 in another example, 1:1 to 1:10 in still another example, 1:2 to 1:5 in yet another example, and 1:3 to 1:4 in yet another example.

A solid dispersion having a weight ratio between 2-(3-cyano-4-phenoxyphenyl)-7-hydroxythiazolo[5,4-d]pyrimidine or a pharmaceutically acceptable salt thereof and the hypromellose derivative of 1:0.1 to 1:25 in one embodiment of the present invention, 1:0.1 to 1:10 in another embodiment, 1:0.1 to 1:4 in still another embodiment, 1:1 to 1:10 in yet another embodiment, 1:2 to 1:5 in yet another embodiment, and 1:3 to 1:4 in yet another embodiment, can be mentioned.

The term "solid dispersion" refers to a solid system containing at least two components, and a solid composition forming a system in which at least two components are uniformly mixed together. In addition, in the solid dispersion, at least one component is generally dispersed throughout the system.

Therefore, one embodiment of the "solid dispersion" according to the present invention is a solid composition which contains the compound represented by General Formula (I) or a pharmaceutically acceptable salt thereof and the hypromellose derivative, and forms a system in which the compound represented by General Formula (I) or a pharmaceutically acceptable salt thereof and the hypromellose derivative are uniformly mixed together.

Another embodiment of the "solid dispersion" according to the present invention is a solid composition forming a system in which the compound represented by General Formula (I) or a pharmaceutically acceptable salt thereof are dispersed throughout the hypromellose derivative. In this case, the compound represented by General Formula (I) or a pharmaceutically acceptable salt thereof forms a dispersed phase as a dispersoid, and the hypromellose derivative forms a continuous phase as a dispersion medium.

The "solid dispersion" according to the present invention is composed of the compound represented by General Formula (I) or a pharmaceutically acceptable salt thereof, the hypromellose derivative, and optionally a pharmaceutically acceptable additive. Examples of the pharmaceutically acceptable additive optionally contained include the additive selected from among a surfactant, a pH-adjusting agent, sugars and a plasticizer. These can be appropriately combined and added to the solid dispersion according to the present invention in required amounts.

Examples of the surfactant that can be used include a cationic surfactant such as sodium bis-(2-ethylhexyl)sulfosuccinate (sodium docusate), and an alkyltrimethylammonium bromide (for example, cetyltrimethylammonium bromide (cetrimide)), an anionic surfactant such as sodium lauryl sulfate, and a nonionic surfactant such as polyoxyethylene sorbitan (for example, Tween (Tween™ 20, 40, 60, 80 or 85)), and a sorbitan fatty acid ester (for example, Span™ 20, 40, 60, 80, or 85).

Examples of the pH-adjusting agent that can be used include an acid such as succinic acid, maleic acid, tartaric acid, citric acid, and aspartic acid, and an alkali such as sodium hydroxide, magnesium oxide, silicon dioxide, sodium hydrogen carbonate, and L-arginine.

Examples of the sugar that can be used include lactose, white sugar, glucose, fructose, sucrose, maltose (malt sugar), reduced maltose, maltitol, mannitol, erythritol, sorbitol, and xylitol.

Examples of the plasticizer that can be used include triethyl citrate, polyethylene glycol, and triacetin.

The "solid dispersion" according to the present invention may not contain the pharmaceutically acceptable additive. However, when the pharmaceutically acceptable additive is contained, for example, a weight ratio between the compound represented by General Formula (I) or a pharmaceutically acceptable salt thereof and the surfactant is 1:0.01 to 1:2, more preferably 1:0.02 to 1:1.5, and still more preferably 1:0.03 to 1:1.2, a weight ratio between the compound represented by General Formula (I) or a pharmaceutically acceptable salt thereof and the pH-adjusting agent is 1:0.01 to 1:2, more preferably 1:0.02 to 1:1.5, and still more preferably 1:0.03 to 1:1.2, a weight ratio between the compound represented by General Formula (I) or a pharmaceutically acceptable salt thereof and the sugar is 1:0.02 to 1:20, and more preferably 1:0.15 to 1:10, and a weight ratio between the compound represented by General Formula (I) or a pharmaceutically acceptable salt thereof and the plasticizer is 1:0.02 to 1:20, and more preferably 1:0.15 to 1:10.

In the "solid dispersion" according to the present invention, the pharmaceutically acceptable additive may constitute a dispersed phase or a continuous phase of the solid dispersion.

In the "solid dispersion" according to the present invention, it is preferable that a part or all of the compound represented by General Formula (I) or a pharmaceutically acceptable salt thereof be amorphous.

The solid dispersion according to the present invention can be produced by a method known per se. For example, a mixing and grinding method (a mechano-chemical method), a solvent method, a melting method, a hot melt extrusion method, and the like can be used for the production.

Here, in the mixing and grinding method, the compound represented by General Formula (I) or a pharmaceutically acceptable salt thereof and the hypromellose derivative, and optionally a pharmaceutically acceptable additive are mixed together, and a conventional method using a mixer and a grinding machine such as a ball mill and a hammer mill, can be then performed. The solvent method refers to a method in which the compound represented by General Formula (I) or a pharmaceutically acceptable salt thereof and the hypromellose derivative, and optionally a pharmaceutically acceptable additive are dissolved or suspended in a solvent (an organic solvent, water or a mixed solution thereof), and the solvent is then removed to precipitate a solid dispersion or a solid dispersion is precipitated in the solvent.

The solvent can be removed by a method such as spray methods (can be classified into a fluid bed method, a blowing drying method (also called a spray dry method), a rolling layer method, a stirring method, a supercritical method or the like according to an embodiment), a filtration method, an evaporation method, a freeze-drying method, or the like. A spray method is preferable, and a spray-drying method is particularly preferable among these methods.

Regarding the solvent that can be used to produce the solid dispersion according to the present invention, a pharmaceutically acceptable solvent is preferable. For example, ethanol, methanol, 2-propanol, acetone, 2-butanone, methyl isobutyl ketone, tetrahydrofuran (THF), tetrahydropyran, 1,4-dioxane, diethyl ether, toluene, acetonitrile, methylene chloride, chloroform, methyl acetate, ethyl acetate, butyl acetate, acetic acid, formic acid, N,N-dimethylformamide, N,N-dimethylacetamide, and dimethyl sulfoxide may be used.

It is preferable that the compound represented by General Formula (I) or a pharmaceutically acceptable salt thereof and a pharmaceutically acceptable additive optionally added dissolve in such a solvent.

In the spray-drying method, the solid dispersion can be produced by a method known per se. For example, the compound represented by General Formula (I) or a pharmaceutically acceptable salt thereof and the hypromellose derivative, and optionally a pharmaceutically acceptable additive may be added to the solvent to prepare a solution or suspension, the solution or suspension may be formed into a fine mist by centrifugal spraying using a rotating disk or pressure spraying using a pressure nozzle, and this may be sprayed into a drying medium (heated air or nitrogen gas), and thereby a solid dispersion can be obtained as a powdered dried component.

In the spray-drying method, the temperature of the drying medium is, for example, 50 to 120° C., and preferably 50 to 90° C. The drying medium may be caused to flow in a certain direction, and can be caused to flow as an air flow, for example, at 0.1 to 0.6 $m^3$/min.

The precipitation method in the solvent methods is preferably a coprecipitation method, and the compound represented by General Formula (I) or a pharmaceutically acceptable salt thereof and the hypromellose derivative, and optionally a pharmaceutically acceptable additive are dissolved or suspended in a solvent, the dissolved compound (I) or the pharmaceutically acceptable salt, and the hypromellose derivative, and the pharmaceutically acceptable additive optionally added are precipitated by lowering the dissolution concentration by addition of an insoluble solvent, lowering a temperature, or the like, and thereby a solid dispersion can be obtained.

The melting method is a method in which the compound represented by General Formula (I) or a pharmaceutically acceptable salt thereof and the hypromellose derivative, and optionally a pharmaceutically acceptable additive are heated to the melting point or the softening point of hypromellose derivatives or higher and stirred, and thus the compound represented by General Formula (I) or the pharmaceutically acceptable salt thereof and the pharmaceutically acceptable additive optionally added are dissolved or dispersed in the hypromellose derivative and then rapidly cooled. In this case, optionally an additive, for example, a plasticizer such as triethyl citrate, polyethylene glycol, and triacetin, and a surfactant can be additionally added. The production can be performed using a stirring granulator having a heating device.

The hot melt extrusion method is a method in which the compound represented by General Formula (I) or a pharmaceutically acceptable salt thereof and the hypromellose derivative, and optionally a pharmaceutically acceptable additive are heated and mixed under pressure using an extruder having a heating device, for example, a 2-screw extruder, and thereby a solid dispersion is obtained. The obtained plastic-like solid dispersion can be ground using a grinding machine to obtain a solid dispersion powder.

The solid dispersion according to the present invention produced according to the above production method can be formed into solid dispersion particles having a certain particle size by a known method, and the solid dispersion particles can be directly used as a powder or a granular agent.

A pharmaceutical composition containing the solid dispersion according to the present invention contains the solid dispersion and a pharmaceutically acceptable additive. Regarding the pharmaceutically acceptable additive, for example, a binding agent, a disintegrating agent, a diluting agent, a lubricant, and the like are appropriately combined and added in required amounts, and thereby a pharmaceutical composition of the present invention can be produced. Examples of the "pharmaceutically acceptable additive" can include those presented above as the pharmaceutically acceptable additives for the pharmaceutical composition.

The pharmaceutical composition containing the solid dispersion according to the present invention is subjected to a formulation process known per se and formulated into and provided as a solid preparation such as a tablet, a capsule, a granular agent, and a powder or a liquid preparation such as an injection product. Here, regarding the injection product, the pharmaceutical composition of the present invention may be provided as a solid preparation, put into the injection product for use, and used.

Since the present invention has an effect of preventing tableting failures, it is particularly preferable when the solid preparation has a tablet form. In addition, such a solid preparation can be optionally coated.

A content of a solid dispersion in the pharmaceutical composition according to the present invention including a solid dispersion may be 10 to 95% by weight, preferably 30 to 90% by weight, and more preferably 60 to 85% by weight based on a total weight of the pharmaceutical composition.

The solid dispersion provided by the present invention can exhibit high absorbability and storage stability in a living body.

The pharmaceutical composition according to the present invention can be produced as a medicine in an appropriate dosage form such as a tablet, a capsule, a granule, a powder, an eye drop, a gargle, an ointment, a cream, a gel, a poultice, a patch, a liniment, a tape, a cataplasm, an injection, or a suppository according to usual methods in the technical field of preparations.

Among the preparations described above, for example, the ointment can be produced by a formulation known per se. For example, the ointment can be produced by triturating or melting one or more active ingredients in a base. The ointment base is selected from ointment bases known per se. For example, one or more bases selected from higher fatty acids or higher fatty acid esters (for example, adipic acid, myristic acid, palmitic acid, stearic acid, oleic acid, adipic acid ester, myristic acid ester, palmitic acid ester, stearic acid ester, and oleic acid ester), waxes (for example, beeswax, spermaceti, and ceresin), surfactants (for example, polyoxyethylene alkyl ether phosphoric acid ester), higher alcohols (for example, cetanol, stearyl alcohol, and cetostearyl alcohol), silicone oils (for example, dimethylpolysiloxane), hydrocarbons (for example, hydrophilic petrolatum, white petrolatum, purified lanolin, and liquid paraffin), glycols (for example, ethylene glycol, diethylene glycol, propylene glycol, polyethylene glycol, and macrogol), plant oils (for example, castor oil, olive oil, sesame oil, and turpentine oil), animal oils (for example, mink oil, egg-yolk oil, squalane, and squalene), water, absorption promoters, and irritation preventing agents can be mixed and used. The ointment can further contain a moisturizing agent, a preservative, a stabilizing agent, an antioxidant, a fragrance or the like.

The pharmaceutical composition provided by the present invention can be orally or parenterally administered to a patient in need of enhancement of intracellular ATP, more specifically, a human or other mammals suffering from or at risk of suffering from an ATP-related eye disease. In the present invention, the "ATP-related eye disease" means a disease that can be treated or prevented by increasing the ATP concentration in the eyeball. Examples of such a disease include diseases that cause disorders of the retina or the optic nerve. Examples of the disorders of the retina include retinal degenerative diseases including retinal dystrophy (retinitis pigmentosa, cone-rod dystrophy, Oguchi disease, fundus albipunctatus, pigmented paravenous retinochoroidal atrophy, Leber congenital amaurosis and the like), macular dystrophy (cone dystrophy, Stargardt disease, Best disease and the like), vitreoretinal dystrophy (familial exudative vitreoretinopathy, Wagner syndrome, Stickler syndrome and the like), choroidal dystrophy (central areolar choroidal dystrophy, choroideremia, gyrus-like choroidal dystrophy and the like), retinal degeneration secondary to uveitis, and a drug-induced (chloroquine and the like) retinal disorder; retinal disorders associated with impaired retinal blood flow (retinal vein occlusion, retinal artery occlusion, hypertensive retinopathy, diabetic retinopathy, renal retinopathy and the like); retinal pigment epithelium disorders (age-related macular degeneration, central serous chorioretinopathy, retinal white spot syndrome, angioid streaks of the retina and the like); and retinal disorders associated with detachment of the retina (rhegmatogenous retinal detachment involving the macula, macular hole, retinoschisis, exudative retinal detachment, proliferative vitreoretinopathy, retinal detachment associated with high myopia and the like), and examples of the disorders of the optic nerve include glaucoma, optic neuritis, ischemic optic neuropathy, compressive optic neuropathy, rhinogenous optic neuropathy, demyelinating diseases (represented by multiple sclerosis), and toxic optic neuropathy (ethambutol, methanol, thinner and the like). Examples thereof further include retinitis pigmentosa associated with Usher syndrome with hearing loss, retinitis pigmentosa associated with Bardet-Biedl syndrome with polydactyly, obesity, diabetes, and renal malformation, retinitis pigmentosa associated with Kearns-Sayre syndrome complicating blepharoptosis and eyeball movement disorder, and retinitis pigmentosa associated with Refsum syndrome or the like complicating multiple optic neuritis and cerebellar ataxia. The administration method can be appropriately selected for each disease. For example, for ATP-related eye diseases, for example, a tablet is preferably orally administered, but the administration method is not limited thereto. This is because, in the present invention, it has become clear that when an XOR inhibitory agent is orally administered, the amount of hypoxanthine or inosine increases in a living body, the hypoxanthine or inosine passes through the blood-retinal barrier, and the hypoxanthine or inosine increases ATP in the eyeball. Preferably, the pharmaceutical composition provided by the present invention is administered to a human. The pharmaceutical composition provided by the present invention is useful as a pharmaceutical composition for enhancing intracellular ATP.

One embodiment of the present invention is a pharmaceutical composition for enhancing intracellular ATP including enteric-coated granules in which a compound represented by General Formula (I) or a pharmaceutically acceptable salt thereof is coated with an enteric polymer, which is used so that the compound represented by General Formula (I) or a pharmaceutically acceptable salt thereof is orally administered to a patient in need of enhancement of intracellular ATP at 10 to 320 mg, preferably 20 to 320 mg, more preferably 40 to 280 mg, more preferably 40 to 240 mg, more preferably 40 to 180 mg, more preferably 60 to 140 mg, and further preferably 60 to 120 mg per day, and if desired, the oral administration is continued for at least 7 days.

Another embodiment of the present invention is a tablet, a granule, a fine granule, or a capsule for enhancing intracellular ATP including enteric-coated granules in which a compound represented by General Formula (I) or a pharmaceutically acceptable salt thereof is coated with an enteric polymer, which is used so that the compound represented by General Formula (I) or a pharmaceutically acceptable salt thereof is orally administered to a patient in need of enhancement of intracellular ATP at 10 to 320 mg, preferably 20 to 320 mg, more preferably 40 to 280 mg, more preferably 40 to 240 mg, more preferably 40 to 180 mg, more preferably 60 to 140 mg, and further preferably 60 to 120 mg per day, and if desired, the oral administration is continued for at least 7 days.

Another embodiment of the present invention is a pharmaceutical composition for enhancing intracellular ATP that includes enteric-coated granules in which a compound represented by General Formula (I) or a pharmaceutically acceptable salt thereof is coated with an enteric polymer and in which the compound represented by General Formula (I) or a pharmaceutically acceptable salt thereof in the enteric-coated granules is further mixed with the enteric polymer if desired, which is used so that the compound represented by General Formula (I) or a pharmaceutically acceptable salt thereof is orally administered to a patient in need of enhancement of intracellular ATP at 10 to 320 mg, preferably 20 to 320 mg, more preferably 40 to 280 mg, more preferably 40 to 240 mg, more preferably 40 to 180 mg, more preferably 60 to 140 mg, and further preferably 60 to 120 mg per day, and if desired, the oral administration is continued for at least 7 days.

Another embodiment of the present invention is a tablet, a granule, a fine granule, or a capsule for enhancing intracellular ATP that includes enteric-coated granules in which a compound represented by General Formula (I) or a pharmaceutically acceptable salt thereof is coated with an enteric polymer and in which the compound represented by General Formula (I) or a pharmaceutically acceptable salt thereof in the enteric-coated granules is further mixed with the enteric polymer if desired, which is used so that the compound represented by General Formula (I) or a pharmaceutically acceptable salt thereof is orally administered to a patient in need of enhancement of intracellular ATP at 10 to 320 mg, preferably 20 to 320 mg, more preferably 40 to 280 mg, more preferably 40 to 240 mg, more preferably 40 to 180 mg, more preferably 60 to 140 mg, and further preferably 60 to 120 mg per day, and if desired, the oral administration is continued for at least 7 days.

Another embodiment of the present invention is a pharmaceutical composition for enhancing intracellular ATP including enteric-coated granules in which a compound represented by General Formula (I) or a pharmaceutically acceptable salt thereof and a pharmaceutically acceptable additive are coated with an enteric polymer, which is used so that the compound represented by General Formula (I) or a pharmaceutically acceptable salt thereof is orally administered to a patient in need of enhancement of intracellular ATP at 10 to 320 mg, preferably 20 to 320 mg, more preferably 40 to 280 mg, more preferably 40 to 240 mg, more preferably 40 to 180 mg, more preferably 60 to 140 mg, and further preferably 60 to 120 mg per day, and if desired, the oral administration is continued for at least 7 days.

Another embodiment of the present invention is a tablet, a granule, a fine granule, or a capsule for enhancing intracellular ATP including enteric-coated granules in which a compound represented by General Formula (I) or a pharmaceutically acceptable salt thereof and a pharmaceutically acceptable additive are coated with an enteric polymer, which is used so that the compound represented by General Formula (I) or a pharmaceutically acceptable salt thereof is orally administered to a patient in need of enhancement of intracellular ATP at 10 to 320 mg, preferably 20 to 320 mg, more preferably 40 to 280 mg, more preferably 40 to 240 mg, more preferably 40 to 180 mg, more preferably 60 to 140 mg, and further preferably 60 to 120 mg per day, and if desired, the oral administration is continued for at least 7 days.

Another embodiment of the present invention is a pharmaceutical composition for enhancing intracellular ATP that includes enteric-coated granules in which a compound represented by General Formula (I) or a pharmaceutically acceptable salt thereof and a pharmaceutically acceptable additive are coated with an enteric polymer and in which the compound represented by General Formula (I) or a pharmaceutically acceptable salt thereof and the pharmaceutically acceptable additive in the enteric-coated granules are further mixed with the enteric polymer, which is used so that the compound represented by General Formula (I) or a pharmaceutically acceptable salt thereof is orally administered to a patient in need of enhancement of intracellular ATP at 10 to 320 mg, preferably 20 to 320 mg, more preferably 40 to 280 mg, more preferably 40 to 240 mg, more preferably 40 to 180 mg, more preferably 60 to 140 mg, and further preferably 60 to 120 mg per day, and if desired, the oral administration is continued for at least 7 days.

Another embodiment of the present invention is a tablet, a granule, a fine granule, or a capsule for enhancing intracellular ATP that includes enteric-coated granules in which a compound represented by General Formula (I) or a pharmaceutically acceptable salt thereof and a pharmaceutically acceptable additive are coated with an enteric polymer and in which the compound represented by General Formula (I) or a pharmaceutically acceptable salt thereof and the pharmaceutically acceptable additive in the enteric-coated granules are further mixed with the enteric polymer, which is used so that the compound represented by General Formula (I) or a pharmaceutically acceptable salt thereof is orally administered to a patient in need of enhancement of intracellular ATP at 10 to 320 mg, preferably 20 to 320 mg, more preferably 40 to 280 mg, more preferably 40 to 240 mg, more preferably 40 to 180 mg, more preferably 60 to 140 mg, and further preferably 60 to 120 mg per day, and if desired, the oral administration is continued for at least 7 days.

Another embodiment of the present invention is a pharmaceutical composition for enhancing intracellular ATP including a compound represented by General Formula (I) or a pharmaceutically acceptable salt thereof and a pharmaceutically acceptable additive that are coated with an enteric polymer, which is used so that the compound represented by General Formula (I) or a pharmaceutically acceptable salt thereof is orally administered to a patient in need of enhancement of intracellular ATP at 10 to 320 mg, preferably 20 to 320 mg, more preferably 40 to 280 mg, more preferably 40 to 240 mg, more preferably 40 to 180 mg, more preferably 60 to 140 mg, and further preferably 60 to 120 mg per day, and if desired, the oral administration is continued for at least 7 days.

Another embodiment of the present invention is a tablet, a granule, a fine granule, or a capsule for enhancing intracellular ATP including a compound represented by General Formula (I) or a pharmaceutically acceptable salt thereof and a pharmaceutically acceptable additive that are coated with an enteric polymer, which is used so that the compound represented by General Formula (I) or a pharmaceutically acceptable salt thereof is orally administered to a patient in need of enhancement of intracellular ATP at 10 to 320 mg, preferably 20 to 320 mg, more preferably 40 to 280 mg, more preferably 40 to 240 mg, more preferably 40 to 180 mg, more preferably 60 to 140 mg, and further preferably 60 to 120 mg per day, and if desired, the oral administration is continued for at least 7 days.

Another embodiment of the present invention is a pharmaceutical composition for enhancing intracellular ATP that includes a compound represented by General Formula (I) or a pharmaceutically acceptable salt thereof and a pharmaceutically acceptable additive that are coated with an enteric polymer and in which the compound represented by General Formula (I) or a pharmaceutically acceptable salt thereof and the pharmaceutically acceptable additive are further mixed with the enteric polymer, which is used so that the compound represented by General Formula (I) or a pharmaceutically acceptable salt thereof is orally administered to a patient in need of enhancement of intracellular ATP at 10 to 320 mg, preferably 20 to 320 mg, more preferably 40 to 280 mg, more preferably 40 to 240 mg, more preferably 40 to 180 mg, more preferably 60 to 140 mg, and further preferably 60 to 120 mg per day, and if desired, the oral administration is continued for at least 7 days.

Another embodiment of the present invention is a tablet, a granule, a fine granule, or a capsule for enhancing intracellular ATP that includes a compound represented by General Formula (I) or a pharmaceutically acceptable salt thereof and a pharmaceutically acceptable additive that are coated with an enteric polymer and in which the compound represented by General Formula (I) or a pharmaceutically acceptable salt thereof and the pharmaceutically acceptable additive are further mixed with the enteric polymer, which is used so that the compound represented by General Formula (I) or a pharmaceutically acceptable salt thereof is orally administered to a patient in need of enhancement of intracellular ATP at 10 to 320 mg, preferably 20 to 320 mg, more preferably 40 to 280 mg, more preferably 40 to 240 mg, more preferably 40 to 180 mg, more preferably 60 to 140 mg, and further preferably 60 to 120 mg per day, and if desired, the oral administration is continued for at least 7 days.

Another embodiment of the present invention is a hard capsule preparation for enhancing intracellular ATP in which a compound represented by General Formula (I) or a pharmaceutically acceptable salt thereof is encapsulated in a hard capsule composed of an enteric base, which is used so that the compound represented by General Formula (I) or a pharmaceutically acceptable salt thereof is orally administered to a patient in need of enhancement of intracellular ATP at 10 to 320 mg, preferably 20 to 320 mg, more preferably 40 to 280 mg, more preferably 40 to 240 mg, more preferably 40 to 180 mg, more preferably 60 to 140 mg, and further preferably 60 to 120 mg per day, and if desired, the oral administration is continued for at least 7 days.

Another embodiment of the present invention is a hard capsule preparation for enhancing intracellular ATP in which a compound represented by General Formula (I) or a pharmaceutically acceptable salt thereof and a pharmaceutically acceptable additive are encapsulated in a hard capsule composed of an enteric base, which is used so that the compound represented by General Formula (I) or a pharmaceutically acceptable salt thereof is orally administered to a patient in need of enhancement of intracellular ATP at 10 to 320 mg, preferably 20 to 320 mg, more preferably 40 to 280 mg, more preferably 40 to 240 mg, more preferably 40 to 180 mg, more preferably 60 to 140 mg, and further preferably 60 to 120 mg per day, and if desired, the oral administration is continued for at least 7 days. Another embodiment of the present invention is a hard capsule preparation for enhancing intracellular ATP in which a compound represented by General Formula (I) or a pharmaceutically acceptable salt thereof is encapsulated in a hard capsule composed of an enteric base and the compound represented by General Formula (I) or a pharmaceutically acceptable salt thereof is further mixed with an enteric polymer, which is used so that the compound represented by General Formula (I) or a pharmaceutically acceptable salt thereof is orally administered to a patient in need of enhancement of intracellular ATP at 10 to 320 mg, preferably 20 to 320 mg, more preferably 40 to 280 mg, more preferably 40 to 240 mg, more preferably 40 to 180 mg, more preferably 60 to 140 mg, and further preferably 60 to 120 mg per day, and if desired, the oral administration is continued for at least 7 days.

Another embodiment of the present invention is a hard capsule preparation for enhancing intracellular ATP in which a compound represented by General Formula (I) or a pharmaceutically acceptable salt thereof and a pharmaceutically acceptable additive are encapsulated in a hard capsule composed of an enteric base and the compound represented by General Formula (I) or a pharmaceutically acceptable salt thereof and the pharmaceutically acceptable additive are further mixed with an enteric polymer, which is used so that the compound represented by General Formula (I) or a pharmaceutically acceptable salt thereof is orally administered to a patient in need of enhancement of intracellular ATP at 10 to 320 mg, preferably 20 to 320 mg, more preferably 40 to 280 mg, more preferably 40 to 240 mg, more preferably 40 to 180 mg, more preferably 60 to 140 mg, and further preferably 60 to 120 mg per day, and if desired, the oral administration is continued for at least 7 days.

Another embodiment of the present invention is a compound represented by General Formula (I) or a pharmaceutically acceptable salt thereof for use in enhancing intracellular ATP, which is used so that the compound represented by General Formula (I) or a pharmaceutically acceptable salt thereof is orally administered to a patient in need of enhancement of intracellular ATP at 10 to 320 mg, preferably 20 to 320 mg, more preferably 40 to 280 mg, more preferably 40 to 240 mg, more preferably 40 to 180 mg, more preferably 60 to 140 mg, and further preferably 60 to 120 mg per day, and if desired, the oral administration is continued for at least 7 days.

Another embodiment of the present invention is a pharmaceutical composition including a compound represented by General Formula (I) or a pharmaceutically acceptable salt thereof and a pharmaceutically acceptable additive for use in enhancing intracellular ATP which is used so that the compound represented by General Formula (I) or a pharmaceutically acceptable salt thereof is orally administered to a patient in need of enhancement of intracellular ATP at 10 to 320 mg, preferably 20 to 320 mg, more preferably 40 to 280 mg, more preferably 40 to 240 mg, more preferably 40 to 180 mg, more preferably 60 to 140 mg, and further preferably 60 to 120 mg per day, and if desired, the oral administration is continued for at least 7 days.

Another embodiment of the present invention is a solid dispersion according to the present invention or a pharmaceutical composition including the solid dispersion for use in enhancing intracellular ATP, which is used so that the compound represented by General Formula (I) or a pharmaceutically acceptable salt thereof is orally administered to a patient in need of enhancement of intracellular ATP at 10 to 320 mg, preferably 20 to 320 mg, more preferably 40 to 280 mg, more preferably 40 to 240 mg, more preferably 40 to 180 mg, more preferably 60 to 140 mg, and further preferably 60 to 120 mg per day, and if desired, the oral administration is continued for at least 7 days.

Another embodiment of the present invention is use of a compound represented by General Formula (I) or a pharmaceutically acceptable salt thereof for production of a pharmaceutical composition for enhancing intracellular ATP, which is used so that the compound represented by General Formula (I) or a pharmaceutically acceptable salt thereof is orally administered to a patient in need of enhancement of intracellular ATP at 10 to 320 mg, preferably 20 to 320 mg, more preferably 40 to 280 mg, more preferably 40 to 240 mg, more preferably 40 to 180 mg, more preferably 60 to 140 mg, and further preferably 60 to 120 mg per day, and if desired, the oral administration is continued for at least 7 days.

Another embodiment of the present invention is a method for enhancing intracellular ATP, including the step of: orally administering the pharmaceutical composition of the present invention to a subject in need of enhancement of intracellular ATP at 10 to 320 mg, preferably 20 to 320 mg, more preferably 40 to 280 mg, more preferably 40 to 240 mg, more preferably 40 to 180 mg, more preferably 60 to 140 mg, and further preferably 60 to 120 mg per day, and if desired, continuing the oral administration for at least 7 days.

Yet another embodiment of the present invention is a method for enhancing intracellular ATP, including the step of: orally administering the solid dispersion according to the present invention or a pharmaceutical composition including the solid dispersion to a subject in need of enhancement of intracellular ATP at 10 to 320 mg, preferably 20 to 320 mg, more preferably 40 to 280 mg, more preferably 40 to 240 mg, more preferably 40 to 180 mg, more preferably 60 to 140 mg, and further preferably 60 to 120 mg per day, and if desired, continuing the oral administration for at least 7 days.

The dose of the pharmaceutical composition of the present invention can be adjusted according to the content of the compound represented by General Formula (I) or a pharmaceutically acceptable salt thereof in the pharmaceutical composition of the present invention. The dose can be appropriately determined according to an administering method, and age, body weight, gender, symptoms and sensitivity to a drug of an administering subject, and the like, and can be adjusted according to the progress of improvement in symptoms. In the present invention, the pharmaceutical composition is preferably continuously administered at a constant dose.

The enteric-coated preparation of the present invention can be orally administered, for example, to an adult generally at a dose of 10 to 320 mg, preferably 20 to 320 mg, more preferably 40 to 280 mg, more preferably 40 to 240 mg, more preferably 40 to 180 mg, more preferably 60 to 140 mg, further preferably 60 to 120 mg, and particularly preferably 60 to 100 mg per day in terms of the content of the compound represented by General Formula (I) or a pharmaceutically acceptable salt thereof, and if desired, the oral administration can be continued for at least 7 days. The dose and the duration of the administration can be changed according to age, symptoms and the like. The dosing frequency is, for example, 1 to 3 times, preferably 1 or 2 times, and more preferably 1 time per day.

In one aspect of the present invention, because a state in which intracellular ATP is continuously or constantly enhanced is preferable, the dose and the dosing frequency of the pharmaceutical composition according to the present invention can be appropriately determined to achieve the state, and for example, the dosing frequency can be 2 or 3 times per day.

The relation between the enhancement of intracellular ATP and the treatment or prevention of diseases, disorders, or syndromes will be described below using neurodegenerative diseases as an example.

A neurodegenerative disease is a generic term for diseases of unknown cause in which a specific nerve cell group (for example, nerve cells related to cognitive function and cells related to motor function) among nerve cells in the brain and spinal cord is gradually damaged and shed. For these diseases, there is no disease-modifying drug that acts on the essential process of the pathological condition to suppress the progress of diseases, and at present, symptomatic therapy is performed.

The site of shedding nerve cells varies from disease to disease, and various symptoms such as dementia, ataxia, and muscle weakness are exhibited depending on the site to undergo degeneration. There are many unknown mechanisms by which neurodegenerative diseases are developed, but intracellular aggregation of abnormal proteins and subsequent cell death are phenomena common to many diseases. In addition, large amounts of ATP are consumed in diseased neural tissues due to the removal of denatured proteins by the ubiquitin-proteasome system. When the ATP concentration decreases due to facilitation in consumption of ATP (for example, a repair process from stress such as abnormal protein accumulation described above) or an insufficient production of ATP (for example, ischemia) in a tissue, decomposition of AMP is increased to maintain an energy charge (EC) value, and AMP is rapidly metabolized to uric acid via hypoxanthine.

The XOR inhibitory agent increases the amount of hypoxanthine and inosine in the blood by stopping AMP degradation at hypoxanthine, the hypoxanthine and inosine flow into nerve cells, and the purine nucleotide produced by the intracellular purine salvage cycle is regenerated into ATP. As a result, the intracellular ATP concentration can be increased or the decrease in the intracellular ATP concentration can be delayed and cell death can be suppressed. Therefore, enhancement of intracellular ATP can treat or prevent neurodegenerative diseases. Specific examples of such neurodegenerative diseases, particularly optic nerve disorders include, for example, glaucoma, optic neuritis, ischemic optic neuropathy, compressive optic neuropathy, rhinogenous optic neuropathy, demyelinating diseases (represented by multiple sclerosis), and toxic optic neuropathy (ethambutol, methanol, thinner and the like).

In diseases, disorders, or syndromes involving a deficiency of intracellular ATP, enhancement of intracellular ATP can treat or prevent such diseases, disorders, or syndromes by the same mechanism of action.

As one embodiment of the present invention, the compound represented by General Formula (I) or a pharmaceutically acceptable salt thereof has an XOR inhibitory activity, and thus is useful as an active ingredient of a pharmaceutical composition for enhancing intracellular ATP.

As another embodiment of the present invention, the intracellular ATP enhancing action is preferably effected by an intracellular purine salvage cycle.

As another embodiment of the present invention, the intracellular ATP enhancing action is preferably sustained even in presence of an uncoupler. The uncoupler is a drug that inhibits the function of mitochondria, reduces the efficiency of ATP production by respiration, and causes intracellular ATP to be in a state of being insufficient. Therefore, “Intracellular ATP enhancing action is sustained even in presence of an uncoupler” indicates that the intracellular ATP enhancing action is sustained even in a state where intracellular ATP tends to be insufficient, that is, a state of circulatory failure, a state where mitochondrial function is reduced, and a state where oxygen is deficient due to various other reasons (anemia, abnormal hemoglobin and the like). Examples of the uncoupler include carbonyl cyanide-m-chlorophenylhydrazone (which may be abbreviated as CCCP in the specification).

As another embodiment of the present invention, intracellular ATP enhancing action is preferably improvement of a state in which balance between production and consumption of ATP is tilted to a consumption side.

As another embodiment of the present invention, the intracellular ATP enhancing action is effected in hypoxic condition.

As another embodiment of the present invention, the intracellular ATP enhancing action is preferably effected in absolute or relative deficiency of ATP. The absolute deficiency of ATP means a state in which ATP is insufficient because oxygen required for ATP synthesis is insufficient, and examples of the specific state include, for example, circulatory failure. The relative deficiency of ATP means a state in which ATP is insufficient because the consumption of ATP increases, and examples of the specific state include, for example, abnormal protein accumulation (a state in which ATP for removing the accumulated abnormal proteins is insufficient).

As another embodiment of the present invention, the absolute or relative deficiency of ATP is preferably circulatory failure, abnormal protein accumulation, or tissue disorders (tissue disorders due to, for example, chemicals, trauma and the like).

In the present specification, the “enhancing” in the ATP enhancing action refers to a state in which the total amount of ATP and adenylate or adenylic acid which are metabolites thereof is significantly increased as compared with the control group (the group receiving no active ingredient). The “enhancing” in the ATP enhancing action preferably refers to a state in which ATP and/or ADP is significantly increased as compared with the control group (the group receiving no active ingredient), and the “enhancing” in the ATP enhancing action further preferably refers to a state in which ATP and/or ADP is significantly increased and AMP and/or IMP is significantly decreased as compared with the control group (the group receiving no active ingredient).

The “enhancing” means, as another embodiment, that when the intracellular ATP amount of a specific internal organ, tissue or the like of a healthy person is 100, the ATP amount is brought close to 100 or increased to 100 or more from a state of being less than 100 due to a disease or the like. For example, the “enhancing” means recovering the intracellular ATP concentration by 0.5% by mass or more with respect to the intracellular ATP concentration before administration of the pharmaceutical composition according to the present invention in a patient whose intracellular ATP amount has decreased due to a disease or the like, preferably means recovering the intracellular ATP concentration by 1% by mass or more, more preferably means recovering the intracellular ATP concentration by 2% by mass or more, further preferably means recovering the intracellular ATP concentration by 3% by mass or more, and further more preferably means recovering the intracellular ATP concentration by 5% by mass or more. The “state in which balance between production and consumption of ATP is tilted to a consumption side” refers to a pathological state (for example, a state in presence of an uncoupler or in hypoxic condition, or a state of abnormal protein accumulation). The “state in which balance between production and consumption of ATP is tilted to a consumption side” means that when the intracellular ATP amount of a specific internal organ, tissue, or the like of a healthy person is 100, the ATP amount is less than 100 due to a disease or the like, and the ATP amount is 95 or less to express that the state is more inclined to the consumption side, the ATP amount is 90 or less to express that the state is more inclined to the consumption side, and the ATP amount is 80 or less to express that the state is further inclined to the consumption side. The "hypoxic condition" refers to, in other words, a state of oxygen deficiency, refers to a state in which the blood flow of a tissue of a living body is reduced for some reason and oxygen supply to the tissue is not sufficiently performed, and refers to a state in which the intracellular ATP amount is reduced. Examples of the disease caused by the hypoxic condition include circulatory failure (heart failure, cerebral infarction and the like). As one embodiment, the "ATP enhancing action effected in hypoxic condition" refers to recovering the amount of ATP that has reduced in each disease of the circulatory failure. The "circulatory failure" is a disease in which the blood flow of a tissue of a living body is reduced for some reason and oxygen supply to the tissue is not sufficiently performed. Examples of the disease include chronic heart failure, cerebral infarction, and cardiomyopathy. The "abnormal protein accumulation" refers to a state in which proteins having an abnormal conformation are aggregated and accumulated in a tissue, and refers to, for example, a state in which abnormal proteins are accumulated in nerve cells. Examples of the disease characterized by the above condition include neurodegenerative diseases, retinitis pigmentosa, and age-related macular degeneration.

In one embodiment of the present invention, examples of diseases, disorders, or syndromes (which may be collectively referred to as "ATP-related diseases" in the present specification) to which the pharmaceutical composition for enhancing intracellular ATP is effective for treatment or prevention include hemolytic anemia, sickle cell disease, pyruvate kinase deficiency, spherocytosis, elliptocytosis, stomatocytosis, thalassemia, ischemic heart disease, heart failure, cardiovascular disorder, hypertension, tachycardia, arrhythmia, chronic progressive external ophthalmoplegia syndrome, ragged-red fiber, myoclonic epilepsy syndrome, mitochondrial encephalomyopathy, lactic acidosis, stroke-like syndrome, Leigh encephalopathy, mitochondrial cardiomyopathy, mitochondrial diabetes, Pearson's disease, amyotrophic lateral sclerosis, Parkinson's disease, multiple sclerosis, adenylosuccinate lyase deficiency, Alzheimer-type dementia, dementia with Lewy body, frontotemporal dementia, retinitis pigmentosa, cone-rod dystrophy, Oguchi disease, fundus albipunctatus, pigmented paravenous retinochoroidal atrophy, Leber congenital amaurosis, cone dystrophy, Stargardt disease, Best disease, familial exudative vitreoretinopathy, Wagner syndrome, Stickler syndrome, central areolar choroidal dystrophy, choroideremia, gyrus-like choroidal dystrophy, retinal degeneration secondary to uveitis, a retinal degenerative disease including a drug-induced (chloroquine and the like) retinal disorder, retinal vein occlusion, retinal artery occlusion, hypertensive retinopathy, diabetic retinopathy, renal retinopathy, age-related macular degeneration, central serous chorioretinopathy, retinal white spot syndrome, angioid streaks of the retina, rhegmatogenous retinal detachment involving the macula, macular hole, retinoschisis, exudative retinal detachment, proliferative vitreoretinopathy, retinal detachment associated with high myopia, Usher syndrome, Bardet-Biedl syndrome, Kearns-Sayre syndrome, Refsum syndrome, glaucoma, optic neuritis, ischemic optic neuropathy, compressive optic neuropathy, rhinogenous optic neuropathy, demyelinating optic neuropathy disease (represented by multiple sclerosis), and toxic optic neuropathy (by ethambutol, methanol, thinner and the like). Among them, retinitis pigmentosa, age-related macular degeneration, diabetic retinopathy, Leber congenital amaurosis, or glaucoma is suitable. Further, retinitis pigmentosa or age-related macular degeneration, glaucoma is optimal. That is, the pharmaceutical composition for enhancing intracellular ATP, which is one embodiment of the present invention, can be applied to the treatment or prevention of the diseases, disorders, or syndromes.

In one embodiment of the present invention, as the active ingredient of the pharmaceutical composition for enhancing intracellular ATP, only the compound represented by General Formula (I) or a pharmaceutically acceptable salt thereof is preferably contained without use of inosine, inosinic acid, hypoxanthine, or a salt thereof in combination.

In another embodiment of the present invention, as the active ingredient of the pharmaceutical composition for enhancing intracellular ATP, inosine, inosinic acid, hypoxanthine, or a salt thereof, and a compound represented by General Formula (I) or a pharmaceutically acceptable salt thereof can be contained.

Hyperuricemia is a condition in which the blood uric acid level is abnormally high. In hyperuricemia, a part of the uric acid cannot be completely dissolved, and the uric acid crystallizes. When the crystallized uric acid accumulates in the joint and results in inflammation, gouty arthritis is caused, which exhibits a symptom referred to as a gout attack with severe pain. Hyperuricemia includes hyperuricemia that exhibits such a clinical symptom of gouty arthritis and asymptomatic hyperuricemia with no clinical symptoms such as gouty arthritis.

The administration subject of the pharmaceutical composition provided by the present invention can be a patient in need of enhancing intracellular ATP. However, because administration of the pharmaceutical composition provided by the present invention can reduce the blood uric acid level, it is preferable to pay attention to the application to a patient with gout arthritis (for example, a patient with gouty arthritis who has developed hyperuricemia) or a patient with hyperuricemia who has developed a gout attack, and further a patient with asymptomatic hyperuricemia.

The terms "suppression of a gout attack", "suppression of induction of a gout attack", and "suppression of onset of a gout attack" used in the present specification refer to a decrease in frequency or severity (for example, a degree of pain or the like), preferably the frequency, of a "gout attack" as compared with a group of subjects administered with a conventional uric acid-lowering drug, for example, allopurinol or febuxostat, or a placebo group. The terms preferably include the absence of a "gout attack".

Generally, when a patient with gouty arthritis is treated to lower the blood uric acid level, a uric acid-lowering drug is administered after the remission of a gout attack (after the pain has subsided). At this time, it is required that the administration starts at a low dose, and the dose is gradually increased so that the blood uric acid level is gradually decreased to a target value. This is because when the blood uric acid level is rapidly decreased by the administration of the uric acid-lowering drug, the urate crystals attached to the joint are rapidly redissolved, as a result, peeling easily occurs, and a gout attack is induced. A gout attack caused by the rapid decrease in the uric acid level due to a uric acid-lowering drug is known as a mobilization flare-up.

Because the pharmaceutical composition provided by the present invention can gradually decrease the blood uric acid concentration, acute gout attacks such as mobilization flare-up can be suppressed without the gradual increases in the dose or with less gradual increases in the dose.

On the other hand, when febuxostat, an XOR inhibitory agent, is used for the treatment of gout, it is recommended in Japan that the dose is gradually increased, for example, from 10 mg once a day, to 20 mg once a day after 2 weeks from the start of administration, and to 40 mg once a day after 6 weeks from the start of administration to suppress the induction of gout attacks (mobilization flare-up) caused by a rapid decrease in blood uric acid level.

In one embodiment, the dose per day of the pharmaceutical composition provided by the present invention does not need to be gradually increased to suppress the onset of gout attacks (mobilization flare-up) associated with the start of administration, and the dose per day does not need to be increased in three weeks from the start of administration.

In one embodiment, the dose per day of the pharmaceutical composition provided by the present invention does not need to be gradually increased to suppress the onset of gout attacks (mobilization flare-up) associated with the start of administration, and the dose per day does not need to be increased in seven weeks from the start of administration, or the dose per day can be increased once or less.

The effect of gradually decreasing the blood uric acid level that can be exhibited by administering the pharmaceutical composition provided by the present invention can be exhibited, for example, by orally administering 10 to 320 mg (for example, 10 to 160 mg, 20 to 160 mg, 40 to 160 mg, 80 to 160 mg, 10 to 80 mg, 20 to 80 mg, 40 to 80 mg, 10 mg, 20 mg, 40 mg, 80 mg, 100 mg, 120 mg, 140 mg, or 160 mg) of a compound represented by General Formula (I) or a pharmaceutically acceptable salt thereof per day. The blood uric acid level can be gradually decreased by administering 10 to 320 mg (for example, 10 to 160 mg, 20 to 160 mg, 40 to 160 mg, 80 to 160 mg, 10 to 80 mg, 20 to 80 mg, 40 to 80 mg, 10 to 40 mg, 20 to 40 mg, 10 mg, 20 mg, 40 mg, 80 mg, 100 mg, 120 mg, 140 mg, or 160 mg) of the compound represented by General Formula (I) or a pharmaceutically acceptable salt thereof per day, and for example, the blood uric acid level can be gradually decreased by administering the compound represented by General Formula (I) or a pharmaceutically acceptable salt thereof for 7 consecutive days or more (for example, for 1 month, 2 months, or 3 months).

In one embodiment, the pharmaceutical composition including a compound represented by General Formula (I) or a pharmaceutically acceptable salt thereof of the present invention is used so that the pharmaceutical composition including the compound represented by General Formula (I) or a pharmaceutically acceptable salt thereof of the present invention is orally administered to a patient in need of treatment at 10 to 320 mg per day, and if desired, the oral administration is continued for at least 7 days. According to such an embodiment, the uric acid level of the patient can be gradually decreased without rapidly lowering the uric acid level of a patient, and thus the pharmaceutical composition including the compound represented by General Formula (I) or a pharmaceutically acceptable salt thereof of the present invention can be useful for enhancement of intracellular ATP while reducing the induction of gout attacks or the severity of attacks.

The effect of gradually reducing the blood uric acid level that can be exhibited by administering the pharmaceutical composition provided by the present invention can be confirmed, for example, by the maximum reduction rate of the blood uric acid level on Day 1 of administration ([(uric acid level before administration−minimum uric acid level after administration on Day 1 of administration)/uric acid level before administration]×100) of 35% or less (for example, a decrease of 1 to 35%, a decrease of 10 to 30%, a decrease of 10 to 25%, a decrease of 10 to 20%, or a decrease of 15 to 25%) and/or the maximum reduction rate of the blood uric acid level on Day 7 of administration ([(uric acid level before administration−minimum uric acid level after administration on Day 7 of administration)/uric acid level before administration]×100) of about 55% or less (for example, a decrease of 1 to 55%, a decrease of 10 to 50%, a decrease of 15 to 45%, a decrease of 20 to 45%, a decrease of 20 to 40%, or a decrease of 20 to 35%.) when the pharmaceutical composition provided by the present invention is administered to a healthy adult (for example, male) for 7 consecutive days and the blood uric acid levels before and after administration are measured.

The blood uric acid level (blood uric acid concentration) can be measured by a known uricase-peroxidase method.

In the present specification, the time or period represented by "from the start of administration" can be calculated, for example, from the time of the first administration of the compound represented by General Formula (I) or a pharmaceutically acceptable salt thereof in one treatment regimen. Thus, for example, "three weeks after the start of administration" means a corresponding time three weeks after the first administration, and "seven weeks after the start of administration" means a corresponding time seven weeks after the first administration.

The time or period indicated following the term "administration" refers to a time point at which the indicated time or period has elapsed from the starting point of the time of administration. For example, "administration 12 hours" means a time point at which 12 hours have elapsed from the time of administration, and "administration 7 days" means a time point at which 7 days have elapsed from the time of administration. In the present specification, the term "period" is usually used for a time defined by "day", "month", or "year".

In the present specification, the meaning of the expression "Day X of administration" can be determined in context. For example, "Day 1 of administration" may mean the time point after the lapse of 1 day (24 hours) from the time of the first administration in one treatment regimen, may mean the period from the time of the first administration to immediately before the time point after the lapse of 1 day (24 hours), or may mean the time, for example, ±12 hours, preferably ±6 hours, more preferably +2 hours before and after the time point after the lapse of 1 day (24 hours) from the time of the first administration.

In the present specification, the "minimum uric acid level after administration on Day 1 of administration" means, for example, the minimum uric acid level among the uric acid levels measured by a method known per se by collecting blood from the administration subject every hour from the first administration to the lapse of 1 day (after the lapse of 24 hours) in one treatment regimen. The "minimum uric acid level after administration on Day 7 of administration" means, for example, the minimum uric acid level among the uric acid levels measured by a method known per se by collecting blood from the administration subject every hour from the time point after elapse of 6 days (after elapse of 144 hours) from the time of first administration to after elapse of 7 days in one treatment regimen. "Before administration" is preferably 12 hours before the first administration, more preferably 6 hours before the first administration, further preferably 2 hours before the first administration, and particularly preferably 1 hour before the first administration in one treatment regimen. Therefore, the "uric acid level before administration" means, for example, a uric acid level measured by a method known per se by collecting blood from the administration subject 12 hours before the first administration, preferably 6 hours before the first administration, more preferably 2 hours before the first administration, and further preferably 1 hour before the first administration in one treatment regimen.

The content of the compound represented by General Formula (I) or a pharmaceutically acceptable salt thereof contained in the pharmaceutical composition provided by the present invention can be appropriately set by those skilled in the art. For example, the content of the compound represented by General Formula (I) or a pharmaceutically acceptable salt thereof contained in the pharmaceutical composition provided by the present invention can be 10 to 320 mg (for example, 10 to 160 mg, 20 to 160 mg, 40 to 160 mg, 80 to 160 mg, 10 to 80 mg, 20 to 80 mg, 40 to 80 mg, 10 to 40 mg, 20 to 40 mg, 10 mg, 20 mg, 40 mg, 80 mg, 100 mg, 120 mg, 140 mg, or 160 mg).

The pharmaceutical composition provided by the present invention can be one dosage unit. The content of the compound represented by General Formula (I) or a pharmaceutically acceptable salt thereof per dosage unit can be, for example, 10 to 320 mg (for example, 10 to 160 mg, 20 to 160 mg, 40 to 160 mg, 80 to 160 mg, 10 to 80 mg, 20 to 80 mg, 40 to 80 mg, 10 to 40 mg, 20 to 40 mg, 10 mg, 20 mg, 40 mg, 80 mg, 100 mg, 120 mg, 140 mg, or 160 mg).

The packaging form of the pharmaceutical composition provided by the present invention can be appropriately set by those skilled in the art. Examples of the packaging form include a plastic container, a glass container, and a PTP sheet. The pharmaceutical composition provided by the present invention can be provided as a package in which dosage units of the pharmaceutical composition required for continuous administration for 5 to 15 days are contained. For example, the pharmaceutical composition provided by the present invention can be provided as a PTP sheet including 5 to 15 (for example, 6, 7, 8, 10, 12, or 14) dosage units.

In the present specification, the "dosage unit" represents a unit of preparation, and the "one dosage unit" represents a minimum unit of preparation. Thus, for example, in the case of a tablet, the dosage unit is each tablet, and one dosage unit represents one tablet. In the case of an injection, the dosage unit is an injection contained in a sealed container such as an ampoule or a vial, and one dosage unit represents an injection contained in one sealed container such as one ampoule or vial.

When the pharmaceutical composition provided by the present invention is administered to a human or other mammals, one or more of the dosage unit can be administered per administration, or the one dosage unit can be divided and administered.

Examples of other embodiments of the present invention include the following.

<1-1> A pharmaceutical composition including a compound represented by General Formula (I) or a pharmaceutically acceptable salt thereof for use in enhancement of intracellular ATP.

<1-2> A pharmaceutical composition including a compound represented by General Formula (I) or a pharmaceutically acceptable salt thereof for use in treatment or prevention of hemolytic anemia, sickle cell disease, pyruvate kinase deficiency, spherocytosis, elliptocytosis, stomatocytosis, thalassemia, ischemic heart disease, heart failure, cardiovascular disorder, hypertension, tachycardia, arrhythmia, chronic progressive external ophthalmoplegia syndrome, ragged-red fiber, myoclonic epilepsy syndrome, mitochondrial encephalomyopathy, lactic acidosis, stroke-like syndrome, Leigh encephalopathy, mitochondrial cardiomyopathy, mitochondrial diabetes, Pearson's disease, amyotrophic lateral sclerosis, Parkinson's disease, multiple sclerosis, adenylosuccinate lyase deficiency, Alzheimer-type dementia, dementia with Lewy body, frontotemporal dementia, retinitis pigmentosa, cone-rod dystrophy, Oguchi disease, fundus albipunctatus, pigmented paravenous retinochoroidal atrophy, Leber congenital amaurosis, cone dystrophy, Stargardt disease, Best disease, familial exudative vitreoretinopathy, Wagner syndrome, Stickler syndrome, central areolar choroidal dystrophy, choroideremia, gyrus-like choroidal dystrophy, retinal degeneration secondary to uveitis, a retinal degenerative disease including a drug-induced (chloroquine and the like) retinal disorder, retinal vein occlusion, retinal artery occlusion, hypertensive retinopathy, diabetic retinopathy, renal retinopathy, age-related macular degeneration, central serous chorioretinopathy, retinal white spot syndrome, angioid streaks of the retina, rhegmatogenous retinal detachment involving the macula, macular hole, retinoschisis, exudative retinal detachment, proliferative vitreoretinopathy, retinal detachment associated with high myopia, Usher syndrome, Bardet-Biedl syndrome, Kearns-Sayre syndrome, Refsum syndrome, glaucoma, optic neuritis, ischemic optic neuropathy, compressive optic neuropathy, rhinogenous optic neuropathy, demyelinating optic neuropathy disease (represented by multiple sclerosis), or toxic optic neuropathy (by ethambutol, methanol, thinner and the like).

<1-3> The pharmaceutical composition for use according to <1-1> or <1-2>, which suppresses onset of a gout attack associated with start of the treatment or prevention.

<1-4> The pharmaceutical composition for use according to any one of <1-1> to <1-3>, which is used so that the compound represented by General Formula (I) or a pharmaceutically acceptable salt thereof is orally administered to a patient in need of enhancement of intracellular ATP at 10 to 320 mg per day, and if desired, the oral administration is continued for at least 7 days.

<1-5> The pharmaceutical composition for the use according to any one of <1-1> to <1-4>, in which R1 is an unsubstituted phenyl group or a phenyl group substituted with a halogen atom.

<1-6> The pharmaceutical composition for the use according to any one of <1-1> to <1-5>, in which X is an oxygen atom.

<1-7> The pharmaceutical composition for the use according to any one of <1-1> to <1-6>, in which Y is a sulfur atom.

<1-8> The pharmaceutical composition for the use according to any one of <1-1> to <1-7>, in which the compound according to any one of <1-1> to <1-7> or a pharmaceutically acceptable salt thereof includes an amorphous substance thereof, and a content of the amorphous substance is 80 weight % or more with respect to the total weight of the compound according to any one of <1-1> to <1-7> or a pharmaceutically acceptable salt thereof.

<1-9> The pharmaceutical composition for the use according to any one of <1-1> to <1-8>, which is an enteric-coated preparation.

<1-10> The pharmaceutical composition for the use according to <1-9>, in which the enteric-coated preparation is a hard capsule.

<1-11> The pharmaceutical composition for the use according to any one of <1-1> to <1-10>, further including a solid dispersion containing a hypromellose derivative.

<1-12> The pharmaceutical composition for the use according to <1-11>, in which a weight ratio between the compound represented by General Formula (I) or a pharmaceutically acceptable salt thereof and the hypromellose derivative is 1:0.1 to 1:25.

<1-13> The pharmaceutical composition for the use according to <1-11> or <1-12>, in which the hypromellose derivative is hypromellose acetate succinate or hypromellose phthalate.

<1-14> The pharmaceutical composition for the use according to any one of <1-1> to <1-13>, which is a solid preparation.

<1-15> The pharmaceutical composition for the use according to any one of <1-1> to <1-14>, in which a content of the compound represented by General Formula (I) or a pharmaceutically acceptable salt thereof is 10 mg to 320 mg.

<1-16> The pharmaceutical composition for the use according to any one of <1-1> to <1-15>, in which a content of the compound represented by General Formula (I) or a pharmaceutically acceptable salt thereof per dosage unit is 10 mg to 320 mg.

<1-17> The pharmaceutical composition for the use according to any one of <1-1> to <1-16>, in which the content of the compound represented by General Formula (I) or a pharmaceutically acceptable salt thereof per dosage unit is 10 mg to 160 mg.

<1-18> The pharmaceutical composition for the use according to any one of <1-1> to <1-17>, in which the content of the compound represented by General Formula (I) or a pharmaceutically acceptable salt thereof per dosage unit is 10 mg to 80 mg.

<1-19> The pharmaceutical composition for the use according to any one of <1-1> to <1-18>, in which the content of the compound represented by General Formula (I) or a pharmaceutically acceptable salt thereof per dosage unit is 20 mg to 80 mg.

<1-20> The pharmaceutical composition for the use according to any one of <1-1> to <1-19>, in which a blood uric acid concentration is lowered by 0.5 to 2.0 mg/dL (for example, 0.5 to 1.5 mg/dL) 12 hours after administration on the first day of the administration as compared with a blood uric acid concentration before the administration.

<1-21> The pharmaceutical composition for the use according to any one of <1-1> to <1-20>, in which, by continuous administration once/day for 7 days, a blood uric acid concentration is lowered by 1.5 to 3.0 mg/dL (for example, 1.5 to 2.5 mg/dL) 12 hours after administration on the seventh day of the administration as compared with the blood uric acid concentration before the administration.

<1-22> The pharmaceutical composition for the use according to any one of <1-1> to <1-21>, in which the pharmaceutical composition is continuously administered once/day, and a daily dose of the compound represented by General Formula (I) or a pharmaceutically acceptable salt thereof is not increased within 3 weeks of the administration after the start of the administration.

<1-23> The pharmaceutical composition for the use according to any one of <1-1> to <1-22>, in which the pharmaceutical composition is continuously administered once/day, and the daily dose of the compound represented by General Formula (I) or a pharmaceutically acceptable salt thereof is not increased or is increased once within 7 weeks of the administration after the start of the administration.

<1-24> The pharmaceutical composition for the use according to any one of <1-1> to <1-23>, in which the pharmaceutical composition is continuously administered once/day, and a maximum rate of decrease in a blood uric acid level on the first day of the administration ([(pre-administration uric acid level−minimum post-administration uric acid level on first day of administration)/pre-administration uric acid level]×100) is 10 to 25%.

<1-25> The pharmaceutical composition for the use according to any one of <1-1> to <1-24>, in which the pharmaceutical composition is continuously administered once/day, and a maximum rate of decrease in a blood uric acid level on the seventh day of the administration ([(pre-administration uric acid level−minimum post-administration uric acid level on seventh day of administration)/pre-administration uric acid level]×100) is 20 to 45%.

<1-26> The pharmaceutical composition for the use according to any one of <1-1> to <1-25>, in which the compound represented by General Formula (I) or a pharmaceutically acceptable salt thereof is 2-(3-cyano-4-phenoxyphenyl)-7-hydroxythiazolo[5,4-d]pyrimidine or a pharmaceutically acceptable salt thereof.

<1-27> A package including the pharmaceutical composition for the use according to any one of <1-1> to <1-26>, in which the number of dosage units of the pharmaceutical composition in the package is the number required for continuous administration for 5 to 15 days.

<1-28> An enhancer for use in enhancement of ATP, ADP, GTP, or GDP in a tissue, an organ, an internal organ, or a cell in which expression of a target enzyme XOR is substantially not observed or is small in a cell, including:

an XOR inhibitor as an active ingredient.

<1-29> The enhancer for use according to <1-28>, wherein the XOR inhibitor is the compound represented by General Formula (I) or a pharmaceutically acceptable salt thereof, allopurinol, topiroxostat, or febuxostat.

<1-30> The enhancer for use according to <1-28> or <1-29>, wherein the organ in which expression of a target enzyme XOR is substantially not observed or is small is an eyeball.

<1-31> The enhancer for use according to any one of <1-28> to <1-30>, wherein the tissue in which expression of a target enzyme XOR is substantially not observed or is small is a retina.

<1-32> The enhancer for use according to any one of <1-28> to <1-30>, wherein the tissue in which expression of a target enzyme XOR is substantially not observed or is small is an optic nerve.

<1-33> The enhancer for use according to any one of <1-28> to <1-32>, wherein the enhancer further includes an ATP precursor.

<1-34> The enhancer for use according to <1-33>, wherein the ATP precursor is inosine and/or hypoxanthine.

<1-35> A therapeutic and/or preventive agent for use in the treatment and/or prevention of an ATP-related disease in a tissue, an organ, an internal organ, or a cell in which expression of a target enzyme XOR is substantially not observed or is small in a cell, including:

an XOR inhibitor as an active ingredient.

<1-36> The therapeutic and/or preventive agent for use according to <1-35>, wherein the XOR inhibitor is the compound represented by General Formula (I) or a pharmaceutically acceptable salt thereof, allopurinol, topiroxostat, or febuxostat.

<1-37> The therapeutic and/or preventive agent for use according to <1-35> or <1-36>, wherein the organ in which expression of a target enzyme XOR is substantially not observed or is small is an eyeball.

<1-38> The therapeutic and/or preventive agent for use according to any one of <1-35> to <1-37>, wherein the tissue in which expression of a target enzyme XOR is substantially not observed or is small is a retina.

<1-39> The therapeutic and/or preventive agent for use according to any one of <1-35> to <1-37>, wherein the tissue in which expression of a target enzyme XOR is substantially not observed or is small is an optic nerve.

<1-40> The therapeutic and/or preventive agent for use according to any one of <1-35> to <1-39>, wherein the ATP-related disease is an ATP-related eye disease.

<1-41> The therapeutic and/or preventive agent for use according to <1-40>, wherein the ATP-related eye disease is retinitis pigmentosa, cone-rod dystrophy, Oguchi disease, fundus albipunctatus, pigmented paravenous retinochoroidal atrophy, Leber congenital amaurosis, cone dystrophy, Stargardt disease, Best disease, familial exudative vitreoretinopathy, Wagner syndrome, Stickler syndrome, central areolar choroidal dystrophy, choroideremia, gyrus-like choroidal dystrophy, retinal degeneration secondary to uveitis, a retinal degenerative disease including a drug-induced (including chloroquine) retinal disorder, retinal vein occlusion, retinal artery occlusion, hypertensive retinopathy, diabetic retinopathy, renal retinopathy, age-related macular degeneration, central serous chorioretinopathy, retinal white spot syndrome, angioid streaks of the retina, rhegmatogenous retinal detachment involving the macula, macular hole, retinoschisis, exudative retinal detachment, proliferative vitreoretinopathy, retinal detachment associated with high myopia, Usher syndrome, Bardet-Biedl syndrome, Kearns-Sayre syndrome, Refsum syndrome, glaucoma, optic neuritis, ischemic optic neuropathy, compressive optic neuropathy, rhinogenous optic neuropathy, demyelinating optic neuropathy disease (including multiple sclerosis), or toxic optic neuropathy (including ethambutol, methanol, and thinner).

<1-42> A pharmaceutical composition for use in the treatment and/or prevention of an ATP-related disease in a tissue, an organ, an internal organ, or a cell in which expression of a target enzyme XOR is substantially not observed or is small in a cell, including:

an XOR inhibitor as an active ingredient.

<1-43> The pharmaceutical composition for use according to <1-42>, further including an ATP precursor.

<1-44> The pharmaceutical composition for use according to <1-43>, wherein the ATP precursor is inosine and/or hypoxanthine.

<2-1> Use of a compound represented by General Formula (I) or a pharmaceutically acceptable salt thereof for producing a pharmaceutical composition for enhancing intracellular ATP.

<2-2> Use of a compound represented by General Formula (I) or a pharmaceutically acceptable salt thereof for producing a pharmaceutical composition for treatment or prevention of hemolytic anemia, sickle cell disease, pyruvate kinase deficiency, spherocytosis, elliptocytosis, stomatocytosis, thalassemia, ischemic heart disease, heart failure, cardiovascular disorder, hypertension, tachycardia, arrhythmia, chronic progressive external ophthalmoplegia syndrome, ragged-red fiber, myoclonic epilepsy syndrome, mitochondrial encephalomyopathy, lactic acidosis, stroke-like syndrome, Leigh encephalopathy, mitochondrial cardiomyopathy, Leber disease, mitochondrial diabetes, Pearson's disease, amyotrophic lateral sclerosis, Parkinson's disease, multiple sclerosis, adenylosuccinate lyase deficiency, Alzheimer-type dementia, dementia with Lewy body, frontotemporal dementia, retinitis pigmentosa, cone-rod dystrophy, Oguchi disease, fundus albipunctatus, pigmented paravenous retinochoroidal atrophy, Leber congenital amaurosis, cone dystrophy, Stargardt disease, Best disease, familial exudative vitreoretinopathy, Wagner syndrome, Stickler syndrome, central areolar choroidal dystrophy, choroideremia, gyrus-like choroidal dystrophy, retinal degeneration secondary to uveitis, a retinal degenerative disease including a drug-induced (chloroquine and the like) retinal disorder, retinal vein occlusion, retinal artery occlusion, hypertensive retinopathy, diabetic retinopathy, renal retinopathy, age-related macular degeneration, central serous chorioretinopathy, retinal white spot syndrome, angioid streaks of the retina, rhegmatogenous retinal detachment involving the macula, macular hole, retinoschisis, exudative retinal detachment, proliferative vitreoretinopathy, retinal detachment associated with high myopia, Usher syndrome, Bardet-Biedl syndrome, Kearns-Sayre syndrome, Refsum syndrome, glaucoma, optic neuritis, ischemic optic neuropathy, compressive optic neuropathy, rhinogenous optic neuropathy, demyelinating optic neuropathy disease (represented by multiple sclerosis), or toxic optic neuropathy (by ethambutol, methanol, thinner and the like).

<2-3> The use according to <2-1> or <2-2>, which suppresses onset of a gout attack associated with start of the treatment or prevention.

<2-4> The use according to any one of <2-1> to <2-3>, wherein the compound represented by General Formula (I) or a pharmaceutically acceptable salt thereof is used so that the compound represented by General Formula (I) or a pharmaceutically acceptable salt thereof is orally administered to a patient in need of enhancement of intracellular ATP at 10 to 320 mg per day, and if desired, the oral administration is continued for at least 7 days.

<2-5> The use according to any one of <2-1> to <2-4>, in which R1 is an unsubstituted phenyl group or a phenyl group substituted with a halogen atom.

<2-6> The use according to any one of <2-1> to <2-5>, in which X is an oxygen atom.

<2-7> The use according to any one of <2-1> to <2-6>, in which Y is a sulfur atom.

<2-8> The use according to any one of <2-1> to <2-7>, in which the compound according to any one of <2-1> to <2-7> or a pharmaceutically acceptable salt thereof includes an amorphous substance thereof, and a content of the amorphous substance is 80 weight % or more with respect to the total weight of the compound according to any one of <2-1> to <2-7> or a pharmaceutically acceptable salt thereof.

<2-9> The use according to any one of <2-1> to <2-8>, in which the pharmaceutical composition is an enteric-coated preparation.

<2-10> The use according to <2-9>, in which the enteric-coated preparation is a hard capsule.

<2-11> The use according to any one of <2-1> to <2-10>, in which the pharmaceutical composition further includes a solid dispersion containing a hypromellose derivative.

<2-12> The use according to <2-11>, in which a weight ratio between the compound represented by General Formula (I) or a pharmaceutically acceptable salt thereof and the hypromellose derivative is 1:0.1 to 1:25.

<2-13> The use according to <2-11> or <2-12>, in which the hypromellose derivative is hypromellose acetate succinate or hypromellose phthalate.

<2-14> The use according to any one of <2-1> to <2-13>, in which the pharmaceutical composition is a solid preparation.

<2-15> The use according to any one of <2-1> to <2-14>, in which a content of the compound represented by General Formula (I) or a pharmaceutically acceptable salt thereof is 10 mg to 320 mg.

<2-16> The use according to any one of <2-1> to <2-15>, in which a content of the compound represented by General Formula (I) or a pharmaceutically acceptable salt thereof per dosage unit of the pharmaceutical composition is 10 mg to 320 mg.

<2-17> The use according to any one of <2-1> to <2-16>, in which the content of the compound represented by General Formula (I) or a pharmaceutically acceptable salt thereof per dosage unit of the pharmaceutical composition is 10 mg to 160 mg.

<2-18> The use according to any one of <2-1> to <2-17>, in which the content of the compound represented by General Formula (I) or a pharmaceutically acceptable salt thereof per dosage unit of the pharmaceutical composition is 10 mg to 80 mg.

<2-19> The use according to any one of <2-1> to <2-18>, in which the content of the compound represented by General Formula (I) or a pharmaceutically acceptable salt thereof per dosage unit of the pharmaceutical composition is 20 mg to 80 mg.

<2-20> The use according to any one of <2-1> to <2-19>, in which the pharmaceutical composition lowers a blood uric acid concentration by 0.5 to 2.0 mg/dL (for example, 0.5 to 1.5 mg/dL) 12 hours after administration on the first day of the administration as compared with a blood uric acid concentration before the administration.

<2-21> The use according to any one of <2-1> to <2-20>, in which the pharmaceutical composition is continuously administered once/day for 7 days, and a blood uric acid concentration is lowered by 1.5 to 3.0 mg/dL (for example, 1.5 to 2.5 mg/dL) 12 hours after administration on the seventh day of the administration as compared with the blood uric acid concentration before the administration.

<2-22> The use according to any one of <2-1> to <2-21>, in which the pharmaceutical composition is continuously administered once/day, and a daily dose of the compound represented by General Formula (I) or a pharmaceutically acceptable salt thereof is not increased within 3 weeks of the administration after the start of the administration.

<2-23> The use according to any one of <2-1> to <2-22>, in which the pharmaceutical composition is continuously administered once/day, and the daily dose of the compound represented by General Formula (I) or a pharmaceutically acceptable salt thereof is not increased or is increased once within 7 weeks of the administration after the start of the administration.

<2-24> The use according to any one of <2-1> to <2-23>, in which the pharmaceutical composition is continuously administered once/day, and a maximum rate of decrease in a blood uric acid level on the first day of the administration ([(pre-administration uric acid level−minimum post-administration uric acid level on first day of administration)/pre-administration uric acid level]×100) is 10 to 25%.

<2-25> The use according to any one of <2-1> to <2-24>, in which the pharmaceutical composition is continuously administered once/day, and a maximum rate of decrease in a blood uric acid level on the seventh day of the administration ([(pre-administration uric acid level−minimum post-administration uric acid level on seventh day of administration)/pre-administration uric acid level]×100) is 20 to 45%.

<2-26> The use according to any one of <2-1> to <2-25>, in which the compound represented by General Formula (I) or a pharmaceutically acceptable salt thereof is 2-(3-cyano-4-phenoxyphenyl)-7-hydroxythiazolo[5,4-d]pyrimidine or a pharmaceutically acceptable salt thereof.

<2-27> Use of a compound represented by General Formula (I) or a pharmaceutically acceptable salt thereof for producing a package including the pharmaceutical composition according to any one of <2-1> to <2-26>, in which the number of dosage units of the pharmaceutical composition in the package is the number required for continuous administration for 5 to 15 days.

<2-28> Use of an XOR inhibitor for producing an enhancer of ATP, ADP, GTP, or GDP in a tissue, an organ, an internal organ, or a cell in which expression of a target enzyme XOR is substantially not observed or is small in a cell.

<2-29> The use according to <2-28>, wherein the XOR inhibitor is the compound represented by General Formula (I) or a pharmaceutically acceptable salt thereof, allopurinol, topiroxostat, or febuxostat.

<2-30> The use according to <2-28> or <2-29>, wherein the organ in which expression of a target enzyme XOR is substantially not observed or is small is an eyeball.

<2-31> The use according to any one of <2-28> to <2-30>, wherein the tissue in which expression of a target enzyme XOR is substantially not observed or is small is a retina.

<2-32> The use according to any one of <2-28> to <2-30>, wherein the tissue in which expression of a target enzyme XOR is substantially not observed or is small is an optic nerve.

<2-33> The use according to any one of <2-28> to <2-32>, wherein the enhancer further includes an ATP precursor.

<2-34> The use according to <2-33>, wherein the ATP precursor is inosine and/or hypoxanthine.

<2-35> Use of an XOR inhibitor for producing a therapeutic and/or preventive agent for an ATP-related disease in a tissue, an organ, an internal organ, or a cell in which expression of a target enzyme XOR is substantially not observed or is small in a cell.

<2-36> The use according to <2-35>, wherein the XOR inhibitor is the compound represented by General Formula (I) or a pharmaceutically acceptable salt thereof, allopurinol, topiroxostat, or febuxostat.

<2-37> The use according to <2-35> or <2-36>, wherein the organ in which expression of a target enzyme XOR is substantially not observed or is small is an eyeball.

<2-38> The use according to any one of <2-35> to <2-37>, wherein the tissue in which expression of a target enzyme XOR is substantially not observed or is small is a retina.

<2-39> The use according to any one of <2-35> to <2-37>, wherein the tissue in which expression of a target enzyme XOR is substantially not observed or is small is an optic nerve.

<2-40> The use according to any one of <2-35> to <2-39>, wherein the ATP-related disease is an ATP-related eye disease.

<2-41> The use according to <2-40>, wherein the ATP-related eye disease is retinitis pigmentosa, cone-rod dystrophy, Oguchi disease, fundus albipunctatus, pigmented paravenous retinochoroidal atrophy, Leber congenital amaurosis, cone dystrophy, Stargardt disease, Best disease, familial exudative vitreoretinopathy, Wagner syndrome, Stickler syndrome, central areolar choroidal dystrophy, choroideremia, gyrus-like choroidal dystrophy, retinal degeneration secondary to uveitis, a retinal degenerative disease including a drug-induced (including chloroquine) retinal disorder, retinal vein occlusion, retinal artery occlusion, hypertensive retinopathy, diabetic retinopathy, renal retinopathy, age-related macular degeneration, central serous chorioretinopathy, retinal white spot syndrome, angioid streaks of the retina, rhegmatogenous retinal detachment involving the macula, macular hole, retinoschisis, exudative retinal detachment, proliferative vitreoretinopathy, retinal detachment associated with high myopia, Usher syndrome, Bardet-Biedl syndrome, Kearns-Sayre syndrome, Refsum syndrome, glaucoma, optic neuritis, ischemic optic neuropathy, compressive optic neuropathy, rhinogenous optic neuropathy, demyelinating optic neuropathy disease (including multiple sclerosis), or toxic optic neuropathy (including ethambutol, methanol, and thinner).

<2-42> Use of an XOR inhibitor for producing a pharmaceutical composition for treating and/or preventing an ATP-related disease in a tissue, an organ, an internal organ, or a cell in which expression of a target enzyme XOR is substantially not observed or is small in a cell.

<2-43> The use according to <2-42>, wherein the pharmaceutical composition further includes an ATP precursor.

<2-44> The use according to <2-43>, wherein the ATP precursor is inosine and/or hypoxanthine.

Examples of other embodiments of the present invention include an enhancer of ATP, ADP, GTP, or GDP in a tissue, an organ, an internal organ, or a cell in which expression of a target enzyme XOR is substantially not observed or is small in a cell, including an XOR inhibitor as an active ingredient. The XOR inhibitor enhances ATP, ADP, GTP, or GDP and increases the energy charge (EC) value also in the tissue, organ, internal organ, or cell, thereby increasing the cell viability of the tissue, organ, internal organ, or cell and suppressing cell death.

The fact that expression of XOR is substantially not observed or is small can be examined by a known technique, for example, a genetic engineering technique (RT-PCR method, Northern blotting method, microarray method), an immunohistological technique as shown in Examples of the present application, a biochemical technique (measurement of enzyme activity) or the like. In the present invention, the "expression of XOR is not substantially observed" means that the expression level of XOR is too small to be detected by the above method, and "expression of XOR is small" means that, for example, the enzyme activity in lysate is 0.1 nmole uric acid/min/mg protein or less or 0.05 nmole uric acid/min/mg protein or less, or the value of GTEx is 1, 0.8, 0.6, 0.5, 0.4, 0.3, 0.2, or 0.1 nTPN or less, or the value of FANTOM 5 is 1, 0.8, 0.6, 0.5, 0.4, 0.3, 0.2, or 0.1 Scaled Tags Per Million or less as the expression level of RNA at the site (https://www.proteinatlas.org/ENSG00000158125-XDH/tissue) of Xanthine dehydrogenase (XDH) in the known database "THE HUMAN PROTEIN ATLAS".

Examples of the organ in which expression of a target enzyme XOR is substantially not observed or is small in a cell include the eyeball. Examples of the tissue in which expression of a target enzyme XOR is substantially not observed or is small in a cell include the retina and the optic nerve.

In the present invention, the "XOR inhibitor" means a compound that inhibits XOR which is a target enzyme. Examples of the XOR inhibitor include a compound represented by General Formula (I) or a pharmaceutically acceptable salt thereof, allopurinol, topiroxostat, and febuxostat.

The enhancer of ATP, ADP, GTP, or GDP of the present invention can further contain an ATP precursor. The ATP precursor can be used directly or indirectly in the purine salvage pathway to increase the effect as an enhancer of XOR inhibitors. Examples of the ATP precursor include hypoxanthine and inosine, and the ATP precursor can act separately from the XOR inhibitor.

Examples of other embodiments of the present invention include a therapeutic and/or preventive agent for an ATP-related disease in a tissue, an organ, an internal organ, or a cell in which expression of a target enzyme XOR is substantially not observed or is small in a cell, including an XOR inhibitor as an active ingredient.

Examples of the embodiment of the present invention include a therapeutic and/or preventive agent for an ATP-related eye disease, including an XOR inhibitor as an active ingredient. Examples of the ATP-related eye disease include diseases that cause disorders of the retina or the optic nerve, and specific examples thereof include retinitis pigmentosa, cone-rod dystrophy, Oguchi disease, fundus albipunctatus, pigmented paravenous retinochoroidal atrophy, Leber congenital amaurosis, cone dystrophy, Stargardt disease, Best disease, familial exudative vitreoretinopathy, Wagner syndrome, Stickler syndrome, central areolar choroidal dystrophy, choroideremia, gyrus-like choroidal dystrophy, retinal degeneration secondary to uveitis, a retinal degenerative disease including a drug-induced (including chloroquine) retinal disorder, retinal vein occlusion, retinal artery occlusion, hypertensive retinopathy, diabetic retinopathy, renal retinopathy, age-related macular degeneration, central serous chorioretinopathy, retinal white spot syndrome, angioid streaks of the retina, rhegmatogenous retinal detachment involving the macula, macular hole, retinoschisis, exudative retinal detachment, proliferative vitreoretinopathy, retinal detachment associated with high myopia, Usher syndrome, Bardet-Biedl syndrome, Kearns-Sayre syndrome, Refsum syndrome, glaucoma, optic neuritis, ischemic optic neuropathy, compressive optic neuropathy, rhinogenous optic neuropathy, demyelinating optic neuropathy disease (including multiple sclerosis), and toxic optic neuropathy (including ethambutol, methanol, and thinner).

The method for administering the XOR inhibitor of the present invention can be appropriately selected for each disease. For example, for ATP-related eye diseases, for example, a tablet is preferably orally administered, but the administration method is not limited thereto. This is because, in the present invention, it has become clear that when an XOR inhibitor is orally administered, the amount of hypoxanthine and inosine increases in a living body such as the liver, and hypoxanthine and inosine that have migrated into the blood pass through the blood-retinal barrier to increase ATP in the eyeball.

The XOR inhibitor of the present invention can be a pharmaceutical composition, and a pharmaceutically acceptable additive can be incorporated as necessary. For example, a pharmaceutical composition including the XOR inhibitor of the present invention as an active ingredient can be produced by appropriately combining and incorporating a binder, a disintegrant, an excipient, a lubricant and the like in a required amount. The pharmaceutical composition can be produced as a medicine in an appropriate dosage form such as a tablet, a capsule, a granule, a powder, an eye drop, a gargle, an ointment, a cream, a gel, a poultice, a patch, a liniment, a tape, a cataplasm, an injection, or a suppository according to usual methods in the technical field of preparations.

Examples of the binder include methyl cellulose, hydroxyethyl cellulose, hydroxypropyl cellulose, hypromellose, polyvinyl pyrrolidone, gelatin, agar, alginic acid, sodium alginate, partially saponified polyvinyl alcohol, pullulan, partly pregelatinized starch, dextrins, xanthan gum, and gum arabic powder. These can be used alone or as a mixture of two or more thereof. Among these, hydroxypropyl cellulose, hypromellose, polyvinylpyrrolidone and the like are preferable.

Examples of the disintegrant include crystalline cellulose, carboxymethyl cellulose (also referred to as carmellose), croscarmellose sodium, calcium carboxymethyl cellulose, low-substituted hydroxypropyl cellulose, crospovidone, hydroxypropyl starch, starch, partly pregelatinized starch, and starch sodium glycolate. These can be used alone or as a mixture of two or more thereof.

The excipient can be incorporated in any of a kneading step, a granulation step, and a post-granulation end step of pharmaceutical preparations. Examples of the excipient include celluloses such as crystalline cellulose, ethyl cellulose, hydroxypropyl cellulose, low-substituted hydroxypropyl cellulose, and hydroxypropylmethylcellulose (also referred to as hypromellose), starches such as corn starch, potato starch, wheat starch, rice starch, partly pregelatinized starch, and hydroxypropyl starch, sugars such as glucose, lactose, white sugar, refined white sugar, powdered sugar, trehalose, dextran, and dextrin, sugar alcohols such as D-mannitol, xylitol, sorbitol, and erythritol, glycerin fatty acid esters, and inorganic salts such as magnesium aluminometasilicate, synthetic hydrotalcite, anhydrous calcium phosphate, precipitated calcium carbonate, calcium silicate, calcium hydrogen phosphate hydrate, and sodium hydrogen carbonate.

Examples of the lubricant include stearic acid, sodium stearyl fumarate, magnesium stearate, calcium stearate, sucrose fatty acid ester, polyethylene glycol, light anhydrous silicic acid, hardened oils, glycerin fatty acid esters, and talc, and these can be used alone or as a mixture of two or more thereof.

The dose of the XOR inhibitor can be an effective amount, and the compound represented by General Formula (I) or a pharmaceutically acceptable salt thereof is administered orally or parenterally at a dose of 10 to 320 mg, allopurinol is administered orally or parenterally at a dose of 50 mg to 800 mg, topiroxostat is administered orally or parenterally at a dose of 40 to 160 mg, and febuxostat is administered orally or parenterally at a dose of 10 to 80 mg per day. If desired, the administration is continued for at least 7 days, 10 days, 18 days, 1 month, 3 months, half a year or 1 year.

The pharmaceutical composition including the XOR inhibitor can further include an ATP precursor, and examples of the ATP precursor include hypoxanthine and inosine. The dose of the ATP precursor can be an effective amount, and the ATP precursor is administered orally or parenterally, for example, at a dose of 0.5 to 4.0 g per day. The ATP precursor can be administered separately from the XOR inhibitor.

EXAMPLES

Hereinafter, the present invention will be described in more detail with reference to Examples, Reference Examples, Comparative Reference Examples, and Test Examples, but the present invention is not limited thereto.

Reference Example 1a and Comparative Reference Example 1a, Production of Enteric-Coated Capsules After dissolving 9 g of Compound 14 (2-(3-cyano-4-phenoxyphenyl)-7-hydroxythiazolo[5,4-d]pyrimidine) in 1936 g of a mixed solvent of tetrahydrofuran (may be abbreviated as THF), ethanol, and water (weight ratio: THF/ethanol/water=1600.5/254.5/81) (dissolved by slightly heating), the solution was pumped into a spray dryer at a rate of about 5 mL/min via a peristaltic pump and spray dried and granulated from a 2-fluid nozzle (with a diameter of 508 μm) at an inlet temperature of 80° C. and an outlet temperature of about 60° C. under conditions of a dry air flow of 0.30 $m^3$/min and a nozzle spray air pressure of 1.0 kgf/$cm^2$. The obtained dried component was allowed to stand overnight at room temperature to obtain 100% amorphous Compound 14.

A volume average particle size (D50) of the obtained amorphous Compound 14 was measured with a Shimadzu laser diffraction type particle size distribution measuring device SALD-2200 using a dispersion obtained by adding about 2 mg of a sample to a 0.2% Aerosol OT aqueous solution and irradiating the solution with ultrasonic waves for 30 seconds for dispersion. Shimadzu WingSALD-2200 version 1.02 software was used for data collection and analysis. FIG. 1 shows the result of the particle size distribution of amorphous Compound 14. The volume average particle size (D50) of amorphous Compound 14 obtained from the particle size distribution was 2.949 μm.

Each of the capsules shown in Table 2A was filled with 40 mg of the obtained amorphous Compound 14 to obtain capsules of amorphous Compound 14.

TABLE 2A

| | Capsule name | Enteric properties | Capsule component | Capsule manufacturer |
|---|---|---|---|---|
| Reference Example 1a | Vcaps (registered trademark) Enteric | Enteric | HPMCAS/HPMC | Lonza/Capsugel |
| Comparative Reference Example 1a | Vcaps Plus (registered trademark) | Not enteric | HPMC | Lonza/Capsugel |

Test Example 1a, Absorbability of Amorphous Compound 14 in Dogs

Single oral administration of the capsules of Reference Example 1a and Comparative Reference Example 1a (40 mg/body as Compound 14) was performed on beagle dogs (1 to 5 years old, KITAYAMA LABES CO., LTD.) that had been fasted from the evening of the day before the administration one capsule at a time by a crossover method with a one-week administration interval. Blood was collected from the cephalic vein, and the time of the collection was 0.5, 1, 3, 5, 8, and 24 hours before and after the administration. The obtained blood was centrifuged at 10000×g and 4° C. for 5 minutes to obtain plasma. The concentration of Compound 14 in the plasma was measured by HPLC (OSAKA SODA CO., LTD.). Since dogs generally have a high gastric pH, pentagastrin, a gastric acid stimulator, was intramuscularly injected at a dose of 0.01 mg/kg 30 minutes before and immediately before the administration of the capsules. Then, the pH of a gastric solution was measured to confirm that the gastric pH was low, and the capsule sample was administered.

Figure 2:
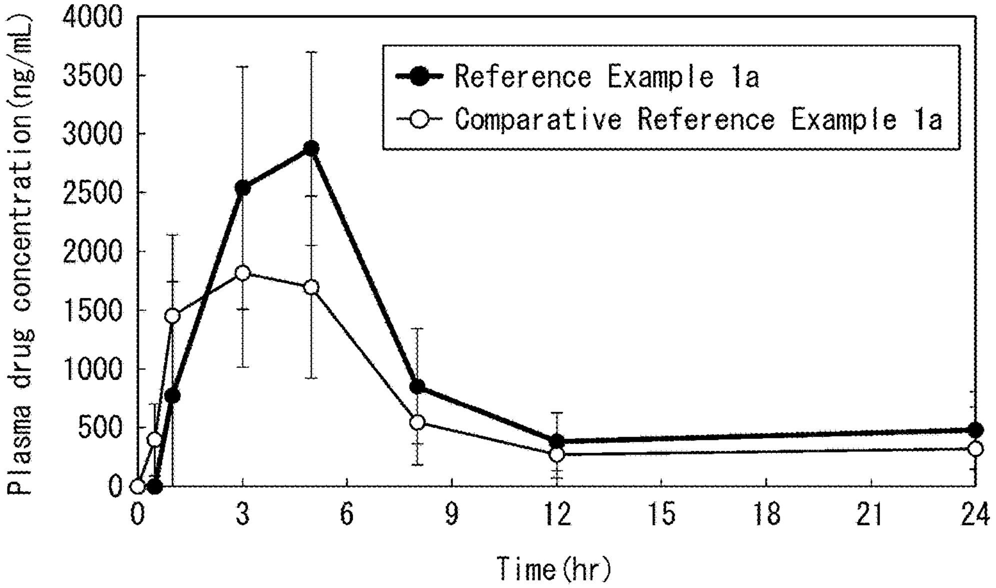
FIG. 2 is a diagram showing plasma drug concentration-time curves when a capsule of Reference Example 1a and a capsule of Comparative Reference Example 1a were administered to dogs.

Plasma drug concentration-time curves were created from the obtained measurement values. The results are shown in FIG. 2. The drug concentrations in the figure show the mean value±standard deviation of four examples.

When the enteric-coated capsule of Reference Example 1a was used, the drug concentration was higher than that when the general gastric-soluble capsule of Comparative Reference Example 1a, which was not enteric-coated, was used. Thus, absorbability was shown to be improved by the enteric-coating of amorphous Compound 14.

Test Example 2a, Evaluation of Amorphous State of Compound 14 (Powder X-Ray Diffraction)

Figure 3:
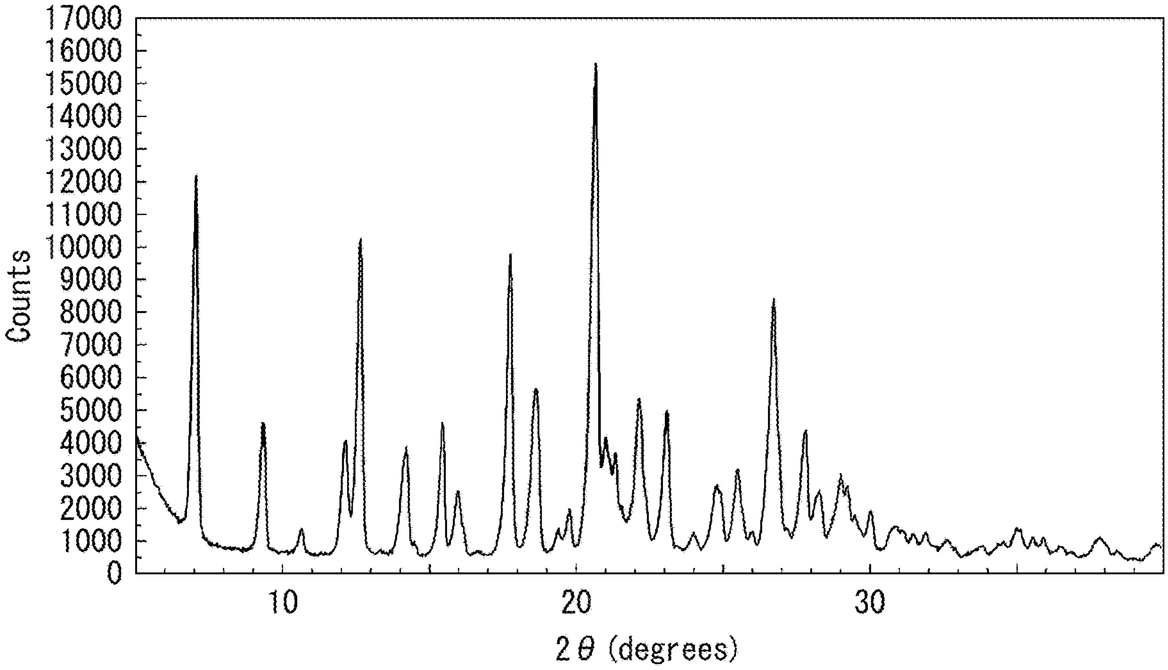
FIG. 3 is a diagram showing a powder X-ray diffraction pattern of crystalline Compound 14.
Figure 4:
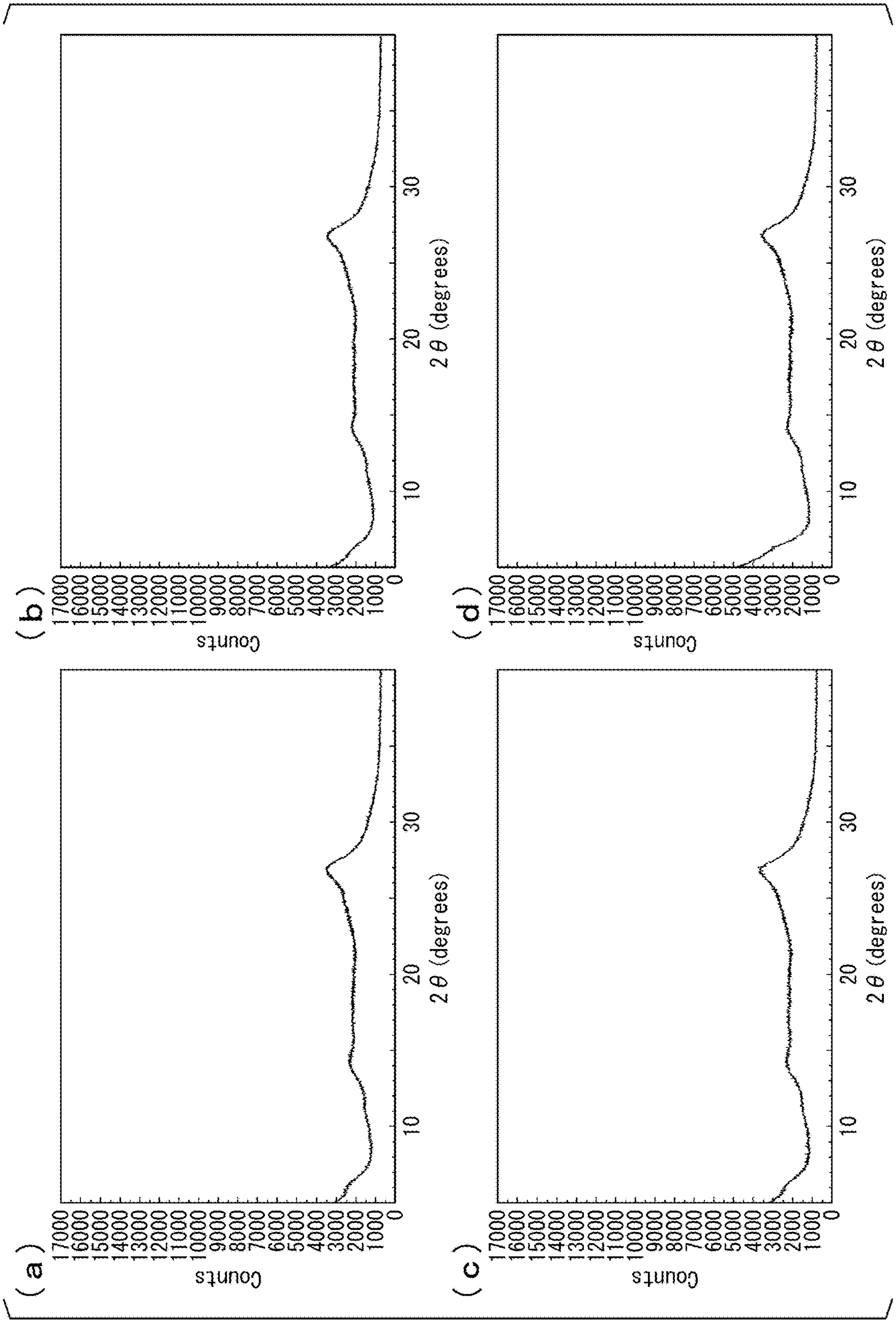
FIG. 4 is a diagram showing powder X-ray diffraction patterns of amorphous Compound 14, in which (a) is a powder X-ray diffraction pattern before storage, (b) is a powder X-ray diffraction pattern after storage for 1 week under a room temperature condition in a light-shielded and airtight manner, (c) is a powder X-ray diffraction pattern after storage for 2 weeks under a room temperature condition in a light-shielded and airtight manner, and (d) is a powder X-ray diffraction pattern after storage after storage for 4 weeks under a room temperature condition in a light-shielded and airtight manner.

Since it is very important that an amorphous substance retains amorphous properties even after storage over time, amorphous Compound 14 of Reference Example 1a was stored at room temperature in a light-shielded and airtight manner, and a change in the amorphous state of Compound 14 was evaluated using an X-ray diffraction device (D2 Phaser, Bruker). The results are shown in FIGS. 4(*a*) to (*d*). For comparison, FIG. 3 shows the powder X-ray diffraction of crystalline Compound 14.

When the capsule of Reference Example 1a was stored at room temperature in a light-shielded and airtight manner, changes in the powder X-ray diffraction pattern of Compound 14 over time were not observed during the storage for 4 weeks.

Reference Example 1b and Comparative Reference Examples 1b to 9b. Production of Solid Dispersions (polymer, 25-fold amount)

250 mg of Compound 14 was dissolved in tetrahydrofuran to obtain a 100 mL of a solution. To 125 mg of each of polymers shown in Table 2B, 5 mL of the mixed solution (dichloromethane/methanol=50/15) was added and dissolved. 2 mL of the solution containing Compound 14 was put into a test tube, and 5 mL of the polymer solution was added thereto and mixed in a vortex mixer to prepare a uniform mixture. In addition, a sample to which no polymer was added was also prepared (Comparative Reference Example 9b). A nitrogen gas stream was blown to this sample, and thereby the solvent was distilled off. Then, drying was performed under a reduced pressure overnight and thereby a solid dispersion sample containing Compound 14 was obtained.

HPMCAS used in Reference Example 1b was of an MF type (specifically, regarding a substitution proportion per monomer unit, a methoxy group: 21.0 to 25.0%, a hydroxypropoxyl group: 5.0 to 9.0%, and an acetyl group: 7.0 to 11.0%, and a succinoyl group: 10.0 to 14.0%, and a viscosity: 2.4 to 3.6 mPa·s).

TABLE 2B

| | Polymer | Type | Polymer weight ratio | Manufacturer |
|---|---|---|---|---|
| Reference Example 1b | HPMCAS | MF | 25-Fold amount | Shin-Etsu Chemical Co., Ltd. |
| Comparative Reference Example 1b | HPMC | TC-5 ® | 25-Fold amount | Shin-Etsu Chemical Co., Ltd. |
| Comparative Reference Example 2b | Eudragit | S-100 | 25-Fold amount | Evonik Degussa Japan |
| Comparative Reference Example 3b | Eudragit | E-100 | 25-Fold amount | Evonik Degussa Japan |
| Comparative Reference Example 4b | Eudragit | L-100 | 25-Fold amount | Evonik Degussa Japan |

TABLE 2B-continued

| | Polymer | Type | Polymer weight ratio | Manufacturer |
|---|---|---|---|---|
| Comparative Reference Example 5b | PVP | Kollidon ®25 | 25-Fold amount | BASF Japan Ltd. |
| Comparative Reference Example 6b | PEG | 6000 | 25-Fold amount | Wako Pure Chemical Industries, Ltd. |
| Comparative Reference Example 7b | Cros-povidone | Kollidon CL-M | 25-Fold amount | BASF Japan Ltd. |
| Comparative Reference Example 8b | Poloxamer 188 | P188 | 25-Fold amount | BASF Japan Ltd. |
| Comparative Reference Example 9b | None | — | — | — |

Test Example 1b. Solubility Test 5 mL of a first fluid (pH 1.2) or 5 mL of a second fluid (pH 6.8) for an elution test in Japanese Pharmacopoeia was added to the solid dispersions of Reference Example 1b and Comparative Reference Examples 1b to 8b and the sample of Comparative Reference Example 9b, and the solid dispersions were ground using a glass rod or a spatula, and then shaking was performed at 37° C. for 2 hours. 400 μL of a mixed solution (acetonitrile/water=3/2) was immediately added to 600 μL of the sample solution filtered off using a 0.45 μm filter, and a concentration of Compound 14 in the sample solution was measured by HPLC (Shimadzu Corporation). The results are shown in Table 3B. Here, values in the table are the mean values obtained by repeating measurements twice.

TABLE 3B

| | Sample | Solubility of Compound 14 (μg/mL) |
|---|---|---|
| First fluid for elution test | Comparative Reference Example 3b | 121 |
| | Comparative Reference Example 9b | 0.39 |
| Second fluid for elution test | Reference Example 1b | 44.6 |
| | Comparative Reference Example 4b | 7.32 |
| | Comparative Reference Example 9b | 0.49 |

The solubility of Compound 14 in Comparative Reference Example 9b was 0.39 μg/mL in the first fluid and 0.49 μg/mL in the second fluid. However, in Reference Example 1b and Comparative Reference Examples 3b and 4b, the solubility increased to 5.0 μg/mL or more. In particular, Eudragit E-100 as a basic polymer in Comparative Reference Example 3b in the first fluid under acidic conditions, and HPMCAS as an acidic polymer in Reference Example 1b in the second fluid under neutral conditions had a strong effect of improving the solubility of Compound 14.

Reference Example 2b and Comparative Reference Examples 10b and 11b. Production of Solid Dispersions (Polymer, 25-Fold Amount)

Compound 14 was dissolved in tetrahydrofuran to prepare a solution having a concentration of 2.5 mg/mL. Each of polymers shown in Table 4B was dissolved in a mixed solvent (methanol/dichloromethane=3/4) to prepare a solution having a concentration of about 45 mg/mL. The solution containing Compound 14 was added to the polymer solution while stirring so that a weight ratio between Compound 14 and the polymer was 1:25. In addition, a sample to which no polymer was added was also prepared. The solution was immediately transferred into an eggplant flask, and the organic solvent was distilled off using a rotary evaporator (N-1100, Tokyo Rikakikai Co., Ltd.). The eggplant flask was transferred to a desiccator and dried under a reduced pressure for about 16 hours using a vacuum pump, and thereby a solid dispersion containing Compound 14 was obtained. The solid dispersion was dried, then ground using an agate mortar or ground using a portable high-speed grinder (LM-PLUS, Osaka Chemical Co., Ltd.), and then sieved (a sieve opening: 150 μm).

TABLE 4B

| | Polymer | Type | Polymer weight ratio | Manufacturer |
|---|---|---|---|---|
| Reference Example 2b | HPMCAS | MF | 25-Fold amount | Shin-Etsu Chemical Co., Ltd. |
| Comparative Reference Example 10b | Eudragit | E-100 | 25-Fold amount | Evonik Degussa Japan |
| Comparative Reference Example 11b | None | — | — | — |

Test Example 2b. Absorbability of Solid Dispersion Containing Compound 14 in Rats A single dose of 10 mg/kg or 30 mg/kg, as Compound 14, of the solid dispersions of Reference Example 2b and Comparative Reference Example 10b and the sample of Comparative Reference Example 11b suspended in a 1% carboxymethylcellulose aqueous solution was orally administered to fasted male rats (8 weeks old, Crl:CD (SD), Japan Charles River Laboratories). A crystalline drug substance of Compound 14 was used as a control (Comparative Reference Example 12b). A collection time was 0.5, 1, 2, 4, 8, and 24 hours after administration, and about 300 μL of blood was collected at each time point from vena caudalis (n=3). The obtained blood was centrifuged at 1500×g, 4° C. for 15 minutes to obtain a plasma. The concentration of Compound 14 in the plasma was measured by HPLC (Shiseido Company, Limited and Hitachi High-Technologies Corporation). A time to reach the highest concentration in the plasma ($T_{max}$), the highest concentration in the plasma ($C_{max}$) and an area under the plasma concentration-time curve (AUC) were calculated from the change in the concentration in the obtained plasma. The results are shown in Table 5B. Here, values in the table are the mean value±standard deviation of three examples.

The solid dispersions of Reference Example 2b and Comparative Reference Example 10b and the sample of Comparative Reference Example 11b exhibited higher absorption-improving effect on $C_{max}$ and AUC than those of the drug substance. Therefore, when Compound 14 was prepared in an amorphous form and in a solid dispersion form, improvement in the absorbability was exhibited. In addition, the solid dispersion with HPMCAS exhibited a stronger absorption-improving effect than the solid dispersion with Eudragit.

TABLE 5B

| | Dose (mg/kg) | $T_{max}$ (hr) | $C_{max}$ (ng/mL) | $AUC_{last}$ (ng · hr/mL) |
|---|---|---|---|---|
| Reference Example 2b | 10 | 2.7 ± 1.2 | 3010 ± 228 | 16416 ± 2792 |
| Reference Example 2b | 30 | 4.0 ± 3.5 | 5373 ± 587 | 63160 ± 27388 |
| Comparative Reference Example 10b | 10 | 4.0 ± 0.0 | 1936 ± 1246 | 9422 ± 5470 |
| Comparative Reference Example 10b | 30 | 8.0 ± 0.0 | 1611 ± 284 | 15120 ± 12187 |
| Comparative Reference Example 11b | 30 | 3.7 ± 3.8 | 1724 ± 65 | 15369 ± 7776 |
| Comparative Reference Example 12b | 30 | 4.7 ± 3.1 | 239 ± 99 | 1157 ± 261 |

$AUC_{last}$: Area under plasma concentration-time curve up to final observation point Reference Examples 3b, 4b, and 5b. Production of Solid Dispersions (Polymer, 25-Fold Amount)

Compound 14 was dissolved in tetrahydrofuran to prepare a solution having a concentration of 2.5 mg/mL. Each of polymers shown in Table 6B were dissolved in a mixed solvent (methanol/dichloromethane=3/4) to prepare a solution having a concentration of about 45 mg/mL. Mixing was performed so that a weight ratio between Compound 14 and the polymer was 1:25, and then the solvent was distilled off using a rotary evaporator (N-1100, Tokyo Rikakikai Co., Ltd.) under a reduced pressure at about 50° C. The obtained primary dried component was additionally subjected to secondary drying (room temperature/overnight) using a vacuum pump, and the secondary dried component was appropriately ground using a portable high-speed grinder (LM-PLUS, Osaka Chemical Co., Ltd.) and then sieved (sieve opening: 300 μm).

HPMCAS used in Reference Example 3b was of an LG type (specifically, regarding a substitution proportion per monomer unit, a methoxy group: 20.0 to 24.0%, a hydroxypropoxyl group: 5.0 to 9.0%, an acetyl group: 5.0 to 9.0%, and a succinoyl group: 14.0 to 18.0%, and a viscosity: 2.4 to 3.6 mPa·s).

HPMCAS used in Reference Example 4b was of an MG type (specifically, regarding a substitution proportion per monomer unit, a methoxy group: 21.0 to 25.0%, a hydroxypropoxyl group: 5.0 to 9.0%, an acetyl group: 7.0 to 11.0%, and a succinoyl group: 10.0 to 14.0%, and a viscosity: 2.4 to 3.6 mPa·s).

HPMCAS used in Reference Example 5b was of an HG type (specifically, regarding a substitution proportion per monomer unit, a methoxy group: 22.0 to 26.0%, a hydroxypropoxyl group: 6.0 to 10.0%, an acetyl group: 10.0 to 14.0%, and a succinoyl group: 4.0 to 8.0%, and a viscosity: 2.4 to 3.6 mPa·s).

TABLE 6B

| | Polymer | Type | Polymer weight ratio | Manufacturer |
|---|---|---|---|---|
| Reference Example 3b | HPMCAS | LG | 25-Fold amount | Shin-Etsu Chemical Co., Ltd. |
| Reference Example 4b | HPMCAS | MG | 25-Fold amount | Shin-Etsu Chemical Co., Ltd. |

TABLE 6B-continued

| | Polymer | Type | Polymer weight ratio | Manufacturer |
|---|---|---|---|---|
| Reference Example 5b | HPMCAS | HG | 25-Fold amount | Shin-Etsu Chemical Co., Ltd. |

Test Example 3b. Absorbability of Solid Dispersion Containing Compound 14 in Rats A single dose of 10 mg/kg, as Compound 14, of the solid dispersions of Reference Examples 3b, 4b, and 5b suspended in a 1% carboxymethylcellulose aqueous solution was orally administered to fasted male rats (7 to 9 weeks old, Crl:CD (SD), Japan Charles River Laboratories). A collection time was 0.5, 1, 2, 4, 8, and 24 hours after administration, and about 300 μL of blood was collected at each time point from vena caudalis (n=3). The obtained blood was centrifuged at 1500×g, 4° C. for 15 minutes to obtain a plasma. The concentration of Compound 14 in the plasma was measured by HPLC (Shiseido Company, Limited and Hitachi High-Technologies Corporation). A time to reach the highest concentration in the plasma ($T_{max}$), the highest concentration in the plasma ($C_{max}$) and an area under the plasma concentration-time curve (AUC) were calculated from the change in the concentration in the obtained plasma. The results are shown in Table 7B. Here, values in the table are the mean value±standard deviation of three examples.

In the solid dispersion of Reference Example 4b, $C_{max}$ and AUC exhibited the highest concentration in the plasma.

TABLE 7B

| | Type | Dose (mg/kg) | $T_{max}$ (hr) | $C_{max}$ (ng/ml) | $AUC_{last}$ (ng · hr/mL) |
|---|---|---|---|---|---|
| Reference Example 3b | LG | 10 | 3.3 ± 1.2 | 3089 ± 532 | 16342 ± 2494 |
| Reference Example 4b | MG | 10 | 3.3 ± 1.2 | 3961 ± 943 | 24039 ± 6189 |
| Reference Example 5b | HG | 10 | 2.3 ± 1.5 | 1836 ± 112 | 8970 ± 2058 |

$AUC_{last}$: Area under plasma concentration-time curve up to final observation point

Reference Examples 6b to 12b. Production of Solid Dispersions (HPMCAS-MG, 1- to 10-Fold Amounts)

Compound 14 was dissolved in tetrahydrofuran to prepare a solution having a concentration of 2.5 mg/mL. A HPMCAS-MG was dissolved in a mixed solvent (ethanol/water=4/1) and adjusted to about 45 mg/mL. Mixing was performed so that a weight ratio between Compound 14 and the polymer shown in Table 8B was 1:1 to 1:10. Then, the mixture was pumped into a spray dryer (GB22, Yamato Scientific Co., Ltd.) at a rate of about 5 mL/min via a peristaltic pump, and spray drying and granulation were started from a 2-fluid nozzle (with a diameter of 406 or 508 μm) at an inlet temperature of 80° C. and an outlet temperature of about 60° C. under conditions of a dry air flow of 0.32 to 0.47 $m^3$/min and a nozzle spray air pressure of 1.0 to 3.1 kgf/$cm^2$. The obtained primary dried component was additionally subjected to secondary drying (room temperature/overnight or room temperature/overnight at 40° C./day) using a vacuum pump and sieved (sieve opening: 300 μm).

TABLE 8B

| | Polymer | Type | Polymer weight ratio | Manufacturer |
|---|---|---|---|---|
| Reference Example 6b | HPMCAS | MG | 1-Fold amount | Shin-Etsu Chemical Co., Ltd. |
| Reference Example 7b | HPMCAS | MG | 2-Fold amount | Shin-Etsu Chemical Co., Ltd. |
| Reference Example 8b | HPMCAS | MG | 3-Fold amount | Shin-Etsu Chemical Co., Ltd. |
| Reference Example 9b | HPMCAS | MG | 3.5-Fold amount | Shin-Etsu Chemical Co., Ltd. |
| Reference Example 10b | HPMCAS | MG | 4-Fold amount | Shin-Etsu Chemical Co., Ltd. |
| Reference Example 11b | HPMCAS | MG | 5-Fold amount | Shin-Etsu Chemical Co., Ltd. |
| Reference Example 12b | HPMCAS | MG | 10-Fold amount | Shin-Etsu Chemical Co., Ltd. |

Test Example 4b. Absorbability of Solid Dispersion Containing Compound 14 in Rats A single dose of 10 mg/kg, as Compound 14, of the solid dispersions of Reference Examples 6b to 8b and 10b to 12b suspended in a in carboxymethylcellulose aqueous solution was orally administered to fasted male rats (7 to 9 weeks old, Crl:CD (SD), Japan Charles River Laboratories). A collection time was 0.5, 1, 2, 4, 8, and 24 hours after administration, and about 300 μL of blood was collected at each time point from vena caudalis (n=3). The obtained blood was centrifuged at 1500×g, 4° C. for 15 minutes to obtain a plasma. The concentration of Compound 14 in the plasma was measured by HPLC (Shiseido Company, Limited and Hitachi High-Technologies Corporation). A time to reach the highest concentration in the plasma ($T_{max}$), the highest concentration in the plasma ($C_{max}$) and an area under the plasma concentration-time curve (AUC) were calculated from the change in the concentration in the obtained plasma. The results are shown in Table 9B. Here, values in the table are the mean value±standard deviation of three examples.

In the solid dispersions of Reference Examples 6b to 8b and 10b to 12b, the concentration in the plasma increased in a weight ratio-dependent manner when weight ratios of HPMCAS-MG with respect to Compound 14 were 1-, 2-, and 3-folds, however, in the range of weight ratios of 4-, 5-, and 10-folds, differences in the concentration in the plasma in a weight ratio-dependent manner were not observed.

TABLE 9B

| | Polymer weight ratio | Dose (mg/kg) | $T_{max}$ (hr) | $C_{max}$ (ng/ml) | $AUC_{last}$ (ng · hr/mL) |
|---|---|---|---|---|---|
| Reference Example 6b | 1-Fold amount | 10 | 2.0 ± 1.7 | 897 ± 579 | 4680 ± 3471 |
| Reference Example 7b | 2-Fold amount | 10 | 4.7 ± 3.1 | 1955 ± 706 | 11029 ± 2832 |
| Reference Example 8b | 3-Fold amount | 10 | 3.3 ± 1.2 | 3970 ± 2048 | 23859 ± 9799 |
| Reference Example 10b | 4-Fold amount | 10 | 2.7 ± 1.2 | 3262 ± 1065 | 17959 ± 3361 |

TABLE 9B-continued

| | Polymer weight ratio | Dose (mg/kg) | $T_{max}$ (hr) | $C_{max}$ (ng/ml) | $AUC_{last}$ (ng · hr/mL) |
|---|---|---|---|---|---|
| Reference Example 11b | 5-Fold amount | 10 | 1.3 ± 0.6 | 3277 ± 604 | 18492 ± 4303 |
| Reference Example 12b | 10-Fold amount | 10 | 2.0 ± 0.0 | 3817 ± 551 | 22612 ± 1610 |

$AUC_{last}$: Area under plasma concentration-time curve up to final observation point

Test Example 5b. Evaluation of Amorphous State of Solid Dispersion Containing Compound 14 (Powder X-Ray Diffraction)

Figure 5:
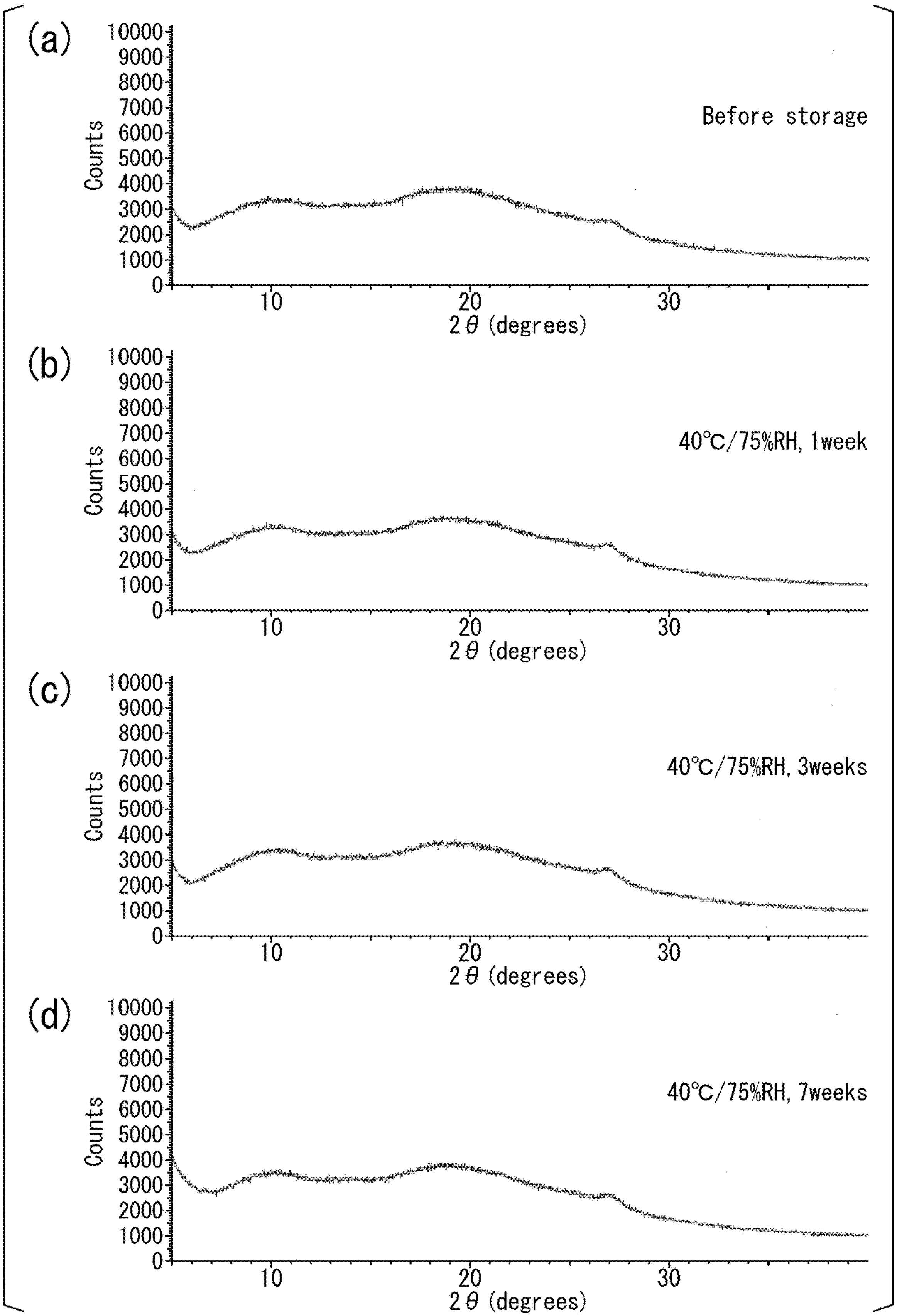
FIG. 5 is a diagram showing powder X-ray diffraction patterns of a solid dispersion of Reference Example 9b before storage and after 1 week, 3 weeks, and 7 weeks of storage under open conditions at 40° C./75% RH, respectively.
Figure 6:
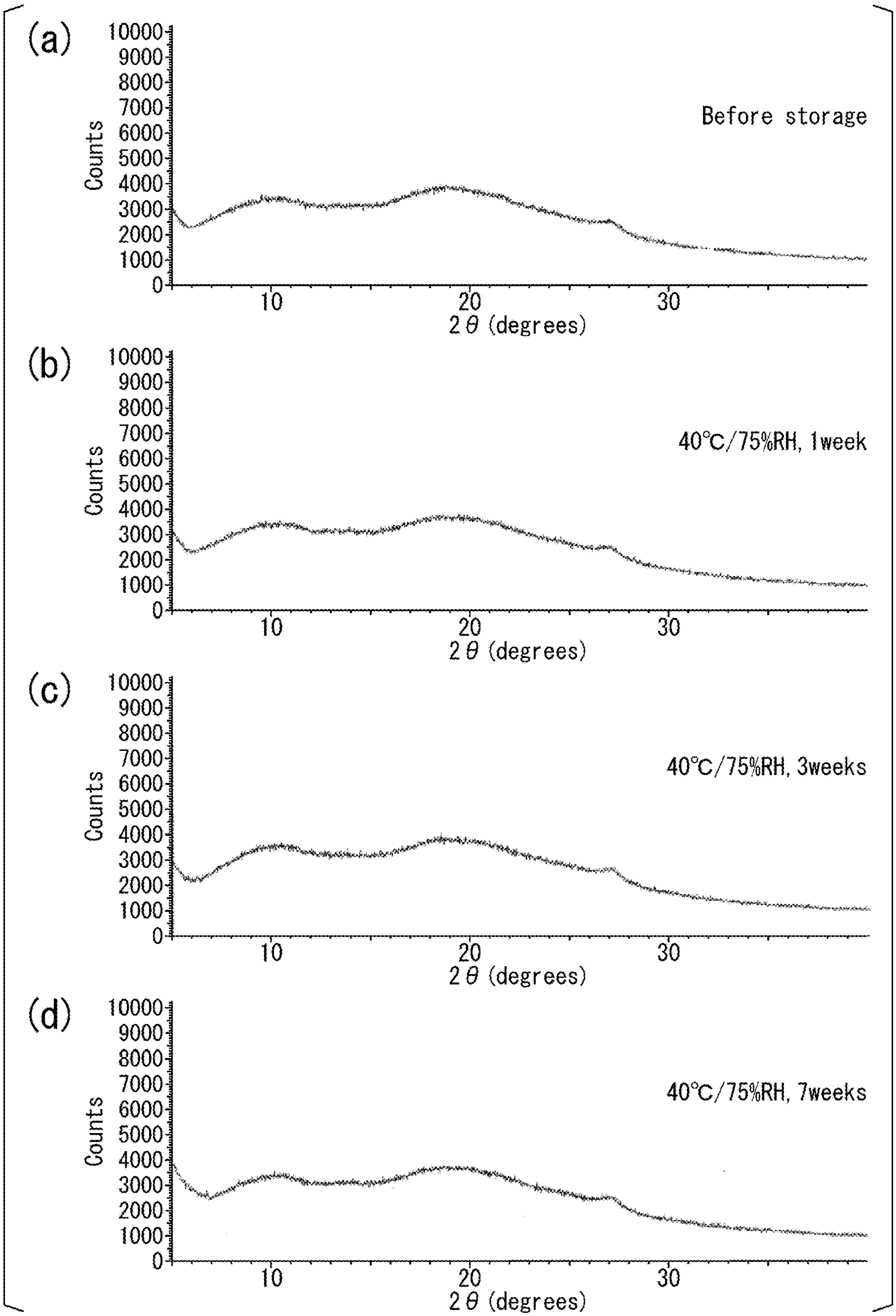
FIG. 6 is a diagram showing powder X-ray diffraction patterns of a solid dispersion of Reference Example 10b before storage and after 1 week, 3 weeks, and 7 weeks of storage under open conditions at 40° C./75% RH, respectively.
Figure 7:
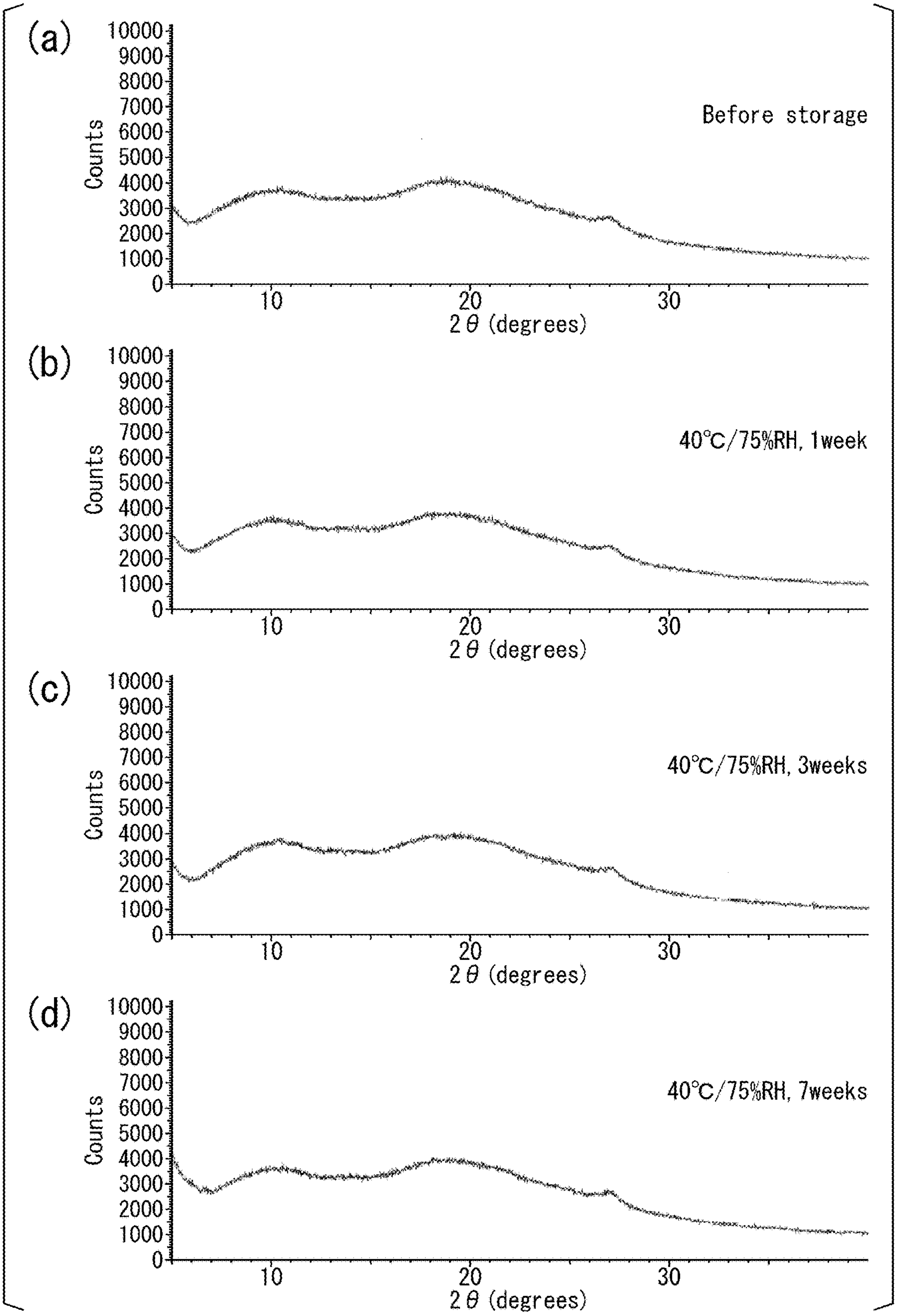
FIG. 7 is a diagram showing powder X-ray diffraction patterns of a solid dispersion of Reference Example 11b before storage and after 1 week, 3 weeks, and 7 weeks of storage under open conditions at 40° C./75% RH, respectively.

Since it is very important that the solid dispersion retains amorphous properties even after storage over time, the solid dispersions of Reference Examples 9b to 11b were stored under open conditions at 40° C./75% RH, and a change in the amorphous state was evaluated using an X-ray diffraction device (D2 Phaser, Bruker). The results are shown in FIGS. 5 to 7.

When the solid dispersions of Reference Examples 9b to 11b were stored under open conditions at 40° C./75% RH, changes in the powder X-ray diffraction pattern over time were not observed during the storage for 7 weeks.

Test Example 6b. Evaluation of Amorphous State of the Solid Dispersion Containing Compound 14 (Absorbability in Rats)

The solid dispersions of Reference Examples 9b to 11b were stored under open conditions at 40° C./75% RH, and a change in the amorphous state was evaluated according to absorbability in rats.

A single dose of 10 or 30 mg/kg, as Compound 14, of the solid dispersions of Reference Examples 9b to 11b suspended in a 1% carboxymethylcellulose aqueous solution was orally administered to fasted male rats (7 to 9 weeks old, Crl:CD (SD), Japan Charles River Laboratories). A collection time was 0.5, 1, 2, 4, 8, and 24 hours after administration, and about 300 μL of blood was collected at each time point from vena caudalis (n=3). The obtained blood was centrifuged at 1500×g, 4° C. for 15 minutes to obtain a plasma. The concentration of Compound 14 in the plasma was measured by HPLC (Shiseido Company, Limited and Hitachi High-Technologies Corporation). A time to reach the highest concentration in the plasma ($T_{max}$), the highest concentration in the plasma ($C_{max}$) and an area under the plasma concentration-time curve (AUC) were calculated from the change in the concentration in the obtained plasma. The results are shown in Table 10B. Here, values in the table are the mean value±standard deviation of three examples. When the solid dispersions of Reference Examples 9b to 11b were stored under open conditions at 40° C./75% RH, decreases in the concentration in the plasma over time were not observed during the storage for 7 weeks.

TABLE 10B

| | Dose (mg/kg) | Storage period | $T_{max}$ (hr) | $C_{max}$ (ng/mL) | $AUC_{last}$ (ng · hr/mL) |
|---|---|---|---|---|---|
| Reference | 10 | Before storage | 1.7 ± 0.6 | 3803 ± 679 | 32463 ± 15495 |
| Example 9b | | 1 week | 3.3 ± 4.0 | 3559 ± 1240 | 18449 ± 4306 |
| | | 3 weeks | 2.7 ± 1.2 | 3265 ± 847 | 19633 ± 5698 |
| | | 7 weeks | 6.7 ± 2.3 | 3570 ± 939 | 15652 ± 5301 |
| | 30 | Before storage | 4.0 ± 3.5 | 4132 ± 633 | 50613 ± 24625 |
| | | 1 week | 6.0 ± 3.5 | 5271 ± 431 | 37881 ± 8970 |
| | | 3 weeks | 4.7 ± 3.1 | 4760 ± 251 | 30196 ± 1575 |
| | | 7 weeks | 6.7 ± 2.3 | 6225 ± 1206 | 70629 ± 19727 |
| Reference Example 10b | 10 | Before storage | 2.3 ± 1.5 | 2870 ± 863 | 23235 ± 4880 |
| | | 1 week | 2.3 ± 1.5 | 3650 ± 914 | 25137 ± 13623 |
| | | 3 weeks | 2.3 ± 1.5 | 3713 ± 1006 | 21674 ± 5359 |
| | | 7 weeks | 3.3 ± 1.2 | 3859 ± 748 | 21209 ± 3935 |
| | 30 | Before storage | 2.7 ± 1.2 | 5798 ± 853 | 50798 ± 8981 |
| | | 1 week | 4.7 ± 3.1 | 6080 ± 1170 | 39819 ± 7414 |
| | | 3 weeks | 6.0 ± 3.5 | 4742 ± 990 | 29954 ± 7461 |
| | | 7 weeks | 4.0 ± 0.0 | 7704 ± 564 | 52920 ± 15388 |
| Reference Example 11b | 10 | Before storage | 6.7 ± 2.3 | 2123 ± 303 | 21294 ± 11194 |
| | | 1 week | 2.3 ± 1.5 | 3217 ± 384 | 19802 ± 2229 |
| | | 3 weeks | 6.7 ± 2.3 | 3687 ± 158 | 19240 ± 9148 |
| | | 7 weeks | 2.7 ± 1.2 | 4833 ± 411 | 24934 ± 854 |
| | 30 | Before storage | 2.7 ± 1.2 | 7557 ± 1529 | 74706 ± 40751 |
| | | 1 week | 3.3 ± 4.0 | 6002 ± 1522 | 29170 ± 10520 |
| | | 3 weeks | 2.0 ± 0.0 | 7504 ± 1978 | 48844 ± 4442 |
| | | 7 weeks | 4.0 ± 3.5 | 6624 ± 360 | 42405 ± 3280 |

$AUC_{last}$: Area under plasma concentration-time curve up to final observation point

Figure 8:
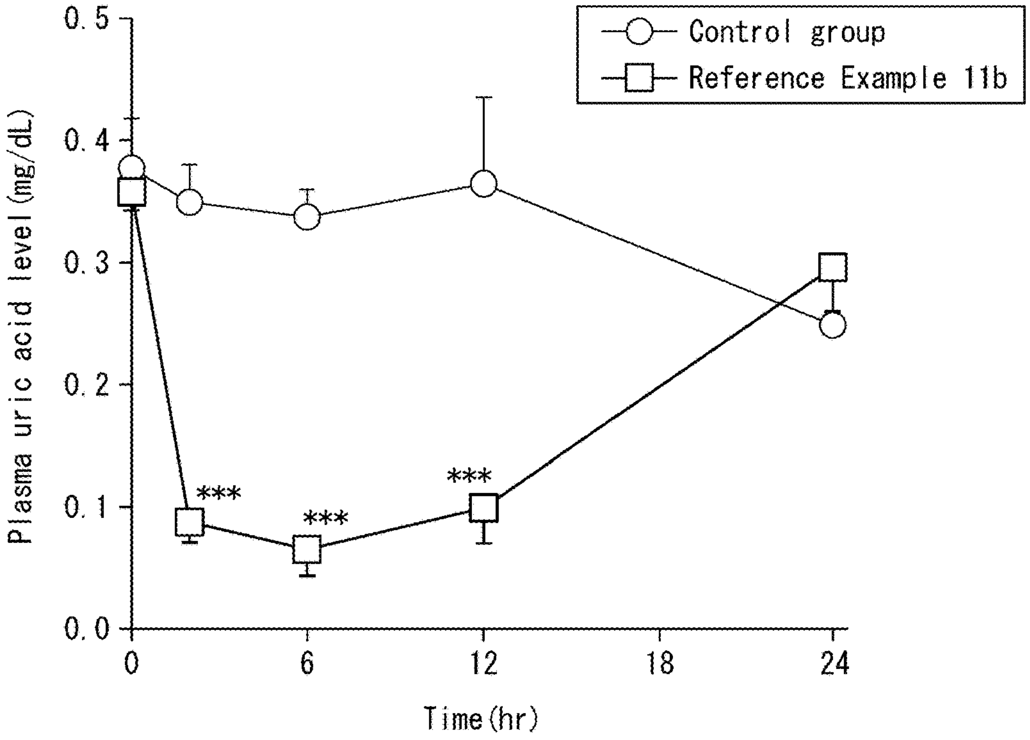
FIG. 8 is a graph showing an action of a solid dispersion of Reference Example 11b lowering a plasma uric acid level in rats.

Test Example 7b. Action of Solid Dispersion Containing Compound 14 Lowering Plasma Uric Acid Level in Rats A single dose of 30 mg/kg, as Compound 14, of the solid dispersion of Reference Example 11b suspended in a 1% carboxymethylcellulose aqueous solution was orally administered to fasted male rats (8 weeks old, Crl:CD (SD), Japan Charles River Laboratories). A 1% carboxymethylcellulose aqueous solution was used as a control. A collection time was before administration (0), and 2, 6, 12, and 24 hours after administration, and about 300 μL of blood was collected at each time point from vena caudalis (n=5). The obtained blood was centrifuged at 1500×g, 4° C. for 15 minutes to obtain a plasma. A concentration of uric acid in the plasma was measured by HPLC (Hitachi High-Technologies Corporation). Welch's t-test was performed on plasma uric acid levels at each time point of the control group and Reference Example 11b. A level of significance was $p<0.05$ (both cases). The results are shown in FIG. 8.

The plasma uric acid level after the solid dispersion of Reference Example 11b was administered was significantly lower than that of the control group, and the action of lowering a uric acid level was persistent.

Reference Examples 13b and 14b. Production of Solid Dispersions (HPMCAS-MG of 3-Fold Amount and Surfactant of 0.03-Fold Amount)

Compound 14 was dissolved in tetrahydrofuran to prepare a solution having a concentration of 2.5 mg/mL. A HPMCAS-MG was dissolved in a mixed solvent (ethanol/water=4/1) and adjusted to about 45 mg/mL. Mixing was performed so that a weight ratio among Compound 14 and the polymer and the surfactant (polysorbate 80: Tween 80 and sodium lauryl sulfate: SLS) shown in Table 11B was 1:3:0.03. Then, the mixture was pumped into a spray dryer (GB22, Yamato Scientific Co., Ltd.) at a rate of about 5 mL/min via a peristaltic pump, and spray drying and granulation were started from a 2-fluid nozzle (with a diameter of 406 or 508 μm) at an inlet temperature of 80° C. and an outlet temperature of about 60° C. under conditions of a dry air flow of 0.32 to 0.47 $m^3$/min and a nozzle spray air pressure of 1.0 to 3.1 kgf/$cm^2$. The obtained primary dried component was additionally subjected to secondary drying (room temperature/overnight or room temperature/overnight at 40° C./day) using a vacuum pump and sieved (sieve opening: 300 μm).

TABLE 11B

| | Polymer Type | Polymer weight ratio Manufacturer | Surfactant | Surfactant weight ratio Manufacturer |
|---|---|---|---|---|
| Reference Example 13b | HPMCAS MG | 3-Fold amount Shin-Etsu Chemical Co., Ltd. | Tween 80 | 0.03-Fold amount Tokyo Chemical Industry Co., Ltd. |
| Reference Example 14b | HPMCAS MG | 3-Fold amount Shin-Etsu Chemical Co., Ltd. | SLS | 0.03-Fold amount Kokusan Chemical Co., Ltd. |

Test Example 8b. Absorbability of Solid Dispersion Containing Compound 14 in Rats A single dose of 10 mg/kg, as Compound 14, of the solid dispersions of Reference Examples 13b and 14b suspended in a 1% carboxymethylcellulose aqueous solution was orally administered to fasted male rats (7 to 9 weeks old, Crl:CD (SD), Japan Charles River Laboratories). A collection time was 0.5, 1, 2, 4, 8, and 24 hours after administration, and about 300 μL of blood was collected at each time point from vena caudalis (n=3). The obtained blood was centrifuged at 1500×g, 4° C. for 15 minutes to obtain a plasma. The concentration of Compound 14 in the plasma was measured by HPLC (Shiseido Company, Limited and Hitachi High-Technologies Corporation). A time to reach the highest concentration in the plasma ($T_{max}$), the highest concentration in the plasma ($C_{max}$) and an area under the plasma concentration-time curve (AUC) were calculated from the change in the concentration in the obtained plasma. The results are shown in Table 12B together with Reference Example 8b. Here, values in the table are the mean value±standard deviation of three examples.

In the solid dispersions of Reference Examples 13b and 14b, differences were not observed in the concentration in the plasma compared to Reference Example 8b containing no surfactant.

TABLE 12B

| | Polymer weight ratio/ Surfactant weight ratio | Dose (mg/kg) | $T_{max}$ (hr) | $C_{max}$ (ng/mL) | $AUC_{last}$ (ng · hr/mL) |
|---|---|---|---|---|---|
| Reference Example 13b | 3-Fold amount/0.03-Fold amount | 10 | 3.3 ± 1.2 | 3625 ± 1335 | 21420 ± 4825 |
| Reference Example 14b | 3-Fold amount/0.03-Fold amount | 10 | 2.7 ± 1.2 | 3589 ± 1370 | 21318 ± 6599 |
| Reference Example 8b | 3-Fold amount | 10 | 3.3 ± 1.2 | 3970 ± 2048 | 23859 ± 9799 |

$AUC_{last}$: Area under plasma concentration-time curve to final observation point Reference Example 14

Figure 9:
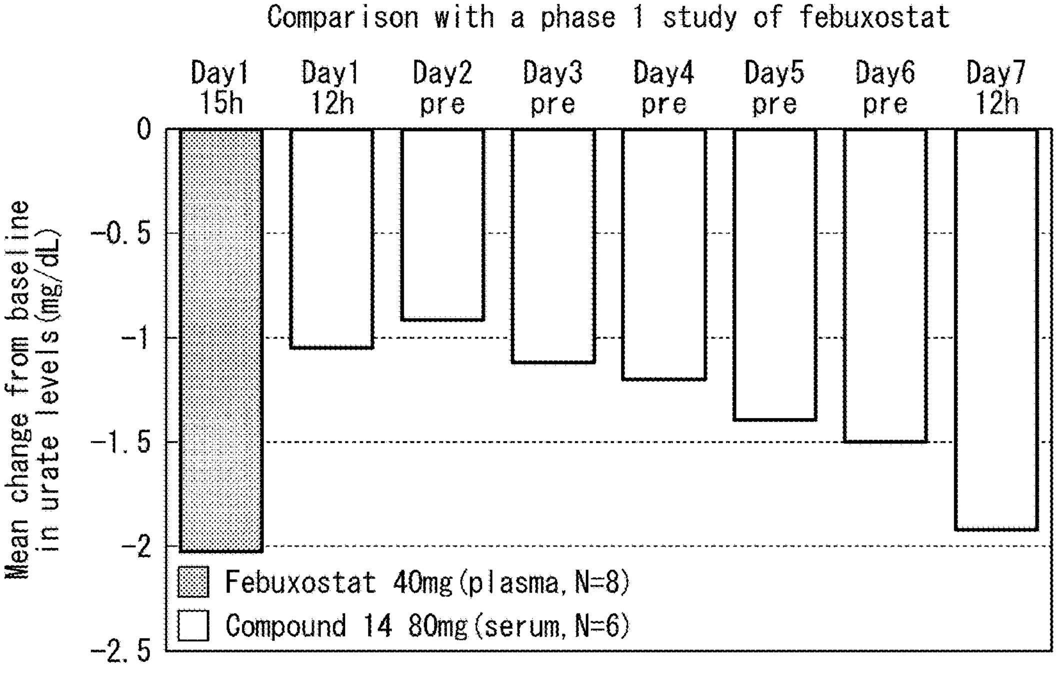
FIG. 9 is a diagram showing the decrease in the serum uric acid level when Compound 14 and febuxostat as a control drug were orally administered to healthy adult males in Reference Example 14.

80 mg of Compound 14 was repeatedly administered to 6 healthy adult males once daily for 7 days using solid dispersion capsules of Formulation Example 1, and the action of lowering a serum uric acid level was examined. For comparative reference, the results are shown in FIG. 9 together with the result of a case described in Non Patent Literature 3 in which febuxostat (40 mg) was used.

As a result, with febuxostat, the maximum rate of decrease in a blood uric acid level reached about 35% on the first day of the administration (about 15 hours after the administration), indicating a rapid decrease in the serum uric acid level. On the other hand, the maximum rate of decrease in a blood uric acid level was about 17% on the first day of the administration of Compound 14 (12 hours after the administration), and the serum uric acid level was mildly decreased. Thereafter, the serum uric acid level gradually decreased over time throughout the administration period, and the maximum rate of decrease in a blood uric acid level reached about 30% on the seventh day (about 8 hours after the administration).

From these results, Compound 14 is expected to prevent a gout attack or reduce the number of gout attacks.

In addition, as a result of repeated administration of 20 mg of Compound 14 once daily for 7 days using the solid dispersion capsules of Formulation Example 1, the serum uric acid level gradually decreased over time throughout the administration period, which is similar to the result of administering 80 mg of Compound 14 once daily, and 24 hours after the final administration, the serum uric acid level decreased by about 10 to 20% as compared with the serum uric acid level before the administration (initial value).

In addition, as a result of repeated administration of 40 mg of Compound 14 once daily for 7 days using capsules containing micronized Compound 14 (instead of the solid dispersion capsules), the serum uric acid level gradually decreased over time throughout the administration period, which is similar to the results in the cases of using the solid dispersion capsules.

Reference Example 15

Compound 14 suspended in a 1% aqueous methylcellulose solution was orally administered to oxonic acid-induced hyperuricemic rats at a dose of 0.3 mg/kg once a day for 28 days under non-fasting conditions. As a control, a 1% aqueous methylcellulose solution was used, and as a positive control, febuxostat was used.

(Preparation of Oxonic Acid-Induced Hyperuricemic Rat)

As rats, male Crl:CD (SD) rats (produced by Charles River Laboratories Japan, Inc.) were used. The rats were purchased at the age of 6 weeks, and the administration was started at the age of 7 weeks.

Potassium oxonate was prepared by adding and suspending 10 g of potassium oxonate (Sigma-Aldrich Corp., Lot No. 03810 HD) to 200 mL of 1% methyl cellulose (1% MC) with a mixer. After suspending, the temperature was kept at about 37° C. in a water bath until immediately before administration. The preparation was performed as a matter of business.

The oxonic acid-induced hyperuricemic rats were prepared by subcutaneously administering potassium oxonate (suspended in a 1% aqueous methylcellulose solution) at a dose of 250 mg/kg 2.5 hours before each blood collection on Days 1, 7, 14, 21, and 28 of administration.

(Test Method)

The collection time points were set to before administration (1 hour before) and 2 and 6 hours after administration on Days 1, 7, 14, 21, and 28, and blood was collected in an amount of about 300 μL per time point from the tail vein (n=7). The obtained blood was centrifuged at 1500×g, 4° C. for 15 minutes to obtain plasma. The concentration of uric acid in the plasma was measured by HPLC (Shiseido Co., Ltd., current OSAKA SODA).

To acquire the predose value and data for grouping, a 1% aqueous methylcellulose solution was orally administered to all rats 5 days before the start of administration, and the uric acid concentration in the plasma was measured according to the above-described method such as subcutaneous administration of potassium oxonate.

The averages and standard deviations were calculated for the plasma uric acid level and the area under the concentration-time curve (plasma uric acid level AUC (−1) to 6 hr) of the plasma uric acid level up to 6 hr after administration. For the plasma uric acid level AUC (−1) to 6 hr on each administration day, the rate of change (%) for each individual in the Compound 14 and febuxostat administration groups with respect to the average of the control group was determined, and the average and the standard deviation were calculated. Further, in each group, a paired t-test was performed for the rates of change on Day 1 and Day 7 and thereafter.

(Results)

Figure 10:
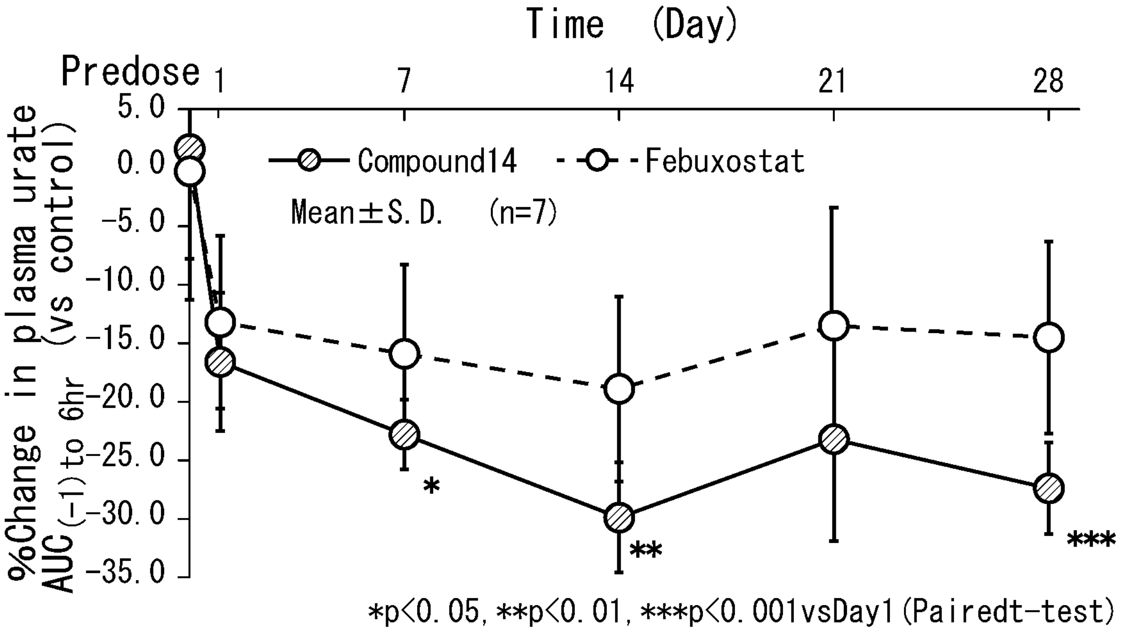
FIG. 10 is a diagram showing the rate of change in plasma uric acid levels when Compound 14 and febuxostat as a control drug were orally administered once a day repeatedly for 28 days to oxonic acid-induced hyperuricemic rats in Reference Example 15.

The results are shown in FIG. 10. In the Compound 14 administration group, the rate of change of the plasma uric acid level AUC (−1) to 6 with respect to the control group increased with repeated administration, but in the febuxostat administration group, no clear increase was observed, supporting that Compound 14 continuously suppresses xanthine oxidoreductase as compared with febuxostat.

Example 1, ATP Enhancing Action in Hypoxic Condition

Figure 11:
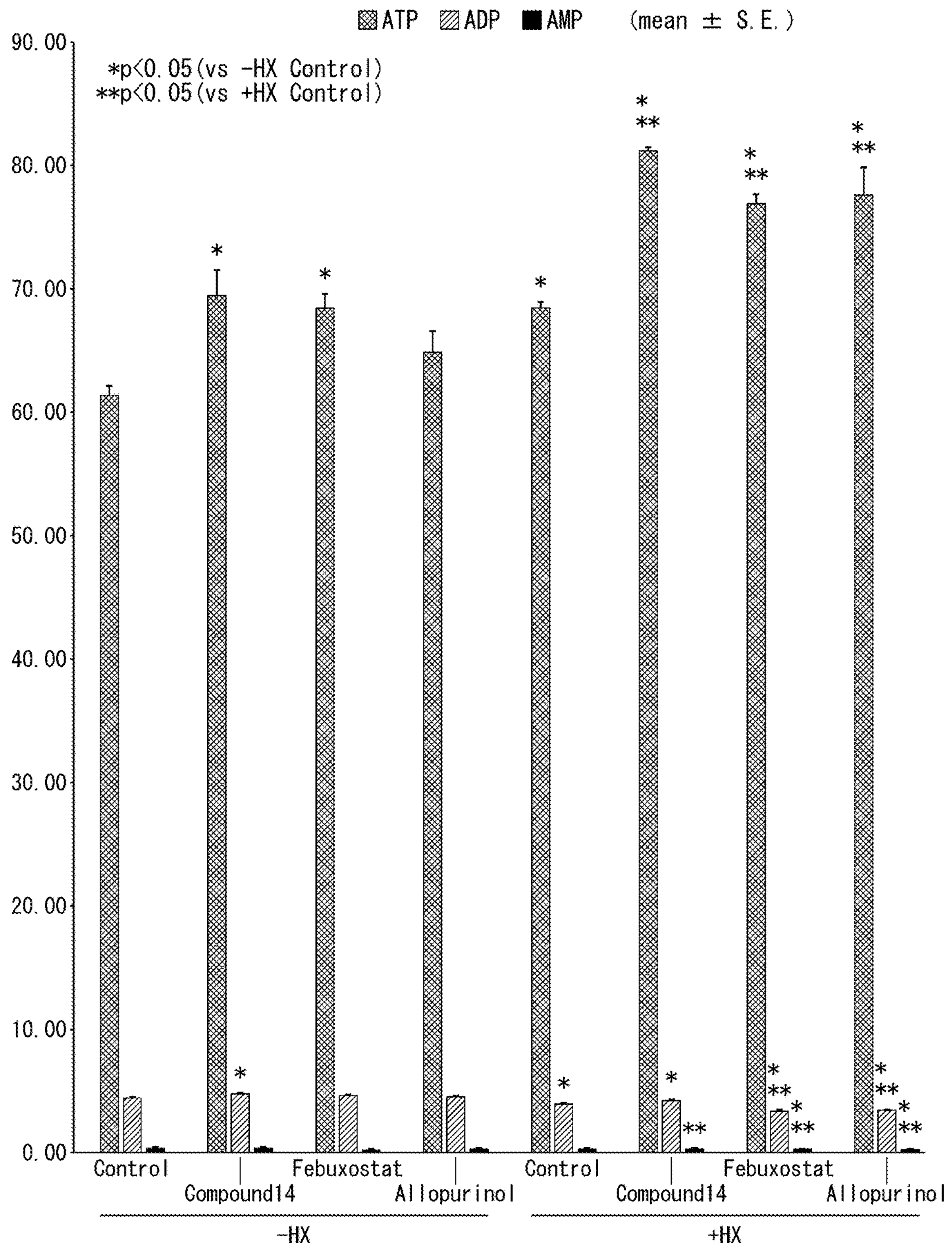
FIG. 11 is a diagram showing an ATP enhancing action in a hypoxic condition in Example 1.
Figure 12:
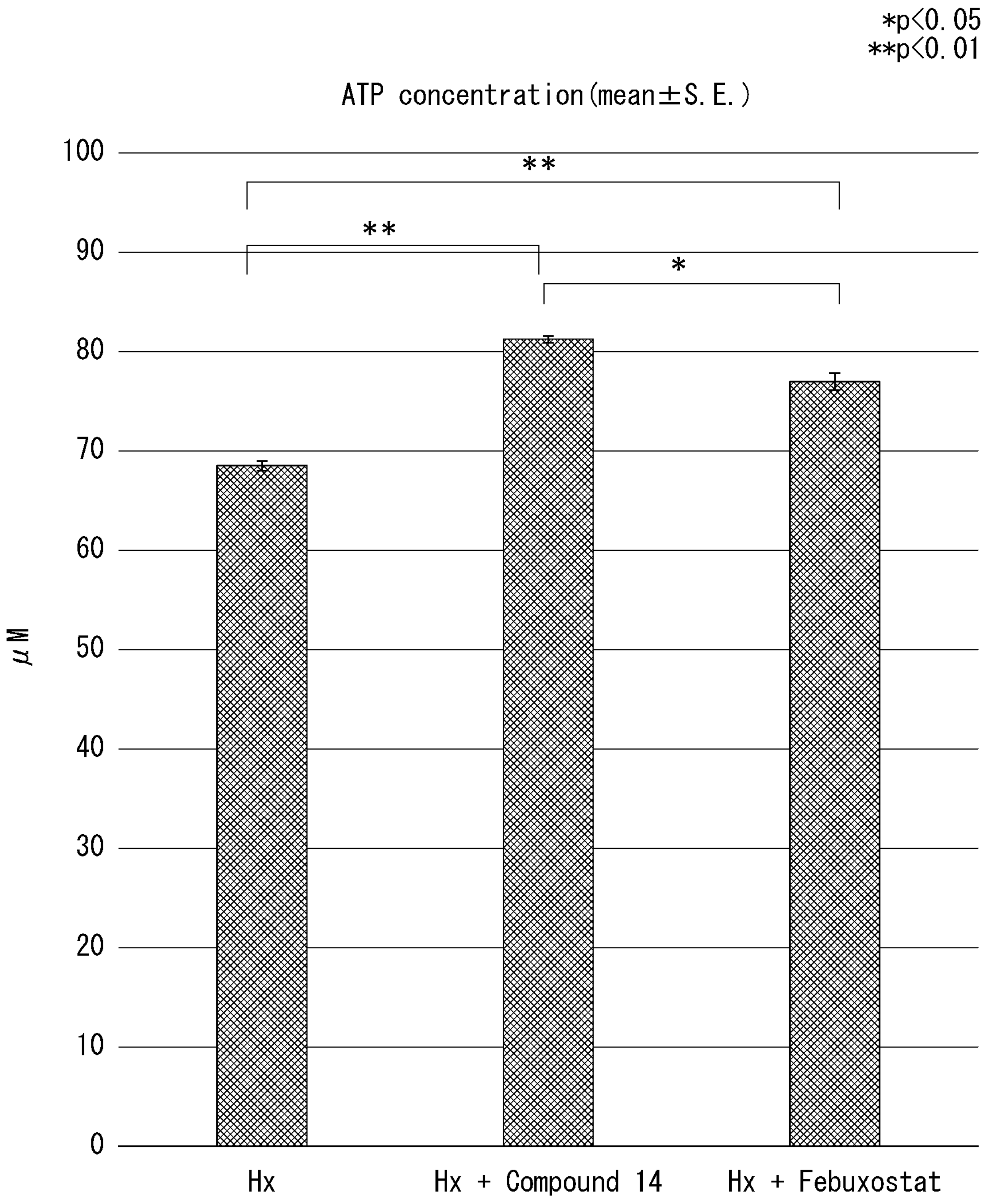
FIG. 12 is a diagram showing an ATP enhancing action in hypoxic condition in Example 1, showing a significant difference between Compound 14 and febuxostat when hypoxanthine was administered in combination.

MOVAS-1 cells having XOR activity were used for Examples. All examinations were performed at n=3 for each number of samples. The medium of MOVAS-1 cells in a confluent state (with D-MEM/low glucose/10% FBS/100 μM Oxionate) was divided into a medium for a hypoxanthine addition group and a medium for a hypoxanthine non-addition group, 50 μM hypoxanthine, and 6 μM Compound 14, 10 μM febuxostat, or 100 μM allopurinol were added to the medium of the hypoxanthine addition group, and 6 μM Compound 14, 10 μM febuxostat, or 100 μM allopurinol was added to the medium of the hypoxanthine non-addition group. For the control of each group, only 50 μM hypoxanthine was added to the hypoxanthine addition group, and nothing was added to the hypoxanthine non-addition group. Thereafter, the media were allowed to stand for 4 hours under mixed gas conditions of 1% oxygen, 5% carbon dioxide, and 94% nitrogen. After deproteinization by PCA, ATP, ADP and AMP concentrations were measured using HPLC. The results are shown in FIGS. 11 and 12. Compound 14 exhibited effects at doses lower than febuxostat and allopurinol.

Example 2, ATP Enhancing Action in Presence of Uncoupler

Figure 13:
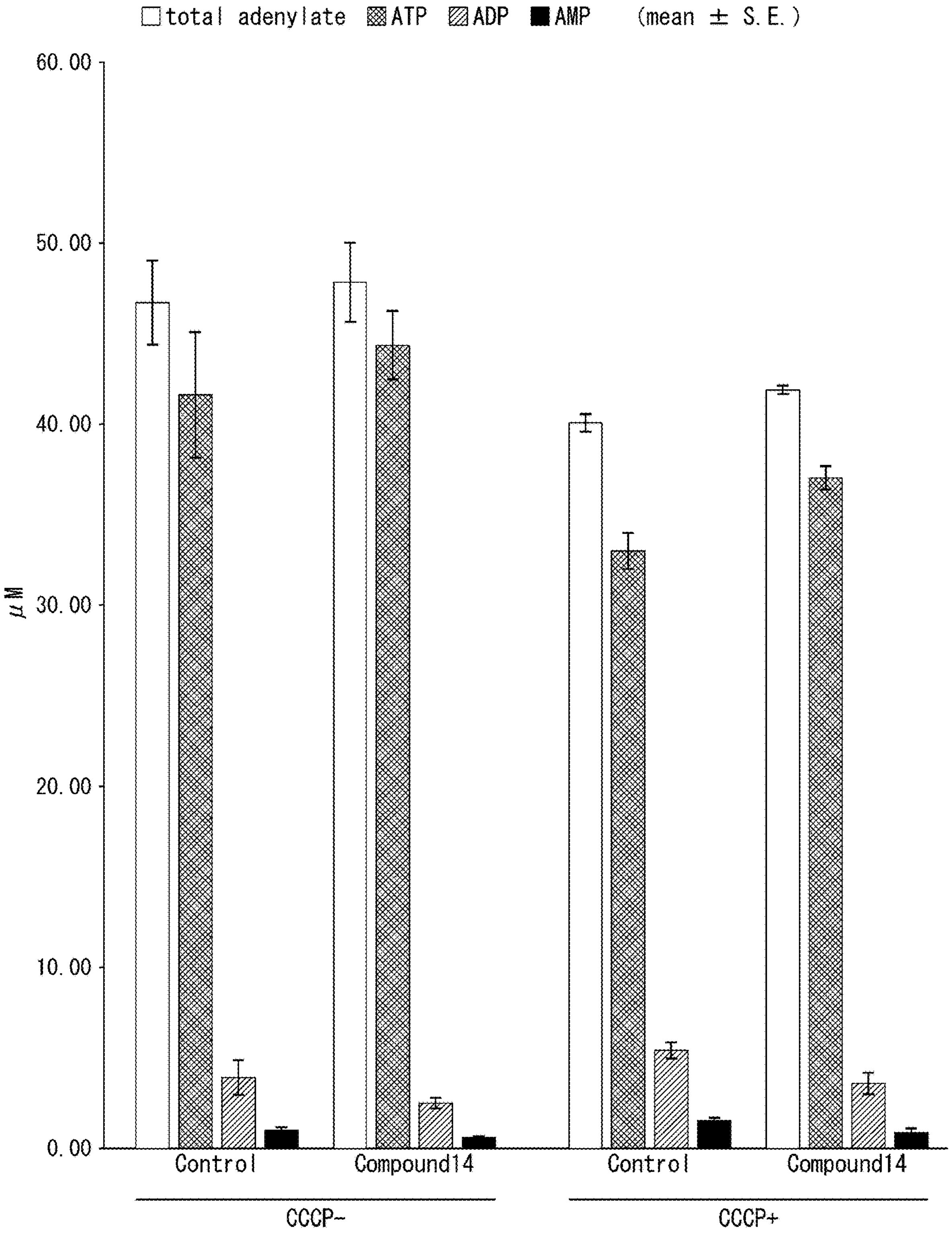
FIG. 13 is a diagram showing an ATP enhancing action in presence of an uncoupler in Example 2.

MOVAS-1 cells having XOR activity were used for Examples. All examinations were performed at n=3 for each number of samples. The medium of MOVAS-1 cells in a confluent state (with D-MEM/low glucose/10% FBS/100 uM Oxionate) was divided into a medium for a CCCP addition group and a medium for a CCCP non-addition group, and 6 μM Compound 14 was added to the media. Nothing was added to the control of each group. Thereafter, to the CCCP addition group, CCCP was added so as to have a final concentration of 10 μM. After standing for 30 minutes, deproteinization was performed by PCA, and then ATP, ADP, and AMP concentrations were measured using HPLC. The results are shown in FIG. 13. The results of the controls showed that the total adenylate concentrations were decreased by addition of CCCP. The total adenylate concentration of the CCCP addition group to which Compound 14 was added was higher than the total adenylate concentration of the control group of the CCCP addition group.

Example 3, Suppressive Action on Retinal Degeneration

Three week old RCS rats (CLEA Japan, Inc., male) were purchased and randomly divided into a control group and a Compound 14 administration group. From 3.5 weeks of age, control and Compound 14 were orally administered daily once a day for 18 days. To the control group, 1% methylcellulose (Metrose (SM-15) manufactured by Shin-Etsu Chemical Co., Ltd.) was administered, and to the Compound 14 administration group, a preparation in which a solid dispersion of Compound 14 described in "Formulation Example 1" described later was suspended in 1% methylcellulose was administered at a dose of 5 mg/100 g body weight (1 mg/100 g body weight as Compound 14) per administration. Because xanthine stones are likely to occur in rodents due to XOR inhibition, Uralyt-U combination powder (manufactured by Nippon Chemiphar Co., Ltd.) was administered to both groups in drinking water at a concentration of 1% (w/v) in order to prevent/reduce xanthine stones. On Day 19 after completion of administration for 18 days, eyeballs of both eyes were collected from both groups, and a tissue image was observed on one eyeball.

Figure 14:
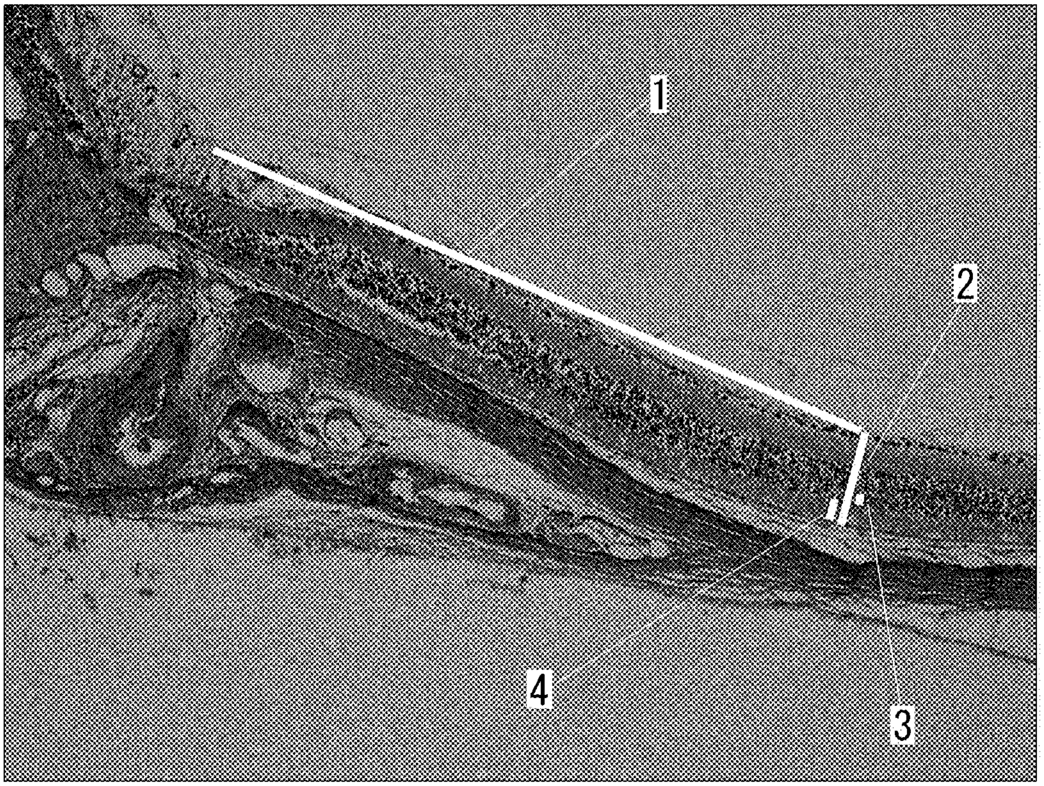
FIG. 14 is a sagittal eyeball tissue specimen (HE staining) including an optic nerve of an RCS rat (5 weeks old, male). 1 to 4 represent the distance from the center of the macula, the thickness of the retina, the thickness of the outer nuclear layer, and the thickness of the cone-rod layer, and are 1011 μm, 128 μm, 13 μm, and 27 μm, respectively.

To compare the thicknesses of layers of the retina, as shown in FIG. 14, the measurement points were the thickness (2) of the retina, the thickness (3) of the outer nuclear layer, and the thickness (4) of the cone-rod layer at a point a certain distance (1000 μm) away from the central part of the optic disc.

Figure 15:
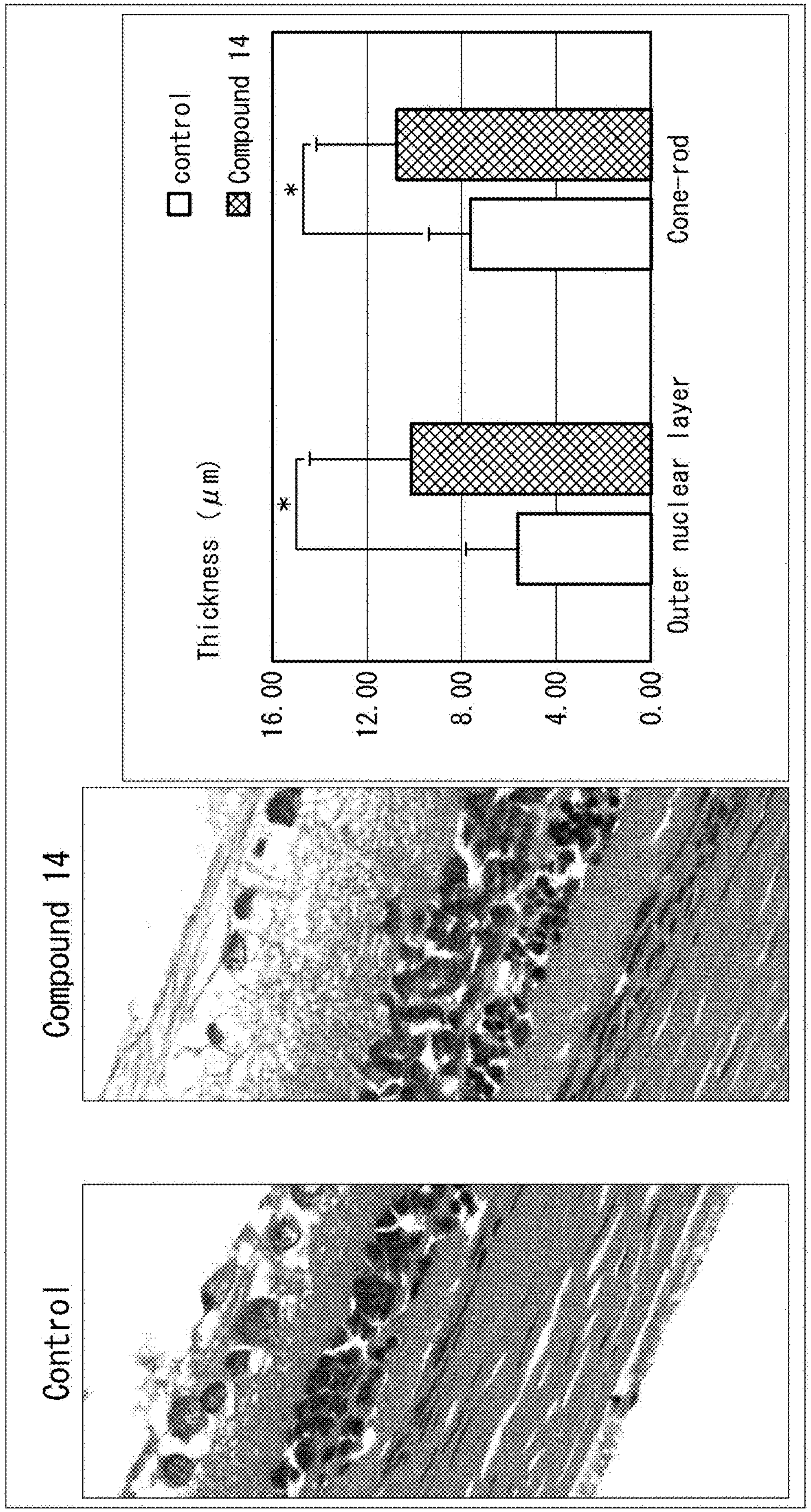
FIG. 15 shows cross-sectional views of the retinas after administration of control or Compound 14 and a graph showing the thicknesses of the outer nuclear layer and the cone-rod layer in Example 3.

The results are shown in FIG. 15. As a result, relative to the control group, in the Compound 14 administration group, thinning of the outer nuclear layer and the cone-rod layer in the retinal tissue was significantly suppressed ($p<0.05$; n=4).

The other eyeball was subjected to concentration measurement of various factors in the eyeball in Example 4.

Reference Example 16, Confirmation of XOR in Eyeball

The retina was isolated from the collected rat eyeball, frozen with liquid nitrogen, and stored at −80° C. until enzyme activity measurement. The retina was homogenized in solution [50 mM potassium phosphate buffer (pH 7.4) containing 0.25 M sucrose, 1 mM salicylic acid, 0.3 mM EDTA, protease inhibitory agent (Roche Applied Science; complete protease inhibitor cocktail)] and then centrifuged at 15000×g to prepare supernatant. The protein concentration in the supernatant was measured (manufactured by Thermo Fisher Scientific; Coomassie (Bradford) Protein Assay Regent). The XOR enzyme reaction was performed in a 50 mM potassium phosphate buffer (pH 7.8) solution containing [0.4 mM EDTA, 0.15 mM xanthine, 500 μM $NAD^+$ at 25° C. The concentration of the product uric acid was measured with absorbance at a wavelength of 295 nM.

The XOR activity in rat retinal lysate was below the detection limit (0.01 nmole uric acid/min/mg protein).

Example 4, Measurement of Concentration of Various Molecules in Eyeball

Concentrations of various molecules in one eyeball collected in Example 3 were measured. The eyeball stored at −80° C. was freeze-pulverized, a 5% perchloric acid solution in an amount of 2 times (w/w) was added, and the mixture was vortexed. The supernatant obtained by centrifugation at 15000 rpm and 4° C. for 5 minutes was neutralized with a 3 M potassium carbonate solution. The mixture was centrifuged again at 15000 rpm and 4° C. for 5 minutes, and the supernatant was equilibrated with 0.5 M sodium phosphate buffer to prepare an eyeball extraction solution. ATP, ADP, AMP, IMP, inosine, hypoxanthine, xanthine, uric acid, GTP, GDP, and GMP in the solution were measured by HPLC (HPLC: Shimadzu Corporation LC-20AD, Diode array detector: Shimadzu Corporation SPD-M20A), and the energy charge was calculated (Calculation formula: ([ATP]+ ½ [ADP])/([ATP]+[ADP]+[AMP])).

The results are shown in Tables 13 to 15. Compound 14 was found to significantly increase the energy charge in the eyeball by increasing ATP, ADP, GTP, and GDP and decreasing AMP and IMP.GTP represents guanosine triphosphate, GDP represents guanosine diphosphate, and GMP represents guanosine monophosphate.

TABLE 13

| Administration group | ATP | ADP | AMP | IMP |
|---|---|---|---|---|
| Control | 138.757 ± 8.746 | 33.438 ± 5.891 | 46.245 ± 5.126 | 22.149 ± 7.090 |
| Compound 14 | 175.809 ± 25.506 | 55.134 ± 7.253 | 27.828 ± 8.547 | 3.640 ± 1.122 |
| Significant difference # | *p = 0.033 | **p = 0.004 | *p = 0.010 | **p = 0.002 |

Test by student's t-test:
*p < 0.05,
**p < 0.01

TABLE 14

| Administration group | Inosine | Hypoxanthine | Xanthine | Uric acid |
|---|---|---|---|---|
| Control | 25.283 ± 8.646 | 13.434 ± 3.479 | 3.625 ± 1.814 | 3.238 ± 1.224 |
| Compound 14 | 13.063 ± 4.690 | 8.450 ± 3.244 | 1.739 ± 0.590 | 1.344 ± 0.444 |
| Significant difference # | *p = 0.047 | NS p = 0.081 | NS p = 0.095 | *p = 0.027 |

Test by student's t-test:
*p < 0.05,
**p < 0.01

TABLE 15

| Administration group | GTP | GDP | GMP | Energy charge |
|---|---|---|---|---|
| Control | 43.428 ± 2.764 | 5.754 ± 1.229 | 21.020 ± 3.441 | 0.712 ± 0.021 |
| Compound 14 | 53.157 ± 8.352 | 8.115 ± 1.245 | 2.458 ± 1.898 | 0.786 ± 0.030 |
| Significant difference # | NS p = 0.069 | *p = 0.036 | **p = 0. 000 | **p = 0.007 |

Test by student's t-test:
*p < 0.05,
**p < 0.01

Example 5, Measurement of Concentration of Hypoxane and Inosine in Serum

In the same manner as in Example 3, to RCS rats, control or Compound 14 was orally administered daily for 10 days, and Uralyt-U combination powder (manufactured by Nippon Chemiphar Co., Ltd.) was administered in drinking water. On Day 11 after completion of administration for 10 days, blood was collected from both groups to prepare serum. As shown in Table 16, the concentration of inosine and the concentration of hypoxanthine in the serum were significantly increased by Compound 14 by about 38 times and about 7 times, respectively ($p<0.05$; $n=4$).

TABLE 16

| Administration | Serum (n = 4) | |
|---|---|---|
| group | Inosine | Hypoxanthine |
| Control | 0.260 ± 0.300 | 12.550 ± 0.850 |
| Compound 14 | 9.950 ± 6.280 | 92.020 ± 47.670 |
| Significant difference # | *p = 0.026 | *p = 0.023 |

Test by student's t-test:
*p < 0.05

According to the result of Reference Example 16, the XOR enzyme is presumably scarcely present in the retina. This is consistent with low RNA expression levels in humans, pigs and mice in the known database "THE HUMAN PROTEIN ATLAS" (https://www.proteinatlas.org/ENSG00000158125-XDH/tissue). Meanwhile, as shown in Table 13, it was confirmed that the ATP concentration in the eyeball significantly increased by the oral administration of Compound 14 as compared with the control group, and as shown in Table 16, the concentrations of inosine and hypoxanthine in the serum significantly increased.

From the above results, it is presumed that when Compound 14 is orally administered, xanthine oxidoreductase (XOR) present in the liver, vascular endothelium, and the like is inhibited, AMP degradation in the tissue is stopped at hypoxanthine, the amount of hypoxanthine and inosine in the blood is increased, hypoxanthine and inosine in the blood pass through the blood-retinal barrier, then hypoxanthine and inosine flow into the retina and are regenerated to ATP via the purine salvage cycle in the retina to increase ATP concentration in the eyeball. Then, presumably, the increased ATP promotes repair of disorders in the retinal tissue and protects the retinal cells from degeneration, thereby suppressing thinning of the outer nuclear layer and the cone-rod layer in the retinal tissue. The fact that Compound 14 indirectly acts on the eyeball is also supported by the fact that the Compound 14 administered to the rat was hardly distributed in the eyeball.

Age-related maculopathy, glaucoma, and the like are also treated by increasing the concentration of ATP in the eyeball (Maruoka et al., Heliyon 4 (2018) e00624; Nakano et al., Heliyon 2 (2016) e00096), and thus XOR inhibitors such as Compound 14 presumably have a therapeutic effect even in these diseases.

Formulation Example 1, Production of Solid Dispersion Capsules

After dissolving 0.18 kg of Compound 14 (2-(3-cyano-4-phenoxyphenyl)-7-hydroxythiazolo[5,4-d]pyrimidine) in 38.72 kg of a mixed solvent of tetrahydrofuran (may be abbreviated as THF), absolute ethanol, and purified water (weight ratio: 32.01/5.09/1.62) while heating, 0.72 kg of HPMCAS-MG was added thereto and stirred to prepare a feed solution. Then, the feed solution was spray dried with a spray dryer under the conditions of a heat input temperature of 100° C., a heat output temperature of 60° C., a liquid feed rate of 100 g/min, and a 2-fluid nozzle nitrogen spray pressure of 0.30 MPa. The obtained spray-dried product was vacuum dried for 16 hours at a drying temperature of 25° C. and for 24 hours at 40° C. Then, the vacuum-dried product was air dried for 24 hours at room temperature to obtain a solid dispersion containing Compound 14.

The obtained solid dispersion containing Compound 14 was sieved through a sieve (sieve opening of 300 μm), and then 50 g of sodium starch glycolate was added to and mixed with 250 g of the sieved solid dispersion to obtain a mixed powder of the solid dispersion containing Compound 14.

No. 2 white gelatin capsules were each filled with 60 mg or 120 mg of the obtained mixed powder of the solid dispersion containing Compound 14 to obtain solid dispersion capsules of Compound 14.

The pharmaceutical composition provided by the present invention is useful as a pharmaceutical composition for enhancing intracellular ATP. In particular, the pharmaceutical composition provided by the present invention is useful as a pharmaceutical composition for enhancing intracellular ATP without use of inosine, inosinic acid, hypoxanthine, or a salt thereof in combination even when the pharmaceutical composition is a pharmaceutical composition including only a compound represented by General Formula (I) or a pharmaceutically acceptable salt thereof as an active ingredient.

The invention claimed is:

1. A method of treating or preventing an ATP-related eye disease, comprising administering an effective amount of a pharmaceutical composition to a subject in need thereof to treat or prevent an ATP-related eye disease, wherein the pharmaceutical composition comprises a compound represented by General Formula (I):

(I)

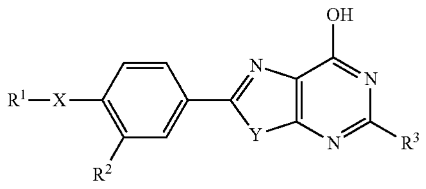

wherein $R^1$ represents an unsubstituted phenyl group or a phenyl group substituted with a substituent, the substituent represents at least one group selected from the group consisting of an alkyl group having 1 to 8 carbon atoms, an alkyl group having 1 to 8 carbon atoms substituted with a halogen atom, an alkoxy group having 1 to 8 carbon atoms, an alkoxycarbonyl group having 2 to 8 carbon atoms, a formyl group, a carboxyl group, a halogen atom, a phenyl group, and a phenoxy group, $R^2$ represents a cyano group or a nitro group, $R^3$ represents a hydrogen atom or a hydroxyl group, X represents an oxygen atom or $—S(O)_n—$, n represents an integer of 0 to 2, and Y represents an oxygen atom or a sulfur atom, or a pharmaceutically acceptable salt thereof.

2. The method according to claim 1, wherein the eye disease is a disease with a retinal or optic nerve disorder.

3. The method according to claim 1, wherein the ATP-related eye disease is retinitis pigmentosa, cone-rod dystrophy, Oguchi disease, fundus albipunctatus, pigmented paravenous retinochoroidal atrophy, Leber congenital amaurosis, cone dystrophy, Stargardt disease, Best disease, familial exudative vitreoretinopathy, Wagner syndrome, Stickler syndrome, central areolar choroidal dystrophy, choroideremia, gyrus-like choroidal dystrophy, retinal degeneration secondary to uveitis, a retinal degenerative disease, retinal vein occlusion, retinal artery occlusion, hypertensive retinopathy, diabetic retinopathy, renal retinopathy, age-related macular degeneration, central serous chorioretinopathy, retinal white spot syndrome, angioid streaks of the retina, rhegmatogenous retinal detachment involving the macula, macular hole, retinoschisis, exudative retinal detachment, proliferative vitreoretinopathy, retinal detachment associated with high myopia, Usher syndrome, Bardet-Biedl syndrome, Kearns-Sayre syndrome, Refsum syndrome, glaucoma, optic neuritis, ischemic optic neuropathy, compressive optic neuropathy, rhinogenous optic neuropathy, demyelinating optic neuropathy disease, or toxic optic neuropathy.

4. The method according to claim 1, wherein the compound represented by General Formula (I) or a pharmaceutically acceptable salt thereof in the pharmaceutical composition is orally administered to a patient in need of enhancement of intracellular ATP at 10 to 320 mg per day, and optionally, the oral administration is continued for at least 7 days.

5. The method according to claim 1, wherein in the compound in the pharmaceutical composition, R1 is an unsubstituted phenyl group or a phenyl group substituted with a halogen atom.

6. The method according to claim 1, wherein in the compound in the pharmaceutical composition, X is an oxygen atom.

7. The method according to claim 1, wherein in the compound in the pharmaceutical composition, Y is a sulfur atom.

8. The method according to claim 1, wherein the compound or a pharmaceutically acceptable salt thereof in the pharmaceutical composition, comprises an amorphous form thereof, and a content of the amorphous form is 80% by weight or more based on a total weight of the compound or a pharmaceutically acceptable salt thereof.

9. The method according to claim 1, wherein the pharmaceutical composition is an enteric-coated preparation.

10. The method according to claim 9, wherein the enteric-coated preparation is a hard capsule preparation.

11. The method according to claim 1, wherein the pharmaceutical composition further comprises a solid dispersion comprising a hypromellose derivative.

12. The method according to claim 11, wherein a weight ratio between the compound represented by General Formula (I) or a pharmaceutically acceptable salt thereof and the hypromellose derivative is 1:0.1 to 1:25.

13. The method according to claim 11, wherein the hypromellose derivative is hypromellose acetate succinate or hypromellose phthalate.

14. The method according to claim 1, wherein the pharmaceutical composition is a solid preparation.

15. The method according to claim 1, wherein a content of the compound represented by General Formula (I) or a pharmaceutically acceptable salt thereof in the pharmaceutical composition is 10 mg to 320 mg.

16. The method according to claim 1, wherein a content of the compound represented by General Formula (I) or a pharmaceutically acceptable salt thereof per dosage unit is 10 mg to 320 mg.

17. The method according to claim 1, wherein a content of the compound represented by General Formula (I) or a pharmaceutically acceptable salt thereof per dosage unit is 10 mg to 160 mg.

18. The method according to claim 1, wherein a content of the compound represented by General Formula (I) or a pharmaceutically acceptable salt thereof per dosage unit is 10 mg to 80 mg.

19. The method according to claim 1, wherein a content of the compound represented by General Formula (I) or a pharmaceutically acceptable salt thereof per dosage unit is 20 mg to 80 mg.

20. The method according to claim 1, wherein the compound represented by General Formula (I) or a pharmaceutically acceptable salt thereof in the pharmaceutical composition is 2-(3-cyano-4-phenoxyphenyl)-7-hydroxythiazolo [5,4-d]pyrimidine or a pharmaceutically acceptable salt thereof.

21. The method according to claim 3, wherein the retinal degenerative disease is a drug-induced retinal disorder.

22. The method according to claim 21, wherein the drug-induced retinal disorder is a chloroquine-induced retinal disorder.

23. The method according to claim 3, wherein the demyelinating optic neuropathy disease is multiple sclerosis.

24. The method according to claim 3, wherein the toxic optic neuropathy disease is caused by ethambutol, methanol, or thinner.

* * * * *